(12) United States Patent
Colacot et al.

(10) Patent No.: US 9,777,030 B2
(45) Date of Patent: Oct. 3, 2017

(54) COMPLEXES

(71) Applicant: JOHNSON MATTHEY PUBLIC LIMITED COMPANY, London (GB)

(72) Inventors: Thomas Colacot, West Deptford, NJ (US); Andrew Jon Deangelis, West Deptford, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/317,725

(22) PCT Filed: Mar. 20, 2015

(86) PCT No.: PCT/GB2015/050837
§ 371 (c)(1),
(2) Date: Dec. 9, 2016

(87) PCT Pub. No.: WO2015/189555
PCT Pub. Date: Dec. 17, 2015

(65) Prior Publication Data
US 2017/0120231 A1    May 4, 2017

Related U.S. Application Data

(60) Provisional application No. 62/011,184, filed on Jun. 12, 2014.

(51) Int. Cl.
| | |
|---|---|
| *C07F 15/00* | (2006.01) |
| *B01J 31/24* | (2006.01) |
| *C07C 213/02* | (2006.01) |
| *C07C 67/343* | (2006.01) |
| *C07C 231/08* | (2006.01) |
| *C07D 317/66* | (2006.01) |
| *C07D 213/74* | (2006.01) |
| *C07D 401/12* | (2006.01) |
| *C07D 471/04* | (2006.01) |
| *C07D 409/12* | (2006.01) |
| *C07B 43/04* | (2006.01) |

(Continued)

(52) U.S. Cl.
CPC ............ *C07F 15/006* (2013.01); *B01J 31/24* (2013.01); *C07B 37/02* (2013.01); *C07B 43/04* (2013.01); *C07B 47/00* (2013.01); *C07C 67/343* (2013.01); *C07C 213/02* (2013.01); *C07C 231/08* (2013.01); *C07D 207/27* (2013.01); *C07D 209/08* (2013.01); *C07D 213/74* (2013.01); *C07D 213/76* (2013.01); *C07D 215/38* (2013.01); *C07D 217/02* (2013.01); *C07D 231/44* (2013.01); *C07D 241/20* (2013.01); *C07D 263/22* (2013.01); *C07D 263/24* (2013.01); *C07D 277/42* (2013.01); *C07D 317/66* (2013.01); *C07D 401/04* (2013.01); *C07D 401/12* (2013.01); *C07D 405/12* (2013.01); *C07D 409/12* (2013.01); *C07D 417/12* (2013.01); *C07D 471/04* (2013.01); *B01J 2231/44* (2013.01); *B01J 2531/824* (2013.01)

(58) Field of Classification Search
CPC ..................................................... C07F 15/006
See application file for complete search history.

(56) References Cited

FOREIGN PATENT DOCUMENTS

| WO | 2011/161451 A1 | 12/2011 | |
|---|---|---|---|
| WO | WO 2011161451 A1 * | 12/2011 | .......... B01J 31/2291 |

OTHER PUBLICATIONS

Borjian et al., "NMR Studies of the Species Present in Cross-Coupling Catalysis Systems Involving Pd(n3—1—Ph—C3H4)(n5—C5H5) and [Pdn3—1—Ph—C3H4)Cl]2 Activated by PBut3, XPhos, and Mor-Dalphos: Nonexistence of Pd (XPhos)n and Pd(Mor-Dalphos)n (n—1, 2) at Moderate Temperatures", Organometallics 2014, 33, pp. 3936-3940.

(Continued)

Primary Examiner — Joseph Kosack
(74) Attorney, Agent, or Firm — Baker & Hostetler LLP

(57) ABSTRACT

A palladium(II) complex of formula (1) or a palladium(II) complex of formula (3).

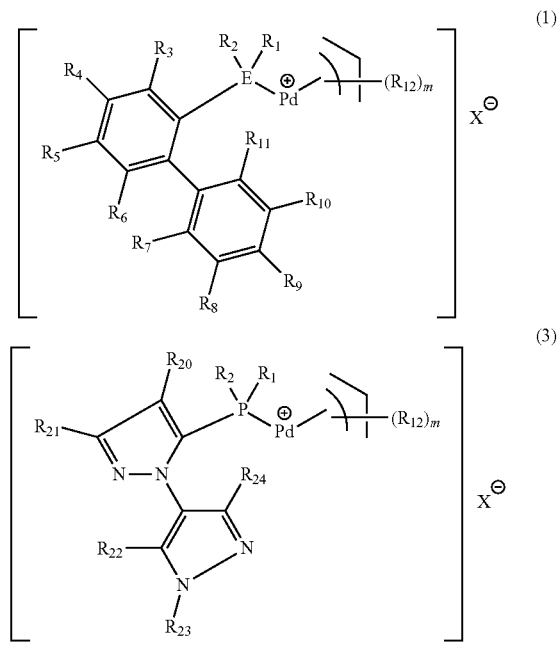

Also, processes for the preparation of the complexes, and their use in carbon-carbon and carbon-heteroatom coupling reactions.

30 Claims, 11 Drawing Sheets

(51) Int. Cl.

| | | |
|---|---|---|
| C07B 37/02 | (2006.01) | |
| C07B 47/00 | (2006.01) | |
| C07D 231/44 | (2006.01) | |
| C07D 215/38 | (2006.01) | |
| C07D 417/12 | (2006.01) | |
| C07D 405/12 | (2006.01) | |
| C07D 207/27 | (2006.01) | |
| C07D 263/22 | (2006.01) | |
| C07D 263/24 | (2006.01) | |
| C07D 277/42 | (2006.01) | |
| C07D 241/20 | (2006.01) | |
| C07D 217/02 | (2006.01) | |
| C07D 213/76 | (2006.01) | |
| C07D 209/08 | (2006.01) | |
| C07D 401/04 | (2006.01) | |

(56) References Cited

OTHER PUBLICATIONS

Noél-Duchesneau et al., "Tailoring Buchwald-Type Phosphines with Pyrimidinium Betaines as Versatile Aryl Group Surrogates", Organometallics 2014, 33, pp. 5085-5088.

Kočovský et al., Palladium(II) Complexes of 2-Dimethylamino-2'-diphenylphosphino-1,1'-binaphthyl (MAP) with Unique P,Co-Coordination and Their Catalytic Activity in Allylic Substitution, Hartwig-Buchwald Amination, and Suzuki coupling, J. Am. Chem. Soc., vol. 121, No. 33, 1999, pp. 7714-7715.

Rodriguez, Lara-Isabel et al: "Carbosilane Dendrimers Peripherally Functionalized with P-Stereogenic Monophosphines. Catalytic Behavior of Their Allylpalladium Complexes in the Asymmetric Hydrovinylation of Styrene", Organometallics, vol. 25, No. 6, Mar. 1, 2006 (Mar. 1, 2006), pp. 1368-1376, XP55189638, ISSN: 3276-7333, Barcelona, Spain.

Grabulosa, Arnald et al: "Better Performance of Monodentate P-Stereogenic Phosphanes Compared to Bidentate Analogues in Pd-Catalyzed Asymmetric Allylic Alkylations", European Journal of Inorganic Chemistry, vol. 2010, No. 21, Jun. 2, 2010 (Jun. 2, 2010), pp. 3372-3383, XP55189614, ISSN: 1434-1948, Barcelona, Spain.

Clavero, Pau et al: "P-Stereogenic monophosphines with the 2-p-terphenylyl and 1-pyrenyl substituents. Application to Pd and Ru asymmetric catalysis", Journal of Molecular Catalysis A: Chemical, vol. 391, Apr. 26, 2014 (Apr. 26, 2014), pp. 183-190, XP028852059, ISSN: 1381-1169, Barcelona, Spain.

International Search Report dated Jun. 2, 2015, in corresponding PCT application PCT/GB2015/050837.

Ficks, Arne et al., "MOP-phosphonites: A novel ligand class for asymmertic catalysis", Dalton Transactions, vol. 41 (12), 2012, pp. 3515-3522, ISSN: 1477-9226, New Castle, UK.

Rodriguez, Lara-Isabel et al: "Palladocarbosilane dendrons in supercritical carbon dioxide. Catalytic behaviour in the asymmetric hydrovinylation of styrene", Journal of Super critical Fluids, vol. 55(3),2011, pp. 1023-1026, ISSN: 3896-8446, Barcelona, Spain.

Rodriguez, Lara-Isabel et al: "Palladocarbosilane dendrimers as catalysts for the asymmetric hydrovinylation of styrene in supercritical carbon dioxide", Journal of Organometallic Chemistry, vol. 693(10), 2008, pp. 1857-1860, ISSN: 0022-328X, Barcelona, Spain.

Kumar, P. G. Anil et al., "Bonding in Palladium (II) and Plantinum (II) Allyl MeO-and H-MOP Complexes. Subtle Differences via 13C NMR", Organometallics, vol. 24(6), 2005, pp. 1306-1314, ISSN: 0276-7333, Zurich, Switzerland.

Great Britian Search Report dated Dec. 14, 2015, in corresponding application GB1504784.8.

Grabulosa, Arnald et al: "Allylpalladium Complexes with P-Stereogenic Monodentate Phosphines. Application in the Asymmetric Hydrovinylation of Styrene", Organometallics, vol. 24 (21), 2005, pp. 4961-4973, Barcelona, Spain.

* cited by examiner

COMPLEXES

The present invention relates to optionally substituted cationic π-allyl palladium complexes and their use thereof in coupling reactions.

WO2011/161451 (to Johnson Matthey PLC) describes π-allyl complexes, such as π-allyl palladium complexes and π-allyl nickel complexes. WO2011/161451, however, neither discloses nor suggests cationic π-allyl palladium complexes The use of [(allyl)PdCl]$_2$ or [(cinnamyl)PdCl]$_2$ in combination with biaryl/heteroaryl phosphine ligands, such as Buchwald ligands in coupling reactions has proven to be of limited and unpredictable success. In an attempt to overcome the limitations of catalyst generation from palladium sources such as [(allyl)PdCl]$_2$, Pd(dba)$_x$ (x=1, 1.5 or 2), or Pd(OAc)$_2$ with Buchwald ligand combinations, the Buchwald group at MIT has introduced a library of three generations of palladacycle precatalysts utilizing bulky biarylphosphines as shown below.

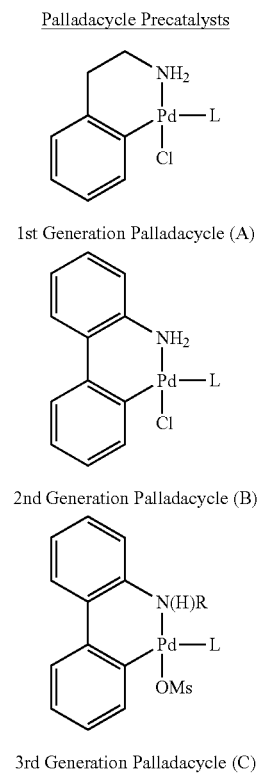

Palladacycle Precatalysts

1st Generation Palladacycle (A)

2nd Generation Palladacycle (B)

3rd Generation Palladacycle (C)

R = H, Me, Ph

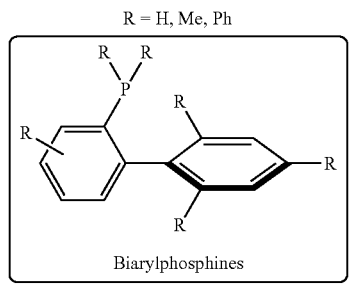

Biarylphosphines

The palladacycles, however, demonstrate a number of limitations. Firstly, the synthesis of the 1$^{st}$ generation palladacycles requires several steps including the generation of an unstable intermediate [(TMEDA)PdMe$_2$]. The scope of the 2$^{nd}$ generation precatalysts is limited as extremely bulky ligands such as tBuXPhos cannot be incorporated. The syntheses of the 2$^{nd}$ and 3$^{rd}$ generation palladacycles require the use of potentially toxic 2-aminobiphenyl, which can be contaminated with the highly toxic 4-isomer, requiring the need for high purity raw material. Furthermore, the activation of the 2$^{nd}$ and 3$^{rd}$ generation palladacycles generates an equivalent of genotoxic carbazole. The starting material aminobiphenyl and the by-product carbazole can contaminate reaction mixtures. Hence, purification can be complicated, in addition to the consideration of health and safety concerns involved in handling these materials. Moreover, the reductively eliminated carbazole (as illustrated in the following figure) can consume aryl-electrophile starting material and also significantly retard the rate of some cross-coupling reactions.

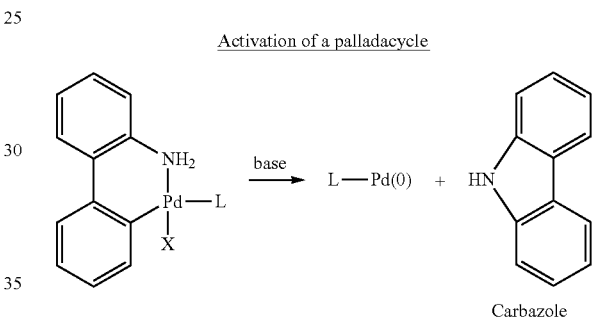

Activation of a palladacycle

Carbazole

The activation of the very recent N-substituted 3$^{rd}$ generation palladacycles generates an equivalent of either N-methylcarbazole or N-phenylcarbazole and little is known about their toxicity. The N-substituted version of the 3$^{rd}$ generation palladacycles also require an additional synthetic step to prepare relative to the unsubstituted analogues, and the incorporation of extremely bulky ligands (i.e. tBu-BrettPhos, RockPhos, etc.) was not successful with these N-substituted complexes.

There remains a need to provide palladium precatalysts with well-defined ligand/palladium ratios which can incorporate extremely bulky ligands and which overcome the limitations in the prior art.

SUMMARY OF THE INVENTION

In many cases, allyl dimers such as [(allyl)PdCl]$_2$ do not function well as palladium sources with biarylphosphines and there are difficulties in forming active catalysts with the allyl dimer/Buchwald ligand combination. The present inventors have discovered a class of cationic π-allylpalladium complexes, which may be employed to effect a variety of reactions, such as C—N and C—C bond formation reactions. In certain embodiments, the cationic π-allyl complexes are highly active catalysts. In certain embodiments, the cationic π-allyl complexes are stable to air and moisture at ambient temperatures.

In one aspect, the invention provides a palladium(II) complex of formula (1):

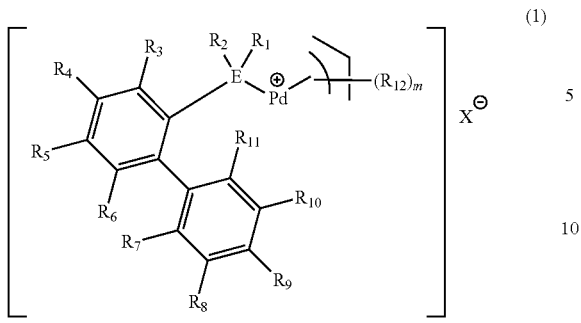

(1)

wherein:
Pd$^\oplus$ is a cationic palladium atom;
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above; $R_{12}$ is an organic group having 1-20 carbon atoms;
m is 0, 1, 2, 3, 4 or 5;
E is P or As; and
$X^\ominus$ is a non-coordinated anionic ligand.

In another aspect, the invention provides a palladium complex of formula (3):

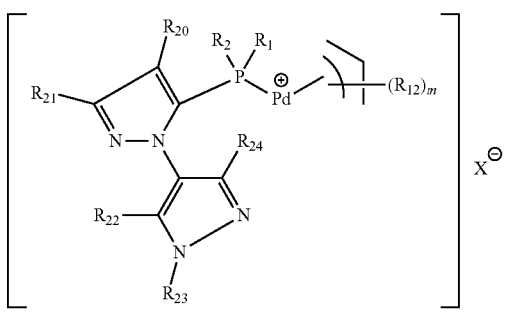

(3)

wherein:
$R_1$ and $R_2$ are independently organic groups having 1-20 carbon atoms, or $R_1$ and $R_2$ are linked to form a ring structure with E;
$R_{12}$ is an organic group having 1-20 carbon atoms;
$R_{20}$, $R_{21}$, $R_{22}$, $R_{23}$ and $R_{24}$ are independently —H or organic groups having 1-20 carbon atoms; or one or more pairs selected from $R_1/R_{20}$, $R_2/R_{20}$, $R_{20}/R_{21}$ or $R_{22}/R_{23}$ may independently form a ring structure with the atoms to which they are attached;
m is 0, 1, 2, 3, 4 or 5; and
$X^\ominus$ is a non-coordinated anionic ligand.

In another aspect, the invention provides a process for the preparation of a complex of formula (1), the process comprising the steps of:
(a) reacting a complex of formula (4) with a monodentate biaryl ligand of formula (5) to form a complex of formula (6)

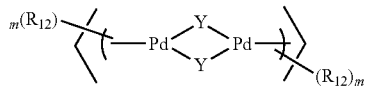

(4)

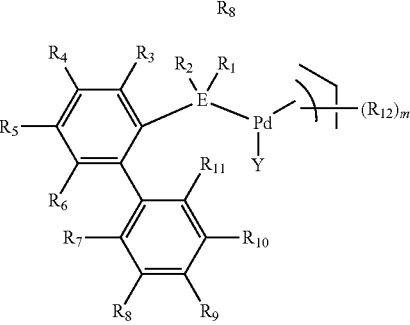

(5)

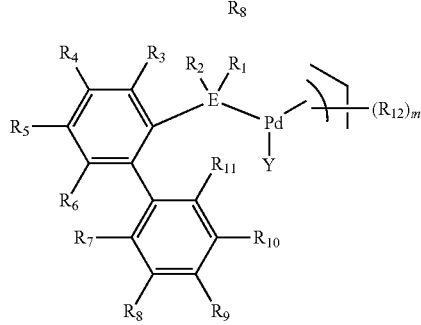

(6)

and;
(b) reacting the complex of formula (6) with a silver salt of formula (7) to form the complex of formula (1), AgX (7)

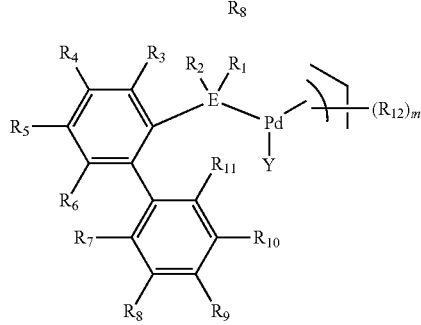

(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
one or more pairs selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$ independently form a ring structure with the atoms to which they are attached;
$R_{12}$ is an organic group having 1-20 carbon atoms;
m is 0, 1, 2, 3, 4 or 5;
E is P or As;
Y is a coordinating anionic ligand; and
$X^\ominus$ is a non-coordinated anionic ligand.

In another aspect, the invention provides a process for the preparation of a complex of formula (1) or a complex of formula (3), the process comprising the steps of:

(a) reacting a complex of formula (4) with a silver salt of formula (7),

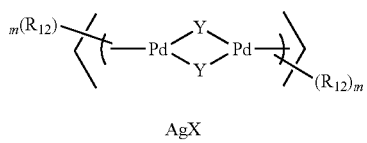
(4)

AgX (7)

and;
(b) reacting the product of step (a) with a monodentate biaryl ligand of formula (5) or a monodentate bi-heteroaryl tertiary phosphine ligand of formula (8) to form the complex of formula (1) or the complex of formula (3).

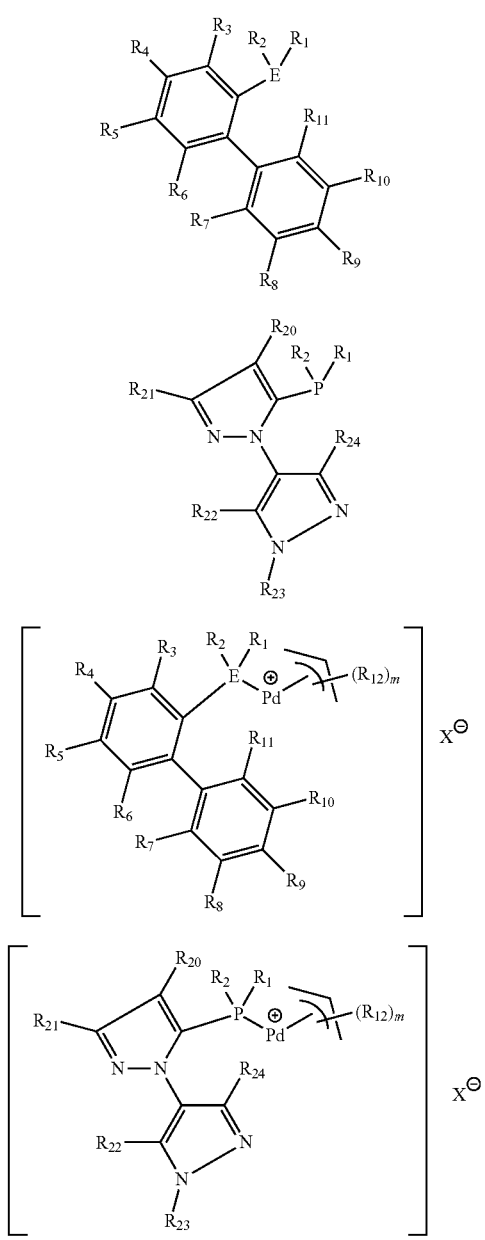

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or one or more pairs selected from $R_1/R_2$, $R_2/R_3$, $R_3/R_4$, $R_4/R_5$, $R_5/R_6$, $R_7/R_8$, $R_8/R_9$, $R_9/R_{10}$ or $R_{10}/R_{11}$ independently form a ring structure with the atoms to which they are attached;
$R_{12}$ is an organic group having 1-20 carbon atoms;
$R_{20}$, $R_{21}$, $R_{22}$, $R_{23}$ and $R_{24}$ are independently —H or organic groups having 1-20 carbon atoms; or one or both pairs selected from $R_1/R_{20}$, $R_2/R_{20}$, $R_{20}/R_{21}$ or $R_{22}/R_{23}$ may independently form a ring structure with the atoms to which they are attached;
m is 0, 1, 2, 3, 4 or 5;
E is P or As;
Y is a coordinating anionic ligand; and
$X^{\ominus}$ is a non-coordinated anionic ligand.

In another aspect, the invention provides a process for carrying out a carbon-carbon coupling reaction in the presence of a catalyst, the process comprising the use of a complex of formula (1) or a complex of formula (3) as defined herein.

In another aspect, the invention provides a process for carrying out a carbon-heteroatom coupling reaction in the presence of a catalyst, the process comprising the use of a complex of formula (1) or a complex of formula (2) as defined herein.

In another aspect, the invention provides a use of a complex of formula (1) or a complex of formula (2) as defined herein as a catalyst in carbon-carbon coupling reactions.

In another aspect, the invention provides a use of a complex of formula (1) or a complex of formula (2) as defined herein as a catalyst in carbon-heteroatom coupling reactions.

DEFINITIONS

The point of attachment of a moiety or substituent is represented by "—". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

The term "cycloalkyl" is used to denote a saturated carbocyclic hydrocarbon radical. The cycloalkyl group may have a single ring or multiple condensed rings. In certain embodiments, the cycloalkyl group may have from 3-15 carbon atoms, in certain embodiments, from 3-10 carbon atoms, in certain embodiments, from 3-8 carbon atoms. The cycloalkyl group may be unsubstituted. Alternatively, the cycloalkyl group may be substituted. Unless other specified, the cycloalkyl group may be attached at any suitable carbon atom and, if substituted, may be substituted at any suitable atom. Typical cycloalkyl groups include but are not limited to cyclopropyl, cyclobutyl, cyclopentyl, cyclohexyl, adamantyl and the like.

"Alkoxy" refers to an optionally substituted group of the formula alkyl-O— or cycloalkyl-O—, wherein alkyl and cycloalkyl are as defined above.

"Alkoxyalkyl" refers to an optionally substituted group of the formula alkoxy-alkyl-, wherein alkoxy and alkyl are as defined above.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Coupling" refers to a chemical reaction in which two molecules or parts of a molecule join together (Oxford Dictionary of Chemistry, Sixth Edition, 2008).

"Halo" or "hal" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). The heteroalkyl group may be unsubstituted. Alternatively, the heteroalkyl group may be substituted. Unless otherwise specified, the heteroalkyl group may be attached at any suitable atom and, if substituted, may be substituted at any suitable atom. Examples of heteroalkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). The heterocycloalkyl group may be unsubstituted. Alternatively, the heterocycloalkyl group may be substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). The heteroaryl group may be unsubstituted. Alternatively, the heteroaryl group may be substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more hydrogen atoms are each independently replaced with substituents (e.g. 1, 2, 3, 4, 5 or more) which may be the same or different. Examples of substituents include but are not limited to -halo, —C(halo)$_3$, —R$^a$, =O, =S, —O—R$^a$, —S—R$^a$, —NR$^a$R$^b$, —CN, —NO$_2$, —C(O)—R$^a$, —COOR$^a$, —C(S)—R$^a$, —C(S)OR$^a$, —S(O)$_2$OH, —S(O)$_2$—R$^a$, —S(O)$_2$NR$^a$R$^b$, —O—S(O)—R$^a$ and —CONR$^a$R$^b$, such as -halo, —C(halo)$_3$ (e.g. —CF$_3$), —R$^a$, —O—R$^a$, —NR$^a$R$^b$, —CN, or —NO$_2$. R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group. R$^a$ and R$^b$ may be unsubstituted or further substituted as defined herein.

"Thioalkyl" refers to an optionally substituted group of the formula alkyl-S— or cycloalkyl-S—, wherein alkyl and cycloalkyl are as defined above.

DETAILED DESCRIPTION

In one aspect, the present invention provides a palladium (II) complex of formula (1):

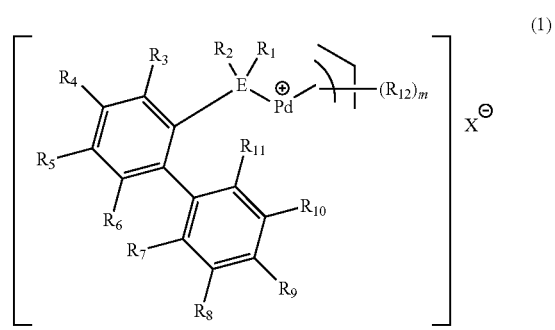

wherein:

Pd$^\oplus$ is a cationic palladium atom;

R$_1$ and R$_2$ are independently organic groups having 1-20 carbon atoms, or R$_1$ and R$_2$ are linked to form a ring structure with E;

R$_3$, R$_4$, R$_5$, R$_6$, R$_7$, R$_8$, R$_9$, R$_{10}$ and R$_{11}$ are independently —H or organic groups having 1-20 carbon atoms; or R$_1$/R$_3$ or R$_2$/R$_3$ forms a ring structure with the atoms to which they are attached and in this instance R$_4$/R$_5$, R$_5$/R$_6$, R$_7$/R$_8$, R$_8$/R$_9$, R$_9$/R$_{10}$ or R$_{10}$/R$_{11}$ may independently form a ring structure with the carbon atoms to which they are attached or R$_1$, R$_2$, R$_4$, R$_5$, R$_6$, R$_7$, R$_8$, R$_9$, R$_{10}$ and R$_{11}$ are as defined above; R$_{12}$ is an organic group having 1-20 carbon atoms;

m is 0, 1, 2, 3, 4 or 5;

E is P or As; and

X$^\ominus$ is a non-coordinated anionic ligand.

The palladium atom of the complex of formula (1) is formally cationic where the anion has been forced to the outer sphere of the metal centre.

When E is a phosphorus atom (i.e. P), the complex of formula (1) is a cationic palladium(II) complex comprising a biaryl tertiary phosphine ligand, a non-coordinated anionic ligand and an optionally substituted π-allyl group.

When E is an arsenic atom (i.e. As), the complex of formula (1) is a cationic palladium(II) complex comprising a biaryl tertiary arsine ligand, a non-coordinated anionic ligand and an optionally substituted π-allyl group.

Without wishing to be bound by theory, it is believed that the cationic Pd(II) complex has a distorted square planar structure of formula (2) comprising four ligands derived from the (R$_{12}$)$_m$-allyl, the phosphorus or arsenic atom of the ligand and a Pd—C interaction with the ipso-carbon of the non-phosphine- or non-arsine-containing aryl ring (illustrated in the drawing below by a dotted line). The cationic complexes of the present invention differ from π-allyl complexes comprising coordinated ligands (such as chloride ions) in that the ability of the non-coordinated anions to be forced away from the Pd-centre allows for the incorporation of extremely bulky biaryl/bi(hetero)aryl ligands, which stabilize the cationic Pd-centre through coordination of the non-phosphine- or non-arsine-containing aryl ring. This is in contrast to neutral complexes with coordinating anions which are too hindered to accommodate these extremely bulky ligands.

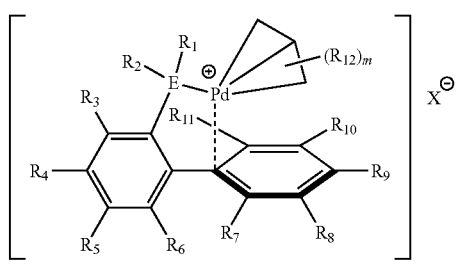

(2)

$R_1$ and $R_2$ may be the same or different. In one embodiment, $R_1$ and $R_2$ are the same. In another embodiment, $R_1$ and $R_2$ are different. $R_1$ and $R_2$ are selected up to the limitations imposed by stability and the rules of valence. $R_1$ and $R_2$ may be independently selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are independently selected from sulfur, nitrogen and oxygen. $R_1$ and $R_2$ may independently be substituted or unsubstituted branched- or straight-chain alkyl groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally substituted with one or more (e.g. 1, 2, 3, 4, or 5) substituents each of which may be the same or different such as halide (F, Cl, Br or I) or alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 4-dimethylaminophenyl, 4-methylphenyl, 3,5-dimethylphenyl, 4-methoxyphenyl, 4-methoxy-3,5-dimethylphenyl and 3,5-di(trifluoromethyl)phenyl. Substituted or unsubstituted heteroaryl groups such as pyridyl may also be used. In an alternative embodiment, $R_1$ and $R_2$ are linked to form a ring structure with E, preferably 4- to 7-membered rings. Preferably, $R_1$ and $R_2$ are the same and are tert-butyl, cyclohexyl, adamantyl, phenyl or substituted phenyl groups, such as 3,5-di(trifluoromethyl)phenyl.

$R_3$, $R_4$, $R_5$, $R_6$, $R_7$, $R_8$, $R_9$, $R_{10}$ and $R_{11}$ are independently —H or organic groups having 1-20 carbon atoms. $R_3$, $R_4$, $R_5$, $R_6$, $R_7$, $R_8$, $R_9$, $R_{10}$ and $R_{11}$ are selected up to the limitations imposed by stability and the rules of valence. $R_3$, $R_4$, $R_5$ and $R_6$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteroaryl or heterocycloalkyl groups may be independently selected from sulfur, nitrogen and/or oxygen. In one embodiment, the alkyl groups may be optionally substituted with one or more substituents (e.g. 1, 2, 3, 4, or 5) each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, —NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$OMe)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxyphenyl)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include but are not limited to $C_{4-8}$-heterocycloalkyl groups, such as piperidinyl and morpholinyl.

$R_3$, $R_4$, $R_5$ and $R_6$ may be independently selected from the group consisting of —H, unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different). Branched- or straight-chain alkyl groups may include groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl Cycloalkyl groups may include groups such as cyclopropyl, cyclobutyl, cyclopentyl, cyclohexyl or adamantyl. Alkoxy groups may include groups such as methoxy (—OMe), ethoxy (—OEt), n-propoxy (—O-n-Pr), iso-propoxy (—O-i-Pr), n-butoxy (—O-n-Bu), iso-butoxy (—O-i-Bu), sec-butoxy (—O-s-Bu), tert-butoxy (—O-t-Bu), —O-pentyl, —O-hexyl, —O-heptyl, —O-octyl, —O-nonyl, —O-decyl, —O-dodecyl. —N(alkyl)$_2$ groups may include groups such as —NMe$_2$, —NEt$_2$, —N(n-Pr)$_2$ or —N(i-Pr)$_2$.

$R_3$, $R_4$, $R_5$ and $R_6$ may be independently selected from the group consisting of —H, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

$R_3$, $R_4$, $R_5$ and $R_6$ may be independently selected from the group consisting of —H, unsubstituted straight-chain alkyl, unsubstituted branched-chain alkyl, unsubstituted cycloalkyl and unsubstituted alkoxy.

In one embodiment, each of $R_3$, $R_4$, $R_5$ and $R_6$ are —H.

In another embodiment, each of $R_3$, $R_4$, $R_5$ and $R_6$ are independently unsubstituted straight-chain alkyl groups, such as -Me.

In another embodiment, two of $R_3$, $R_4$, $R_5$ and $R_6$ are —H, and the other two of $R_3$, $R_4$, $R_5$ and $R_6$ are independently selected from the group consisting of unsubstituted straight-chain alkyl, unsubstituted branched-chain alkyl, unsubstituted cycloalkyl and unsubstituted alkoxy. In another embodiment, two of $R_3$, $R_4$, $R_5$ and $R_6$ are —H (e.g. $R_4$ and $R_5$), and the other two of $R_3$, $R_4$, $R_5$ and $R_6$ (e.g. $R_3$ and $R_6$) are independently selected from the group consisting of $C_{1-5}$-alkyl and —O—$C_{1-5}$-alkyl, such as -Me, -Et, —Pr (n- or i-), -Bu (n-, i- or t-), —OMe, —OEt, —OPr (n- or i-) and —OBu (n-, i- or t-), for example, -Me, -Et, —OMe and -OEt.

In another embodiment, two of $R_3$, $R_4$, $R_5$ and $R_6$ are —H (e.g. $R_4$ and $R_5$), and other two of $R_3$, $R_4$, $R_5$ and $R_6$ (e.g. $R_3$ and $R_6$) are selected from the group consisting of unsubstituted straight-chain alkyl, unsubstituted branched-chain alkyl, unsubstituted cycloalkyl and unsubstituted alkoxy. In a preferred embodiment, two of $R_3$, $R_4$, $R_5$ and $R_6$ are —H (e.g. $R_4$ and $R_5$), and the other two of $R_3$, $R_4$, $R_5$ and $R_6$ (e.g. $R_3$ and $R_6$) are selected from the group consisting of $C_{1-5}$-alkyl and —O—$C_{1-5}$-alkyl, such as -Me, -Et, —Pr (n- or i-), -Bu (n-, i- or t-), —OMe, —OEt, —OPr (n- or i-) and —OBu (n-, i- or t-), for example, -Me, -Et, —OMe and -OEt. In a particularly preferred embodiment, $R_4$ and $R_5$ are —H, and $R_3$ and $R_6$ are —OMe. In another particularly preferred embodiment, $R_4$ and $R_5$ are —H, and $R_3$ and $R_6$ are selected from the group consisting of -Me and —OMe, for example, $R_3$ may be —OMe and $R_6$ may be -Me.

$R_7$, $R_8$, $R_9$, $R_{10}$ and $R_{11}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteroaryl or heterocycloalkyl groups may be independently selected from sulfur, nitrogen and/or oxygen. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, —NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$OMe)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxyphenyl)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include $C_{4-8}$-heterocycloalkyl groups, such as piperidinyl and morpholinyl.

$R_7$, $R_8$, $R_9$, $R_{10}$ and $R_{11}$ may be independently selected from the group consisting of —H, unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different). Branched- or straight-chain alkyl groups may include groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl Cycloalkyl groups may include groups such as cyclopropyl, cyclobutyl, cyclopentyl, cyclohexyl or adamantyl. Alkoxy groups may include groups such as methoxy (—OMe), ethoxy (—OEt), n-propoxy (—O-n-Pr), iso-propoxy (—O-i-Pr), n-butoxy (—O-n-Bu), iso-butoxy (—O-i-Bu), sec-butoxy (—O-s-Bu), tert-butoxy (—O-t-Bu), —O-pentyl, —O-hexyl, —O-heptyl, —O-octyl, —O-nonyl, —O-decyl, —O-dodecyl. —N(alkyl)$_2$ groups may include groups such as —NMe$_2$, —NEt$_2$, —N(n-Pr)$_2$ or —N(i-Pr)$_2$.

$R_7$, $R_8$, $R_9$, $R_{10}$ and $R_{11}$ may be independently selected from the group consisting of —H, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

$R_7$, $R_8$, $R_9$, $R_{10}$ and $R_{11}$ may be independently selected from the group consisting of —H, unsubstituted straight-chain alkyl, unsubstituted branched-chain alkyl, unsubstituted cycloalkyl and unsubstituted alkoxy.

In one embodiment, each of $R_7$, $R_8$, $R_9$, $R_{10}$ and $R_{11}$ are —H.

In another embodiment, four of $R_7$, $R_8$, $R_9$, $R_{10}$ and $R_{11}$ are —H (e.g. $R_8$, $R_9$, $R_{10}$ and $R_{11}$), and the other one of $R_7$, $R_8$, $R_9$, $R_{10}$ and $R_{11}$ (e.g. $R_7$) is selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, four of $R_7$, $R_8$, $R_9$, $R_{10}$ and $R_{11}$ are —H (e.g. $R_8$, $R_9$, $R_{10}$ and $R_{11}$), and the other one of $R_7$, $R_8$, $R_9$, $R_{10}$ and $R_{11}$ (e.g. $R_7$) is selected from the group consisting of $C_{1-5}$-alkyl, —O—$C_{1-5}$-alkyl and —N($C_{1-5}$-alkyl)$_2$ such as -Me, -Et, —Pr (n- or i-), -Bu (n-, i- or t-), —OMe, —OEt, —OPr (n- or i-), —OBu (n-, i- or t-), —NMe$_2$, —NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, —NEt$_2$. For example, $R_8$, $R_9$, $R_{10}$ and $R_{11}$ are —H, and $R_7$ is selected from $C_{1-5}$-alkyl, —O—$C_{1-5}$-alkyl and —N($C_{1-5}$-alkyl)$_2$ groups, such as those described above. In another embodiment, $R_8$, $R_9$, $R_{10}$ and $R_{11}$ are —H, and $R_7$ is selected from the group consisting of —OMe, —O-i-Pr, —NMe$_2$, —NEt$_2$, —N(n-Pr)$_2$ and —N(i-Pr)$_2$, such as —OMe and —NMe$_2$.

In another embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In one embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are selected from the group consisting of unsubstituted straight-chain alkyl, unsubstituted branched-chain alkyl, unsubstituted cycloalkyl, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are independently selected from the group consisting of $C_{1-5}$-alkyl, —O—$C_{1-5}$-alkyl and —N($C_{1-5}$-alkyl)$_2$ such as -Me, -Et, —Pr (n- or i-), -Bu (n-, i- or t-), —OMe, -OEt, —OPr (n- or i-), —OBu (n-, i- or t-), —NMe$_2$, —NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, —NEt$_2$. For example, $R_8$, $R_9$ and $R_{10}$ are —H, and $R_7$ and $R_{11}$ are independently selected from $C_{1-5}$-alkyl, —O—$C_{1-5}$-alkyl and —N($C_{1-5}$-alkyl)$_2$ groups, such as those described above. In another embodiment, $R_8$, $R_9$ and $R_{10}$ are —H, and $R_7$ and $R_{11}$ are independently selected from the group consisting of —OMe, —O-i-Pr, —NMe$_2$, —NEt$_2$, —N(n-Pr)$_2$ and —N(i-Pr)$_2$, such as —OMe and —O-i-Pr.

In a preferred embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are selected from the group consisting of $C_{1-5}$-alkyl, —O—$C_{1-5}$-alkyl and —N($C_{1-5}$-alkyl)$_2$ such as -Me, -Et, —Pr (n- or i-), -Bu (n-, i- or t-), —OMe, —OEt, —OPr (n- or i-), —OBu (n-, i- or t-), —NMe$_2$, —NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, —NEt$_2$. In a particularly preferred embodiment, $R_8$, $R_9$ and $R_{10}$ are —H, and $R_7$, and $R_{11}$ are independently selected from $C_{1-5}$-alkyl, —O—$C_{1-5}$-alkyl and —N($C_{1-5}$-alkyl)$_2$ groups, such as those described above. In an especially preferred embodiment, $R_8$, $R_9$ and $R_{10}$ are —H, and $R_7$ and $R_{11}$ are selected from the group consisting of —OMe, —O-i-Pr, —NMe$_2$, —NEt$_2$, —N(n-Pr)$_2$ or —N(i-Pr)$_2$, such as —OMe and —O-i-Pr.

In another embodiment, two of $R_7$, $R_8$, $R_9$, $R_{10}$ and $R_{11}$ are —H (e.g. $R_8$ and $R_{10}$), and the other three of $R_7$, $R_8$, $R_9$, $R_{10}$ and $R_{11}$ (e.g. $R_7$, $R_9$ and $R_{11}$) are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, two of $R_7$, $R_8$, $R_9$, $R_{10}$ and $R_{11}$ are —H (e.g. $R_8$ and $R_{10}$), and the other three of $R_7$, $R_8$, $R_9$, $R_{10}$ and $R_{11}$ (e.g. $R_7$, $R_9$ and $R_{11}$) are selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In one preferred embodiment, two of $R_7$, $R_8$, $R_9$, $R_{10}$ and $R_{11}$ are —H (e.g. $R_8$ and $R_{10}$), and the other three of $R_7$, $R_8$, $R_9$, $R_{10}$ and $R_{11}$ (e.g. $R_7$, $R_9$ and $R_{11}$) are independently selected from the group consisting of $C_{1-5}$-alkyl, —O—$C_{1-5}$-alkyl and —N($C_{1-5}$-alkyl)$_2$, such as -Me, -Et, —Pr (n- or i-), -Bu (n-, i- or t-), —OMe, —OEt, —OPr (n- or i-), —OBu (n-, i- or t-), —NMe$_2$, —NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, —NEt$_2$. In a particularly preferred embodiment, $R_8$ and $R_{10}$ are —H, and $R_7$, $R_9$ and $R_{11}$ are independently selected from —$C_{1-5}$-alkyl groups, such as those described above.

In another preferred embodiment, two of $R_7$, $R_8$, $R_9$, $R_{10}$ and $R_{11}$ are —H (e.g. $R_8$ and $R_{10}$), and the other three of $R_7$, $R_8$, $R_9$, $R_{10}$ and $R_{11}$ (e.g. $R_7$, $R_9$ and $R_{11}$) are selected from the group consisting of $C_{1-5}$-alkyl, —O—$C_{1-5}$-alkyl and —N($C_{1-5}$-alkyl)$_2$, such as -Me, -Et, —Pr (n- or i-), -Bu (n-, i- or t-), —OMe, -OEt, —OPr (n- or i-), —OBu (n-, i- or t-), —NMe$_2$, —NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, —NEt$_2$. In a particularly preferred embodiment, $R_8$ and $R_{10}$ are —H, and $R_7$, $R_9$ and $R_{11}$ are independently selected from —$C_{1-5}$-alkyl groups, such as those described above. In an especially preferred embodiment, $R_8$ and $R_{10}$ are —H, and $R_7$, $R_9$ and $R_{11}$ are -i-Pr.

In one embodiment, the monodentate tertiary phosphine ligand is selected from the group consisting of:

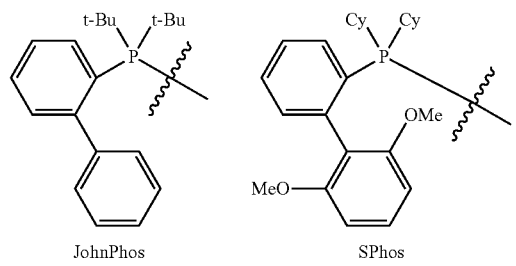

JohnPhos    SPhos

15
-continued

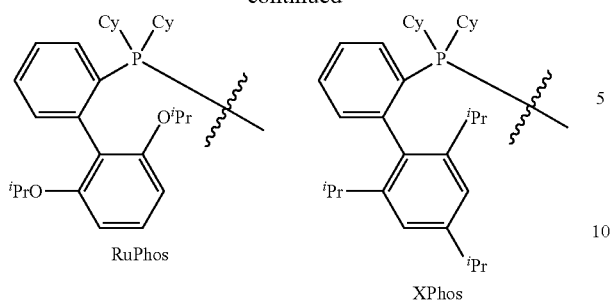

RuPhos

XPhos

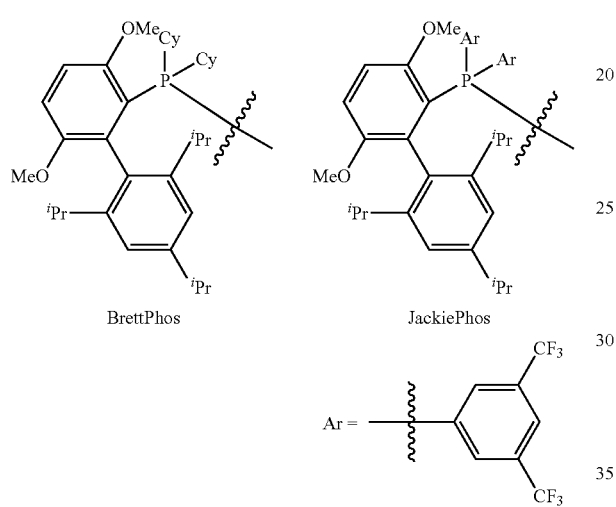

BrettPhos

JackiePhos

Ar =

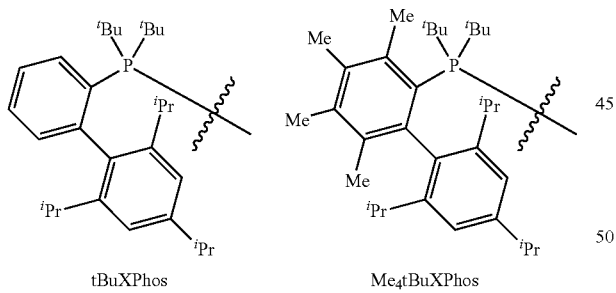

tBuXPhos

Me₄tBuXPhos

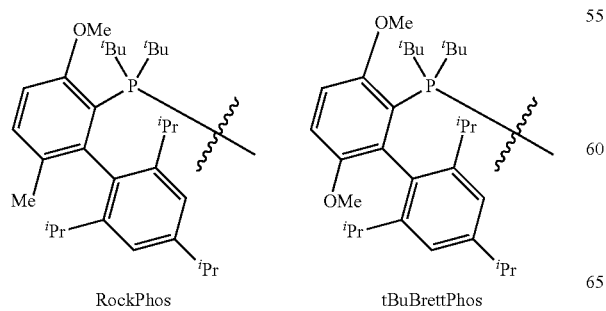

RockPhos tBuBrettPhos

16
-continued

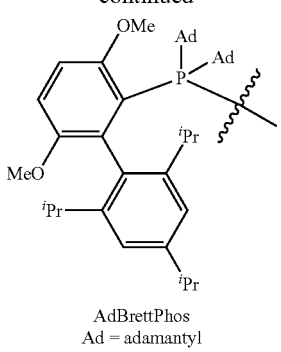

AdBrettPhos
Ad = adamantyl

In a preferred embodiment, the cationic complex of the present invention comprises an extremely bulky ligand, such as a monodentate tertiary phosphine ligand selected from the group consisting of:

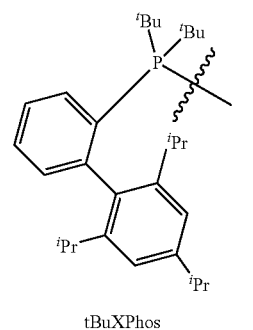

tBuXPhos

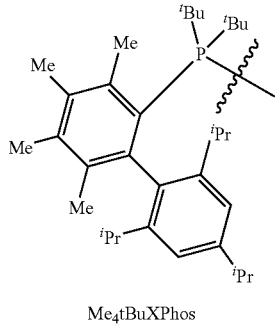

Me₄tBuXPhos

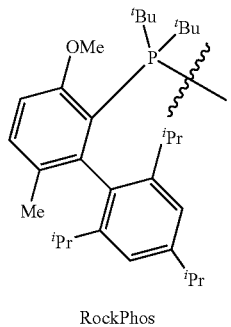

RockPhos

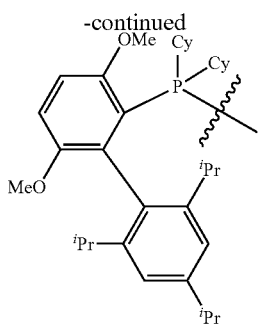

BrettPhos

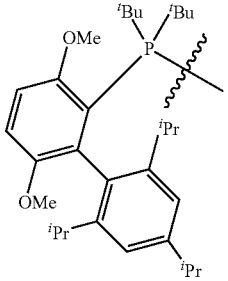

tBuBrettPhos

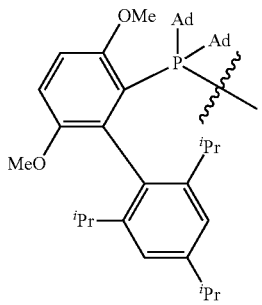

AdBrettPhos

In this embodiment, it has been found that π-allyl complexes comprising coordinating anions and one of tBuX-Phos, Me$_4$tBuXPhos, tBuBrettPhos, RockPhos or AdBrettPhos cannot be typically made. The optionally substituted cationic π-allyl complexes of the present invention, therefore, are generally more accessible than those with coordinating anions as the non-coordinated anion reduces the steric congestion around the Pd cation allowing the Pd cation to bind to the ligand.

$R_1/R_3$ or $R_2/R_3$ may form a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above. The pair or pairs are selected up to the limitations imposed by stability and the rules of valence.

The linking group for $R_1/R_3$ or $R_2/R_3$ may be a substituted or unsubstituted alkyl, substituted or unsubstituted alkoxy, or substituted or unsubstituted heteroalkyl. The ring structure formed from the pair or pairs selected from the group consisting of $R_4/R_5$, $R_5/R_6$, $R_7/R_8$, $R_8/R_9$, $R_9/R_{10}$ and $R_{10}/R_{11}$ may be a substituted or unsubstituted cycloalkyl, substituted or unsubstituted heterocycloalkyl, substituted or unsubstituted aryl or substituted or unsubstituted heteroaryl group. $R_1$ and $R_2$ may be independently selected from the groups defined above when they do not form a ring structure with $R_3$.

In one embodiment, $R_4$, $R_5$ and $R_6$ are —H and the pair $R_1/R_3$ or $R_2/R_3$ forms a ring structure with the atoms to which they are attached. In another embodiment, $R_4$, $R_5$ and $R_6$ are —H and the pair $R_1/R_3$ or $R_2/R_3$ forms a ring structure with the atoms to which they are attached. In either of these instances, $R_7/R_8$, $R_8/R_9$, $R_9/R_{10}$ or $R_{10}/R_{11}$ may independently form a ring structure with the carbon atoms to which they are attached or $R_7$, $R_8$, $R_9$, $R_{10}$ and $R_{11}$ are as defined above. $R_1/R_3$ or $R_2/R_3$ may form a ring structure selected from the group consisting of:

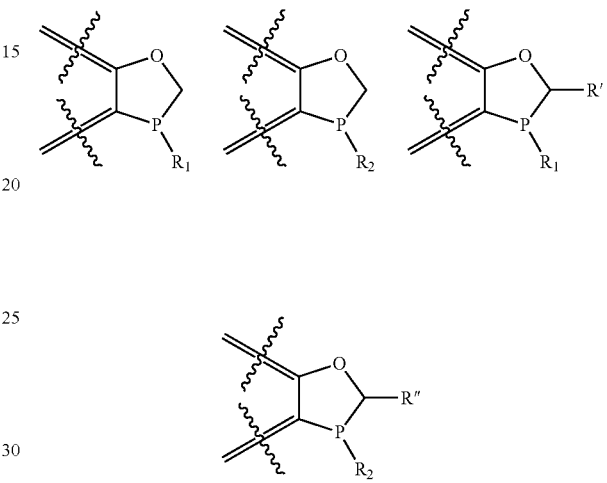

wherein:

$R_1$ and $R_2$ are as defined above: and

R' and R" are independently as defined above for $R_1$ and $R_2$.

In one embodiment, R' and R" are independently selected from the group consisting of methyl, propyl (n- or i-), butyl (n-, i- or t-), cyclohexyl or phenyl.

Examples of phosphorus ligands include those described by Tang et al, Angew. Chem. Int. Ed. 2010, 49, 5879-5883, Zhao et al, Chem. Eur. J, 2013, 19(7), 2261-2265 and Xu et al, Journal of the American Chemical Society, 2014, 136(2), 570-573 such as:

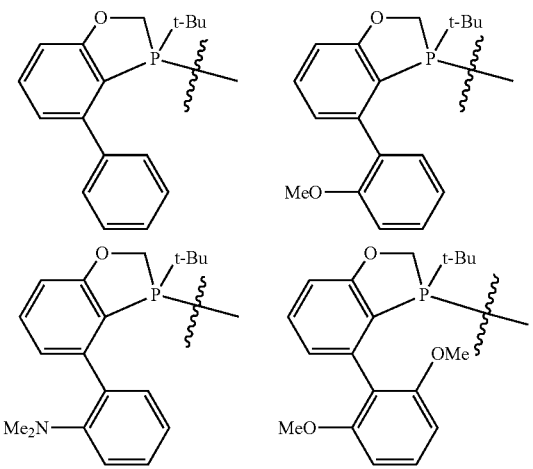

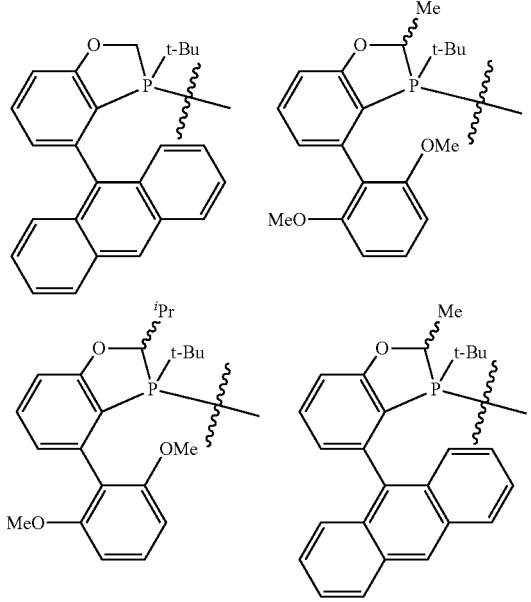

It will be understood that, in the depictions herein, where -Me or -$^i$Pr is connected by a wavy line ($\sim$), either stereoisomer may be present.

The Pd cation in the complex of formula (1) is coordinated to an optionally substituted allyl group. $R_{12}$ is an organic group having 1-20 carbon atoms, preferably 1-10 carbon atoms and more preferably 1-8 carbon atoms. $R_{12}$ is selected up to the limitations imposed by stability and the rules of valence. The number of $R_{12}$ groups ranges from 0 to 5 i.e. m is 0, 1, 2, 3, 4 or 5. When m is 2, 3, 4 or 5, each of $R_{12}$ may be the same or different. In certain embodiments, when m is 2, 3, 4, or 5, each $R_{12}$ is the same. In certain embodiments, m is 0 i.e. the allyl group is unsubstituted. In certain embodiments, m is 1. In certain embodiments, m is 2, wherein each $R_{12}$ is the same or different.

$R_{12}$ may be selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are independently selected from sulfur, nitrogen and oxygen. In one embodiment, $R_{12}$ is selected from the group consisting of substituted and unsubstituted straight-chain alkyl, substituted and unsubstituted branched-chain alkyl, and substituted and unsubstituted cycloalkyl. In another embodiment, $R_{12}$ is selected from the group consisting of substituted and unsubstituted aryl, and substituted and unsubstituted heteroaryl wherein the heteroatoms are independently selected from sulfur, nitrogen and oxygen. $R_{12}$ may be substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl or aryl groups such as phenyl, naphthyl or anthracyl. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. In one embodiment, each $R_{12}$ is independently a methyl, phenyl or substituted phenyl group.

Suitable optionally substituted allyl groups as coordinated to the Pd atom are shown below:

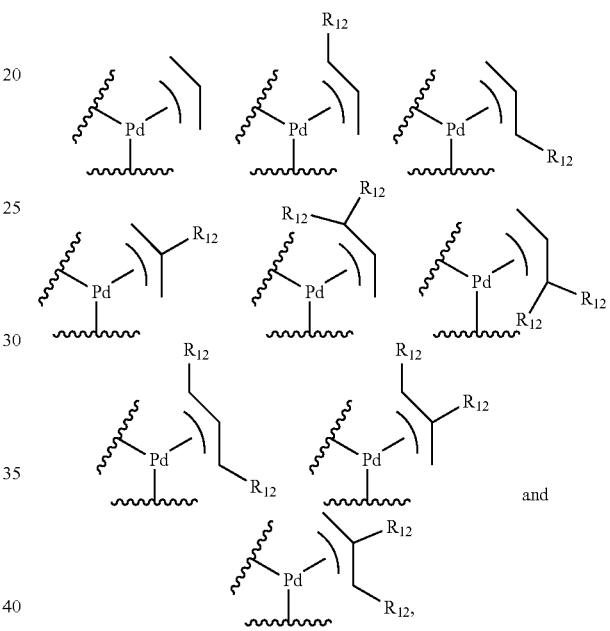

such as

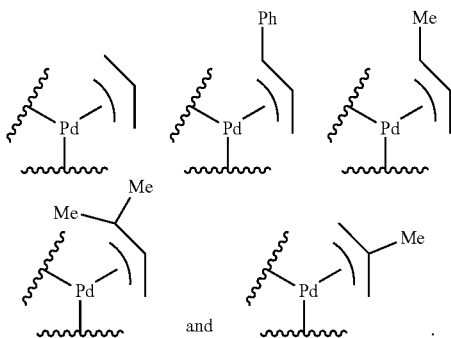

In the complex of formula (1), X is a non-coordinated anionic ligand. By "non-coordinated anion ligand", we mean the anionic ligand is forced to the outer sphere of the metal centre. The anionic ligand, therefore, is dissociated from the metal centre. This is in contrast to neutral complexes in which the anionic ligand is bound to the metal within the coordination sphere. The anionic ligand can be generally identified as non-coordinating by analysing the X-ray crystal structure of the cationic complex. In one embodiment, $X^\ominus$ is selected from the group consisting of triflate (i.e. TfO⁻ or $CF_3SO_3^-$), tetrafluoroborate (i.e. ⁻$BF_4$), hexafluoroantimonate (i.e. ⁻$SbF_6$), hexafluorophosphate ($PF_6^-$), [B[3,5-$(CF_3)_2C_6H_3]_4$]⁻ ([Bar$^F_4$]⁻) and mesylate (MsO⁻ or $MeSO_3^-$).

The complex of formula (1) may be selected from the group consisting of:

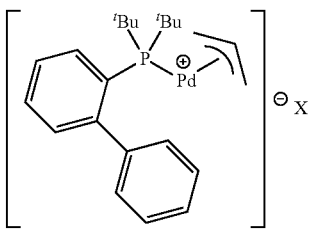

[(π-allyl)Pd(JohnPhos)]X

X = ⁻OTf: [(π-allyl)Pd(JohnPhos)]OTf;
X = ⁻PF₆: [(π-allyl)Pd(JohnPhos)]PF₆;
X = ⁻BF₄: [(π-allyl)Pd(JohnPhos)]BF₄;
X = ⁻SbF₆: [(π-allyl)Pd(JohnPhos)]SbF₆;
X = [BAr$^F_4$]⁻: [(π-allyl)Pd(JohnPhos)][BAr$^F_4$];
X = ⁻OMs: [(π-allyl)Pd(JohnPhos)]OMs

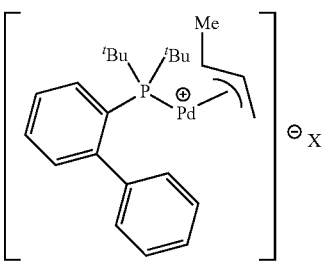

[(π-crotyl)Pd(JohnPhos)]X

X = ⁻OTf: [(π-crotyl)Pd(JohnPhos)]OTf;
X = ⁻PF₆: [(π-crotyl)Pd(JohnPhos)]PF₆;
X = ⁻BF₄: [(π-crotyl)Pd(JohnPhos)]BF₄;
X = ⁻SbF₆: [(π-crotyl)Pd(JohnPhos)]SbF₆;
X = [BAr$^F_4$]⁻: [(π-crotyl)Pd(JohnPhos)][BAr$^F_4$];
X = ⁻OMs: [(π-crotyl)Pd(JohnPhos)]OMs

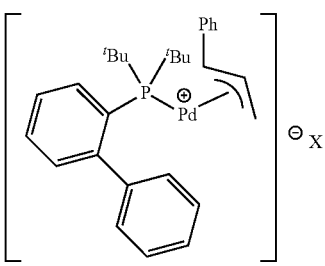

[(π-cinnamyl)Pd(JohnPhos)]X

X = ⁻OTf: [(π-cinnamyl)Pd(JohnPhos)]OTf;
X = ⁻PF₆: [(π-cinnamyl)Pd(JohnPhos)]PF₆;
X = ⁻BF₄: [(π-cinnamyl)Pd(JohnPhos)]BF₄;
X = ⁻SbF₆: [(π-cinnamyl)Pd(JohnPhos)]SbF₆;
X = [BAr$^F_4$]⁻: [(π-cinnamyl)Pd(JohnPhos)][BAr$^F_4$];
X = ⁻OMs: [(π-cinnamyl)Pd(JohnPhos)]OMs -continued

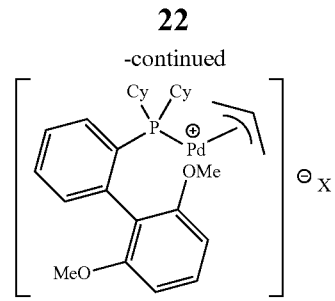

[(π-allyl)Pd(SPhos)]X

X = ⁻OTf: [(π-allyl)Pd(SPhos)]OTf;
X = ⁻PF₆: [(π-allyl)Pd(SPhos)]PF₆;
X = ⁻BF₄: [(π-allyl)Pd(SPhos)]BF₄;
X = ⁻SbF₆: [(π-allyl)Pd(SPhos)]SbF₆;
X = [BAr$^F_4$]⁻: [(π-allyl)Pd(SPhos)][BAr$^F_4$];
X = ⁻OMs: [(π-allyl)Pd(SPhos)]OMs

[(π-crotyl)Pd(SPhos)]X

X = ⁻OTf: [(π-crotyl)Pd(SPhos)]OTf;
X = ⁻PF₆: [(π-crotyl)Pd(SPhos)]PF₆;
X = ⁻BF₄: [(π-crotyl)Pd(SPhos)]BF₄;
X = ⁻SbF₆: [(π-crotyl)Pd(SPhos)]SbF₆;
X = [BAr$^F_4$]⁻: [(π-crotyl)Pd(SPhos)][BAr$^F_4$];
X = ⁻OMs: [(π-crotyl)Pd(SPhos)]OMs

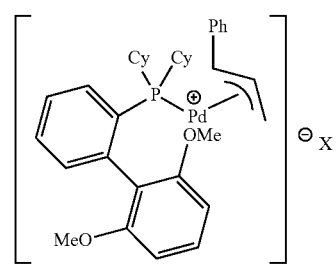

[(π-cinnamyl)Pd(SPhos)]X

X = ⁻OTf: [(π-cinnamyl)Pd(SPhos)]OTf;
X = ⁻PF₆: [(π-cinnamyl)Pd(SPhos)]PF₆;
X = ⁻BF₄: [(π-cinnamyl)Pd(SPhos)]BF₄;
X = ⁻SbF₆: [(π-cinnamyl)Pd(SPhos)]SbF₆;
X = [BAr$^F_4$]⁻: [(π-cinnamyl)Pd(SPhos)][BAr$^F_4$];
X = ⁻OMs: [(π-cinnamyl)Pd(SPhos)]OMs -continued

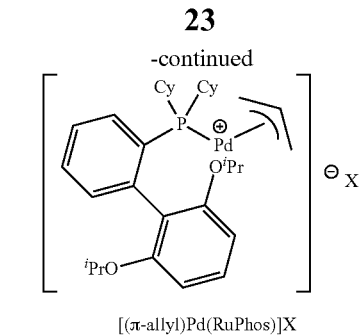

[(π-allyl)Pd(RuPhos)]X

X = ⁻OTf: [(π-allyl)Pd(RuPhos)]OTf;
X = ⁻PF₆: [(π-allyl)Pd(RuPhos)]PF₆;
X = ⁻BF₄: [(π-allyl)Pd(RuPhos)]BF₄;
X = ⁻SbF₆: [(π-allyl)Pd(RuPhos)]SbF₆;
X = [BAr$^F_4$]⁻: [(π-allyl)Pd(RuPhos)][BAr$^F_4$];
X = ⁻OMs: [(π-allyl)Pd(RuPhos)]OMs

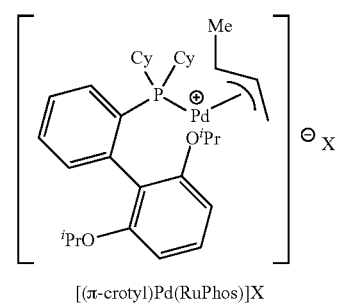

[(π-crotyl)Pd(RuPhos)]X

X = ⁻OTf: [(π-crotyl)Pd(RuPhos)]OTf;
X = ⁻PF₆: [(π-crotyl)Pd(RuPhos)]PF₆;
X = ⁻BF₄: [(π-crotyl)Pd(RuPhos)]BF₄;
X = ⁻SbF₆: [(π-crotyl)Pd(RuPhos)]SbF₆;
X = [BAr$^F_4$]⁻: [(π-crotyl)Pd(RuPhos)][BAr$^F_4$];
X = ⁻OMs: [(π-crotyl)Pd(RuPhos)]OMs

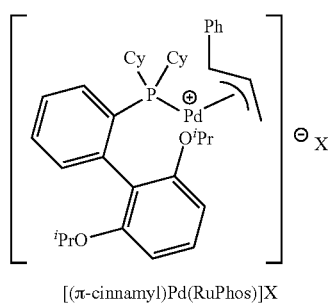

[(π-cinnamyl)Pd(RuPhos)]X

X = ⁻OTf: [(π-cinnamyl)Pd(RuPhos)]OTf;
X = ⁻PF₆: [(π-cinnamyl)Pd(RuPhos)]PF₆;
X = ⁻BF₄: [(π-cinnamyl)Pd(RuPhos)]BF₄;
X = ⁻SbF₆: [(π-cinnamyl)Pd(RuPhos)]SbF₆;
X = [BAr$^F_4$]⁻: [(π-cinnamyl)Pd(RuPhos)][BAr$^F_4$];
X = ⁻OMs: [(π-cinnamyl)Pd(RuPhos)]OMs -continued

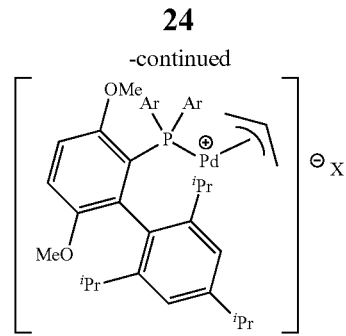

[(π-allyl)Pd(JackiePhos)]X

X = ⁻OTf: [(π-allyl)Pd(JackiePhos)]OTf;
X = ⁻PF₆: [(π-allyl)Pd(JackiePhos)]PF₆;
X = ⁻BF₄: [(π-allyl)Pd(JackiePhos)]BF₄;
X = ⁻SbF₆: [(π-allyl)Pd(JackiePhos)]SbF₆;
X = [BAr$^F_4$]⁻: [(π-allyl)Pd(JackiePhos)][BAr$^F_4$];
X = ⁻OMs: [(π-allyl)Pd(JackiePhos)]OMs

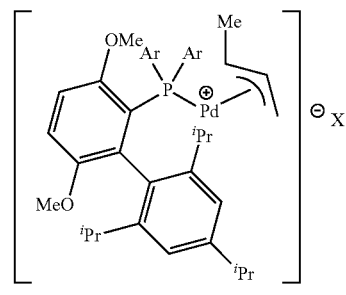

[(π-crotyl)Pd(JackiePhos)]X

X = ⁻OTf: [(π-crotyl)Pd(JackiePhos)]OTf;
X = ⁻PF₆: [(π-crotyl)Pd(JackiePhos)]PF₆;
X = ⁻BF₄: [(π-crotyl)Pd(JackiePhos)]BF₄;
X = ⁻SbF₆: [(π-crotyl)Pd(JackiePhos)]SbF₆;
X = [BAr$^F_4$]⁻: [(π-crotyl)Pd(JackiePhos)][BAr$^F_4$];
X = ⁻OMs: [(π-crotyl)Pd(JackiePhos)]OMs

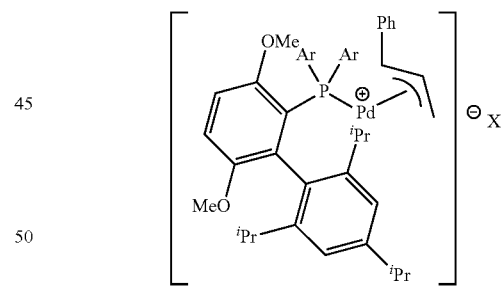

[(π-cinnamyl)Pd(JackiePhos)]X

X = ⁻OTf: [(π-cinnamyl)Pd(JackiePhos)]OTf;
X = ⁻PF₆: [(π-cinnamyl)Pd(JackiePhos)]PF₆;
X = ⁻BF₄: [(π-cinnamyl)Pd(JackiePhos)]BF₄;
X = ⁻SbF₆: [(π-cinnamyl)Pd(JackiePhos)]SbF₆;
X = [BAr$^F_4$]⁻: [(π-cinnamyl)Pd(JackiePhos)][BAr$^F_4$];
X = ⁻OMs: [(π-cinnamyl)Pd(JackiePhos)]OMs

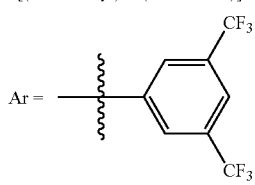

-continued

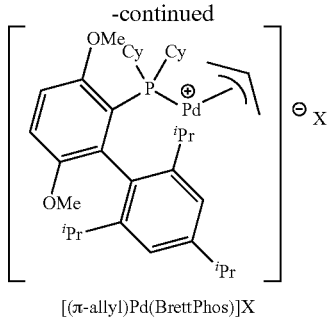

[(π-allyl)Pd(BrettPhos)]X

X = ⁻OTf: [(π-allyl)Pd(BrettPhos)]OTf;
X = ⁻PF₆: [(π-allyl)Pd(BrettPhos)]PF₆;
X = ⁻BF₄: [(π-allyl)Pd(BrettPhos)]BF₄;
X = ⁻SbF₆: [(π-allyl)Pd(BrettPhos)]SbF₆;
X = [BAr$^F_4$]⁻: [(π-allyl)Pd(BrettPhos)][BAr$^F_4$];
X = ⁻OMs: [(π-allyl)Pd(BrettPhos)]OMs

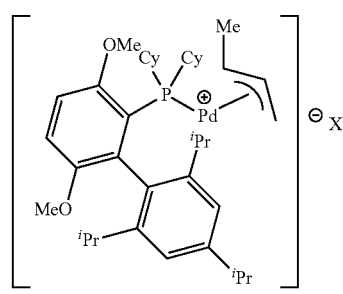

[(π-crotyl)Pd(BrettPhos)]X

X = ⁻OTf: [(π-crotyl)Pd(BrettPhos)]OTf;
X = ⁻PF₆: [(π-crotyl)Pd(BrettPhos)]PF₆;
X = ⁻BF₄: [(π-crotyl)Pd(BrettPhos)]BF₄;
X = ⁻SbF₆: [(π-crotyl)Pd(BrettPhos)]SbF₆;
X = [BAr$^F_4$]⁻: [(π-crotyl)Pd(BrettPhos)][BAr$^F_4$];
X = ⁻OMs: [(π-crotyl)Pd(BrettPhos)]OMs

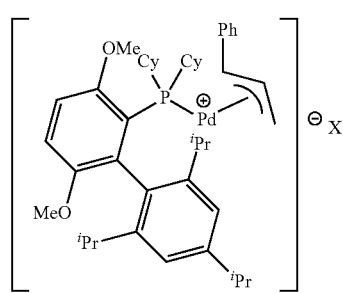

[(π-cinnamyl)Pd(BrettPhos)]X

X = ⁻OTf: [(π-cinnamyl)Pd(BrettPhos)]OTf;
X = ⁻PF₆: [(π-cinnamyl)Pd(BrettPhos)]PF₆;
X = ⁻BF₄: [(π-cinnamyl)Pd(BrettPhos)]BF₄;
X = ⁻SbF₆: [(π-cinnamyl)Pd(BrettPhos)]SbF₆;
X = [BAr$^F_4$]⁻: [(π-cinnamyl)Pd(BrettPhos)][BAr$^F_4$];
X = ⁻OMs: [(π-cinnamyl)Pd(BrettPhos)]OMs -continued

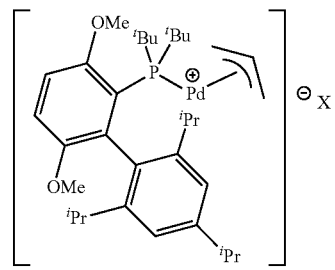

[(π-allyl)Pd(tBuBrettPhos)]X

X = ⁻OTf: [(π-allyl)Pd(tBuBrettPhos)]OTf;
X = ⁻PF₆: [(π-allyl)Pd(tBuBrettPhos)]PF₆;
X = ⁻BF₄: [(π-allyl)Pd(tBuBrettPhos)]BF₄;
X = ⁻SbF₆: [(π-allyl)Pd(tBuBrettPhos)]SbF₆;
X = [BAr$^F_4$]⁻: [(π-allyl)Pd(tBuBrettPhos)][BAr$^F_4$];
X = ⁻OMs: [(π-allyl)Pd(tBuBrettPhos)]OMs

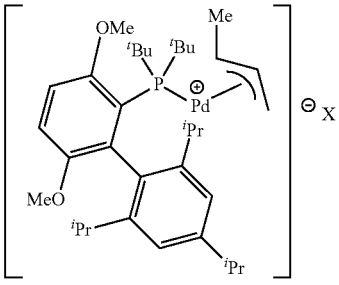

[(π-crotyl)Pd(tBuBrettPhos)]X

X = ⁻OTf: [(π-crotyl)Pd(tBuBrettPhos)]OTf;
X = ⁻PF₆: [(π-crotyl)Pd(tBuBrettPhos)]PF₆;
X = ⁻BF₄: [(π-crotyl)Pd(tBuBrettPhos)]BF₄;
X = ⁻SbF₆: [(π-crotyl)Pd(tBuBrettPhos)]SbF₆;
X = [BAr$^F_4$]⁻: [(π-crotyl)Pd(tBuBrettPhos)][BAr$^F_4$];
X = ⁻OMs: [(π-crotyl)Pd(tBuBrettPhos)]OMs

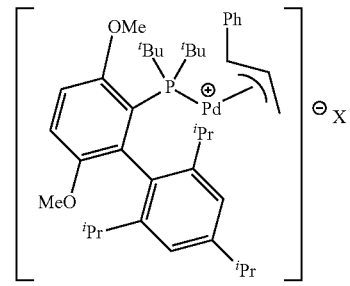

[(π-cinnamyl)Pd(tBuBrettPhos)]X

X = ⁻OTf: [(π-cinnamyl)Pd(tBuBrettPhos)]OTf;
X = ⁻PF₆: [(π-cinnamyl)Pd(tBuBrettPhos)]PF₆;
X = ⁻BF₄: [(π-cinnamyl)Pd(tBuBrettPhos)]BF₄;
X = ⁻SbF₆: [(π-cinnamyl)Pd(tBuBrettPhos)]SbF₆;
X = [BAr$^F_4$]⁻: [(π-cinnamyl)Pd(tBuBrettPhos)][BAr$^F_4$];
X = ⁻OMs: [(π-cinnamyl)Pd(tBuBrettPhos)]OMs

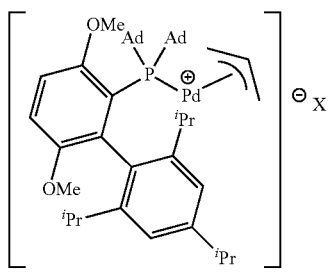

[(π-allyl)Pd(AdBrettPhos)]X

X = ⁻OTf: [(π-allyl)Pd(AdBrettPhos)]OTf;
X = ⁻PF$_6$: [(π-allyl)Pd(AdBrettPhos)]PF$_6$;
X = ⁻BF$_4$: [(π-allyl)Pd(AdBrettPhos)]BF$_4$;
X = ⁻SbF$_6$: [(π-allyl)Pd(AdBrettPhos)]SbF$_6$;
X = [BAr$^F_4$]⁻: [(π-allyl)Pd(AdBrettPhos)][BAr$^F_4$];
X = ⁻OMs: [(π-allyl)Pd(AdBrettPhos)]OMs

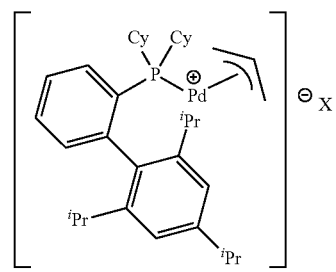

[(π-allyl)Pd(XPhos)]X

X = ⁻OTf: [(π-allyl)Pd(XPhos)]OTf;
X = ⁻PF$_6$: [(π-allyl)Pd(XPhos)]PF$_6$;
X = ⁻BF$_4$: [(π-allyl)Pd(XPhos)]BF$_4$;
X = ⁻SbF$_6$: [(π-allyl)Pd(XPhos)]SbF$_6$;
X = [BAr$^F_4$]⁻: [(π-allyl)Pd(XPhos)][BAr$^F_4$];
X = ⁻OMs: [(π-allyl)Pd(XPhos)]OMs

[(π-crotyl)Pd(AdBrettPhos)]X

X = ⁻OTf: [(π-crotyl)Pd(AdBrettPhos)]OTf;
X = ⁻PF$_6$: [(π-crotyl)Pd(AdBrettPhos)]PF$_6$;
X = ⁻BF$_4$: [(π-crotyl)Pd(AdBrettPhos)]BF$_4$;
X = ⁻SbF$_6$: [(π-crotyl)Pd(AdBrettPhos)]SbF$_6$;
X = [BAr$^F_4$]⁻: [(π-crotyl)Pd(AdBrettPhos)][BAr$^F_4$];
X = ⁻OMs: [(π-crotyl)Pd(AdBrettPhos)]OMs

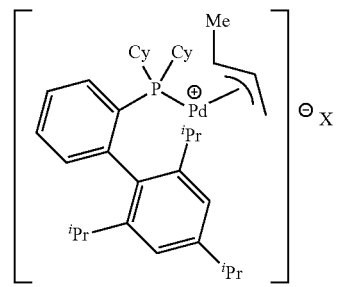

[(π-crotyl)Pd(XPhos)]X

X = ⁻OTf: [(π-crotyl)Pd(XPhos)]OTf;
X = ⁻PF$_6$: [(π-crotyl)Pd(XPhos)]PF$_6$;
X = ⁻BF$_4$: [(π-crotyl)Pd(XPhos)]BF$_4$;
X = ⁻SbF$_6$: [(π-crotyl)Pd(XPhos)]SbF$_6$;
X = [BAr$^F_4$]⁻: [(π-crotyl)Pd(XPhos)][BAr$^F_4$];
X = ⁻OMs: [(π-crotyl)Pd(XPhos)]OMs

[(π-cinnamyl)Pd(AdBrettPhos)]X

X = ⁻OTf: [(π-cinnamyl)Pd(AdBrettPhos)]OTf;
X = ⁻PF$_6$: [(π-cinnamyl)Pd(AdBrettPhos)]PF$_6$;
X = ⁻BF$_4$: [(π-cinnamyl)Pd(AdBrettPhos)]BF$_4$;
X = ⁻SbF$_6$: [(π-cinnamyl)Pd(AdBrettPhos)]SbF$_6$;
X = [BAr$^F_4$]⁻: [(π-cinnamyl)Pd(AdBrettPhos)][BAr$^F_4$];
X = ⁻OMs: [(π-cinnamyl)Pd(AdBrettPhos)]OMs

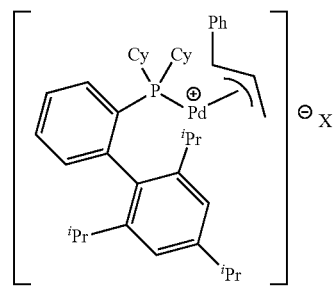

[(π-cinnamyl)Pd(XPhos)]X

X = ⁻OTf: [(π-cinnamyl)Pd(XPhos)]OTf;
X = ⁻PF$_6$: [(π-cinnamyl)Pd(XPhos)]PF$_6$;
X = ⁻BF$_4$: [(π-cinnamyl)Pd(XPhos)]BF$_4$;
X = ⁻SbF$_6$: [(π-cinnamyl)Pd(XPhos)]SbF$_6$;
X = [BAr$^F_4$]⁻: [(π-cinnamyl)Pd(XPhos)][BAr$^F_4$];
X = ⁻OMs: [(π-cinnamyl)Pd(XPhos)]OMs -continued

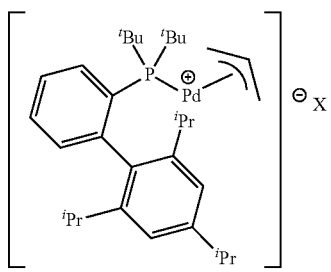

[(π-allyl)Pd(tBuXPhos)]X

X = ⁻OTf: [(π-allyl)Pd(tBuXPhos)]OTf;
X = ⁻PF$_6$: [(π-allyl)Pd(tBuXPhos)]PF$_6$;
X = ⁻BF$_4$: [(π-allyl)Pd(tBuXPhos)]BF$_4$;
X = ⁻SbF$_6$: [(π-allyl)Pd(tBuXPhos)]SbF$_6$;
X = [BAr$^F_4$]⁻: [(π-allyl)Pd(tBuXPhos)][BAr$^F_4$];
X = ⁻OMs: [(π-allyl)Pd(tBuXPhos)]OMs

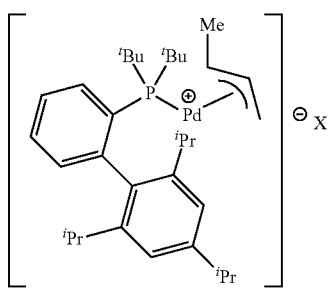

[(π-crotyl)Pd(tBuXPhos)]X

X = ⁻OTf: [(π-crotyl)Pd(tBuXPhos)]OTf;
X = ⁻PF$_6$: [(π-crotyl)Pd(tBuXPhos)]PF$_6$;
X = ⁻BF$_4$: [(π-crotyl)Pd(tBuXPhos)]BF$_4$;
X = ⁻SbF$_6$: [(π-crotyl)Pd(tBuXPhos)]SbF$_6$;
X = [BAr$^F_4$]⁻: [(π-crotyl)Pd(tBuXPhos)][BAr$^F_4$];
X = ⁻OMs: [(π-crotyl)Pd(tBuXPhos)]OMs

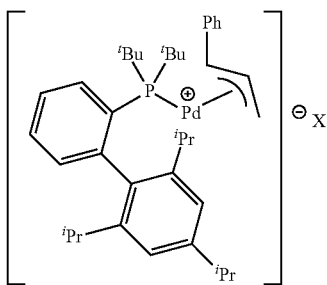

[(π-cinnamyl)Pd(tBuXPhos)]X

X = ⁻OTf: [(π-cinnamyl)Pd(tBuXPhos)]OTf;
X = ⁻PF$_6$: [(π-cinnamyl)Pd(tBuXPhos)]PF$_6$;
X = ⁻BF$_4$: [(π-cinnamyl)Pd(tBuXPhos)]BF$_4$;
X = ⁻SbF$_6$: [(π-cinnamyl)Pd(tBuXPhos)]SbF$_6$;
X = [BAr$^F_4$]⁻: [(π-cinnamyl)Pd(tBuXPhos)][BAr$^F_4$];
X = ⁻OMs: [(π-cinnamyl)Pd(tBuXPhos)]OMs -continued

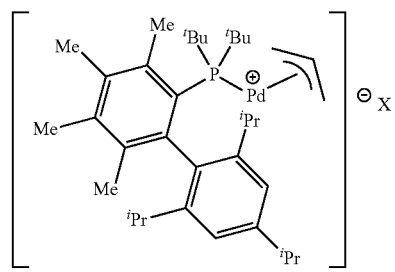

[(π-allyl)Pd(Me$_4$tBuXPhos)]X

X = ⁻OTf: [(π-allyl)Pd(Me$_4$tBuXPhos)]OTf;
X = ⁻PF$_6$: [(π-allyl)Pd(Me$_4$tBuXPhos)]PF$_6$;
X = ⁻BF$_4$: [(π-allyl)Pd(Me$_4$tBuXPhos)]BF$_4$;
X = ⁻SbF$_6$: [(π-allyl)Pd(Me$_4$tBuXPhos)]SbF$_6$;
X = [BAr$^F_4$]⁻: [(π-allyl)Pd(Me$_4$tBuXPhos)][BAr$^F_4$];
X = ⁻OMs: [(π-allyl)Pd(Me$_4$tBuXPhos)]OMs

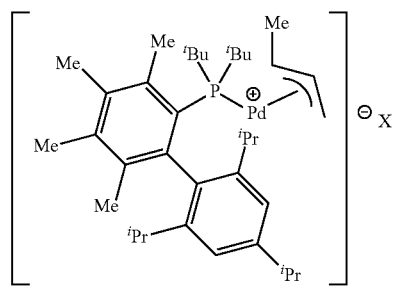

[(π-crotyl)Pd(Me$_4$tBuXPhos)]X

X = ⁻OTf: [(π-crotyl)Pd(Me$_4$tBuXPhos)]OTf;
X = ⁻PF$_6$: [(π-crotyl)Pd(Me$_4$tBuXPhos)]PF$_6$;
X = ⁻BF$_4$: [(π-crotyl)Pd(Me$_4$tBuXPhos)]BF$_4$;
X = ⁻SbF$_6$: [(π-crotyl)Pd(Me$_4$tBuXPhos)]SbF$_6$;
X = [BAr$^F_4$]⁻: [(π-crotyl)Pd(Me$_4$tBuXPhos)][BAr$^F_4$];
X = ⁻OMs: [(π-crotyl)Pd(Me$_4$tBuXPhos)]OMs

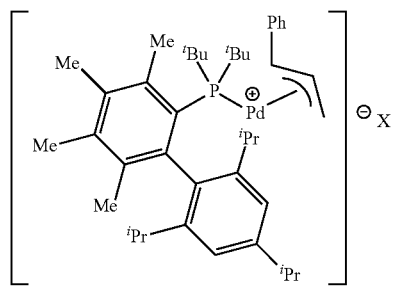

[(π-cinnamyl)Pd(Me$_4$tPhos)]X

X = ⁻OTf: [(π-cinnamyl)Pd(Me$_4$tBuXPhos)]OTf;
X = ⁻PF$_6$: [(π-cinnamyl)Pd(Me$_4$tBuXPhos)]PF$_6$;
X = ⁻BF$_4$: [(π-cinnamyl)Pd(Me$_4$tBuXPhos)]BF$_4$;
X = ⁻SbF$_6$: [(π-cinnamyl)Pd(Me$_4$tBuXPhos)]SbF$_6$;
X = [BAr$^F_4$]⁻: [(π-cinnamyl)Pd(Me$_4$tBuXPhos)][BAr$^F_4$];
X = ⁻OMs: [(π-cinnamyl)Pd(Me$_4$tBuXPhos)]OMs

31

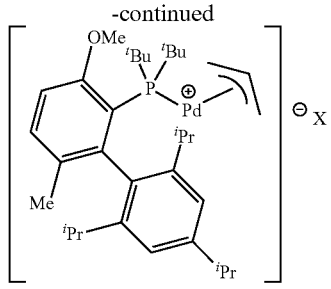

[(π-allyl)Pd(RockPhos)]X

X = ⁻OTf: [(π-allyl)Pd(RockPhos)]OTf;
X = ⁻PF₆: [(π-allyl)Pd(RockPhos)]PF₆;
X = ⁻BF₄: [(π-allyl)Pd(RockPhos)]BF₄;
X = ⁻SbF₆: [(π-allyl)Pd(RockPhos)]SbF₆;
X = [BAr$^F_4$]⁻: [(π-allyl)Pd(RockPhos)][BAr$^F_4$];
X = ⁻OMs: [(π-allyl)Pd(RockPhos)]OMs

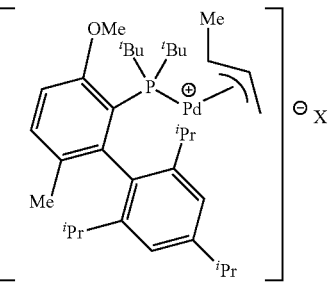

[(π-crotyl)Pd(RockPhos)]X

X = ⁻OTf: [(π-crotyl)Pd(RockPhos)]OTf;
X = ⁻PF₆: [(π-crotyl)Pd(RockPhos)]PF₆;
X = ⁻BF₄: [(π-crotyl)Pd(RockPhos)]BF₄;
X = ⁻SbF₆: [(π-crotyl)Pd(RockPhos)]SbF₆;
X = [BAr$^F_4$]⁻: [(π-crotyl)Pd(RockPhos)][BAr$^F_4$];
X = ⁻OMs: [(π-crotyl)Pd(RockPhos)]OMs

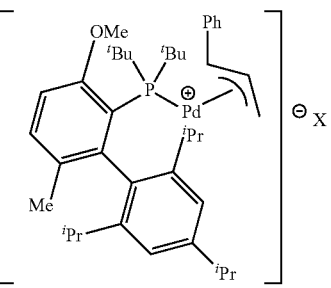

[(π-cinnamyl)Pd(RockPhos)]X

X = ⁻OTf: [(π-cinnamyl)Pd(RockPhos)]OTf;
X = ⁻PF₆: [(π-cinnamyl)Pd(RockPhos)]PF₆;
X = ⁻BF₄: [(π-cinnamyl)Pd(RockPhos)]BF₄;
X = ⁻SbF₆: [(π-cinnamyl)Pd(RockPhos)]SbF₆;
X = [BAr$^F_4$]⁻: [(π-cinnamyl)Pd(RockPhos)][BAr$^F_4$];
X = ⁻OMs: [(π-cinnamyl)Pd(RockPhos)]OMs In one preferred embodiment, the complex of formula (1) may be selected from the group consisting of:

32

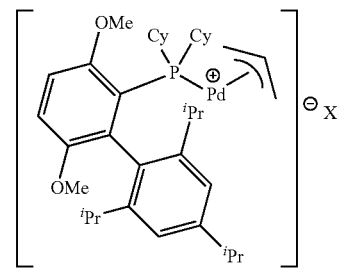

[(π-allyl)Pd(BrettPhos)]X

X = ⁻OTf: [(π-allyl)Pd(BrettPhos)]OTf;
X = ⁻PF₆: [(π-allyl)Pd(BrettPhos)]PF₆;
X = ⁻BF₄: [(π-allyl)Pd(BrettPhos)]BF₄;
X = ⁻SbF₆: [(π-allyl)Pd(BrettPhos)]SbF₆;
X = [BAr$^F_4$]⁻: [(π-allyl)Pd(BrettPhos)][BAr$^F_4$];
X = ⁻OMs: [(π-allyl)Pd(BrettPhos)]OMs

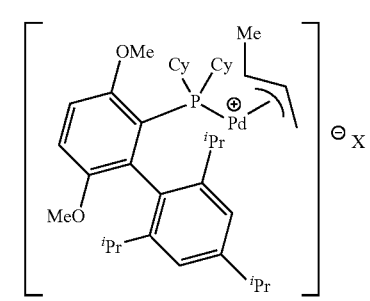

[(π-crotyl)Pd(BrettPhos)]X

X = ⁻OTf: [(π-crotyl)Pd(BrettPhos)]OTf;
X = ⁻PF₆: [(π-crotyl)Pd(BrettPhos)]PF₆;
X = ⁻BF₄: [(π-crotyl)Pd(BrettPhos)]BF₄;
X = ⁻SbF₆: [(π-crotyl)Pd(BrettPhos)]SbF₆;
X = [BAr$^F_4$]⁻: [(π-crotyl)Pd(BrettPhos)][BAr$^F_4$];
X = ⁻OMs: [(π-crotyl)Pd(BrettPhos)]OMs

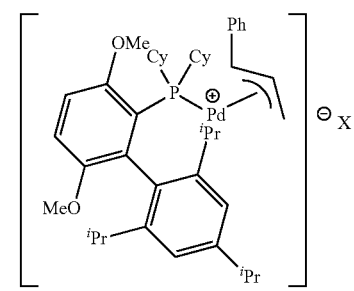

[(π-cinnamyl)Pd(BrettPhos)]X

X = ⁻OTf: [(π-cinnamyl)Pd(BrettPhos)]OTf;
X = ⁻PF₆: [(π-cinnamyl)Pd(BrettPhos)]PF₆;
X = ⁻BF₄: [(π-cinnamyl)Pd(BrettPhos)]BF₄;
X = ⁻SbF₆: [(π-cinnamyl)Pd(BrettPhos)]SbF₆;
X = [BAr$^F_4$]⁻: [(π-cinnamyl)Pd(BrettPhos)][BAr$^F_4$];
X = ⁻OMs: [(π-cinnamyl)Pd(BrettPhos)]OMs

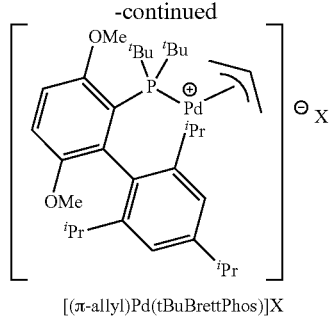

[(π-allyl)Pd(tBuBrettPhos)]X

X = ⁻OTf: [(π-allyl)Pd(tBuBrettPhos)]OTf;
X = ⁻PF₆: [(π-allyl)Pd(tBuBrettPhos)]PF₆;
X = ⁻BF₄: [(π-allyl)Pd(tBuBrettPhos)]BF₄;
X = ⁻SbF₆: [(π-allyl)Pd(tBuBrettPhos)]SbF₆;
X = [BAr$^F_4$]⁻: [(π-allyl)Pd(tBuBrettPhos)][BAr$^F_4$];
X = ⁻OMs: [(π-allyl)Pd(tBuBrettPhos)]OMs

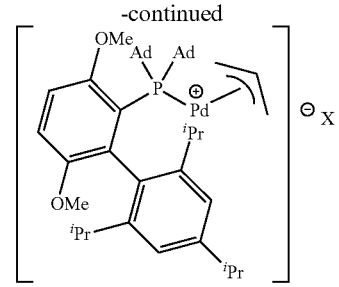

[(π-allyl)Pd(AdBrettPhos)]X

X = ⁻OTf: [(π-allyl)Pd(AdBrettPhos)]OTf;
X = ⁻PF₆: [(π-allyl)Pd(AdBrettPhos)]PF₆;
X = ⁻BF₄: [(π-allyl)Pd(AdBrettPhos)]BF₄;
X = ⁻SbF₆: [(π-allyl)Pd(AdBrettPhos)]SbF₆;
X = [BAr$^F_4$]⁻: [(π-allyl)Pd(AdBrettPhos)][BAr$^F_4$];
X = ⁻OMs: [(π-allyl)Pd(AdBrettPhos)]OMs

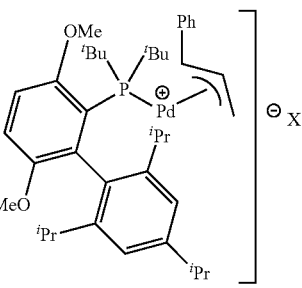

[(π-crotyl)Pd(tBuBrettPhos)]X

X = ⁻OTf: [(π-crotyl)Pd(tBuBrettPhos)]OTf;
X = ⁻PF₆: [(π-crotyl)Pd(tBuBrettPhos)]PF₆;
X = ⁻BF₄: [(π-crotyl)Pd(tBuBrettPhos)]BF₄;
X = ⁻SbF₆: [(π-crotyl)Pd(tBuBrettPhos)]SbF₆;
X = [BAr$^F_4$]⁻: [(π-crotyl)Pd(tBuBrettPhos)][BAr$^F_4$];
X = ⁻OMs: [(π-crotyl)Pd(tBuBrettPhos)]OMs

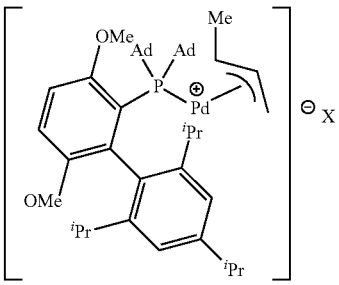

[(π-crotyl)Pd(AdBrettPhos)]X

X = ⁻OTf: [(π-crotyl)Pd(AdBrettPhos)]OTf;
X = ⁻PF₆: [(π-crotyl)Pd(AdBrettPhos)]PF₆;
X = ⁻BF₄: [(π-crotyl)Pd(AdBrettPhos)]BF₄;
X = ⁻SbF₆: [(π-crotyl)Pd(AdBrettPhos)]SbF₆;
X = [BAr$^F_4$]⁻: [(π-crotyl)Pd(AdBrettPhos)][BAr$^F_4$];
X = ⁻OMs: [(π-crotyl)Pd(AdBrettPhos)]OMs

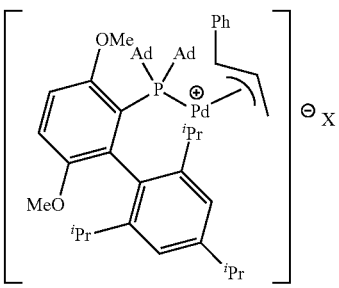

[(π-cinnamyl)Pd(tBuBrettPhos)]X

X = ⁻OTf: [(π-cinnamyl)Pd(tBuBrettPhos)]OTf;
X = ⁻PF₆: [(π-cinnamyl)Pd(tBuBrettPhos)]PF₆;
X = ⁻BF₄: [(π-cinnamyl)Pd(tBuBrettPhos)]BF₄;
X = ⁻SbF₆: [(π-cinnamyl)Pd(tBuBrettPhos)]SbF₆;
X = [BAr$^F_4$]⁻: [(π-cinnamyl)Pd(tBuBrettPhos)][BAr$^F_4$];
X = ⁻OMs: [(π-cinnamyl)Pd(tBuBrettPhos)]OMs

[(π-cinnamyl)Pd(AdBrettPhos)]X

X = ⁻OTf: [(π-cinnamyl)Pd(AdBrettPhos)]OTf;
X = ⁻PF₆: [(π-cinnamyl)Pd(AdBrettPhos)]PF₆;
X = ⁻BF₄: [(π-cinnamyl)Pd(AdBrettPhos)]BF₄;
X = ⁻SbF₆: [(π-cinnamyl)Pd(AdBrettPhos)]SbF₆;
X = [BAr$^F_4$]⁻: [(π-cinnamyl)Pd(AdBrettPhos)][BAr$^F_4$];
X = ⁻OMs: [(π-cinnamyl)Pd(AdBrettPhos)]OMs

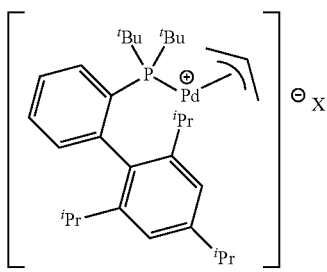

[(π-allyl)Pd(tBuXPhos)]X

X = ⁻OTf: [(π-allyl)Pd(tBuXPhos)]OTf;
X = ⁻PF₆: [(π-allyl)Pd(tBuXPhos)]PF₆;
X = ⁻BF₄: [(π-allyl)Pd(tBuXPhos)]BF₄;
X = ⁻SbF₆: [(π-allyl)Pd(tBuXPhos)]SbF₆;
X = [BAr$^F_4$]⁻: [(π-allyl)Pd(tBuXPhos)][BAr$^F_4$];
X = ⁻OMs: [(π-allyl)Pd(tBuXPhos)]OMs

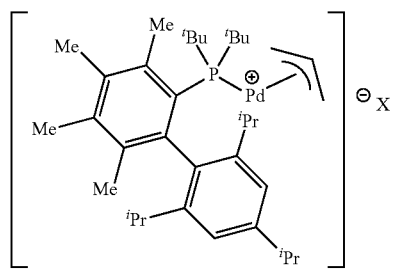

[(π-allyl)Pd(Me₄tBuXPhos)]X

X = ⁻OTf: [(π-allyl)Pd(Me₄tBuXPhos)]OTf;
X = ⁻PF₆: [(π-allyl)Pd(Me₄tBuXPhos)]PF₆;
X = ⁻BF₄: [(π-allyl)Pd(Me₄tBuXPhos)]BF₄;
X = ⁻SbF₆: [(π-allyl)Pd(Me₄tBuXPhos)]SbF₆;
X = [BAr$^F_4$]⁻: [(π-allyl)Pd(Me₄tBuXPhos)][BAr$^F_4$];
X = ⁻OMs: [(π-allyl)Pd(Me₄tBuXPhos)]OMs

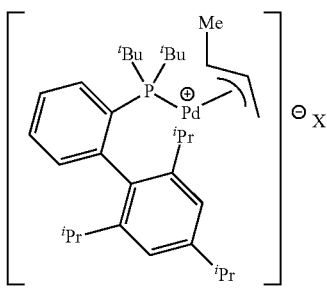

[(π-crotyl)Pd(tBuXPhos)]X

X = ⁻OTf: [(π-crotyl)Pd(tBuXPhos)]OTf;
X = ⁻PF₆: [(π-crotyl)Pd(tBuXPhos)]PF₆;
X = ⁻BF₄: [(π-crotyl)Pd(tBuXPhos)]BF₄;
X = ⁻SbF₆: [(π-crotyl)Pd(tBuXPhos)]SbF₆;
X = [BAr$^F_4$]⁻: [(π-crotyl)Pd(tBuXPhos)][BAr$^F_4$];
X = ⁻OMs: [(π-crotyl)Pd(tBuXPhos)]OMs

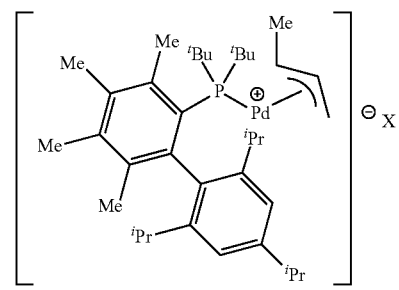

[(π-crotyl)Pd(Me₄tBuXPhos)]X

X = ⁻OTf: [(π-crotyl)Pd(Me₄tBuXPhos)]OTf;
X = ⁻PF₆: [(π-crotyl)Pd(Me₄tBuXPhos)]PF₆;
X = ⁻BF₄: [(π-crotyl)Pd(Me₄tBuXPhos)]BF₄;
X = ⁻SbF₆: [(π-crotyl)Pd(Me₄tBuXPhos)]SbF₆;
X = [BAr$^F_4$]⁻: [(π-crotyl)Pd(Me₄tBuXPhos)][BAr$^F_4$];
X = ⁻OMs: [(π-crotyl)Pd(Me₄tBuXPhos)]OMs

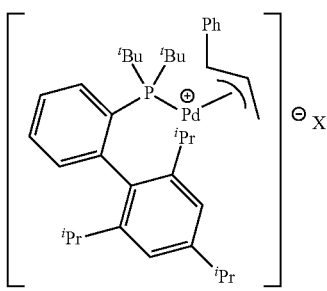

[(π-cinnamyl)Pd(tBuXPhos)]X

X = ⁻OTf: [(π-cinnamyl)Pd(tBuXPhos)]OTf;
X = ⁻PF₆: [(π-cinnamyl)Pd(tBuXPhos)]PF₆;
X = ⁻BF₄: [(π-cinnamyl)Pd(tBuXPhos)]BF₄;
X = ⁻SbF₆: [(π-cinnamyl)Pd(tBuXPhos)]SbF₆;
X = [BAr$^F_4$]⁻: [(π-cinnamyl)Pd(tBuXPhos)][BAr$^F_4$];
X = ⁻OMs: [(π-cinnamyl)Pd(tBuXPhos)]OMs

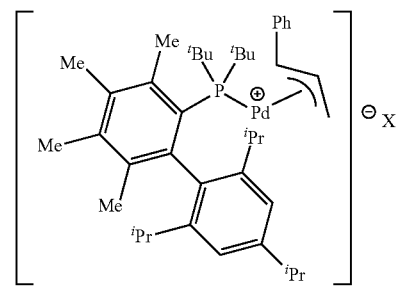

[(π-cinnamyl)Pd(Me₄tPhos)]X

X = ⁻OTf: [(π-cinnamyl)Pd(Me₄tBuXPhos)]OTf;
X = ⁻PF₆: [(π-cinnamyl)Pd(Me₄tBuXPhos)]PF₆;
X = ⁻BF₄: [(π-cinnamyl)Pd(Me₄tBuXPhos)]BF₄;
X = ⁻SbF₆: [(π-cinnamyl)Pd(Me₄tBuXPhos)]SbF₆;
X = [BAr$^F_4$]⁻: [(π-cinnamyl)Pd(Me₄tBuXPhos)][BAr$^F_4$];
X = ⁻OMs: [(π-cinnamyl)Pd(Me₄tBuXPhos)]OMs

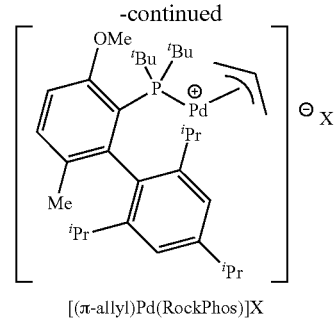

[(π-allyl)Pd(RockPhos)]X

X = ⁻OTf: [(π-allyl)Pd(RockPhos)]OTf;
X = ⁻PF₆: [(π-allyl)Pd(RockPhos)]PF₆;
X = ⁻BF₄: [(π-allyl)Pd(RockPhos)]BF₄;
X = ⁻SbF₆: [(π-allyl)Pd(RockPhos)]SbF₆;
X = [BAr$^F_4$]⁻: [(π-allyl)Pd(RockPhos)][BAr$^F_4$];
X = ⁻OMs: [(π-allyl)Pd(RockPhos)]OMs

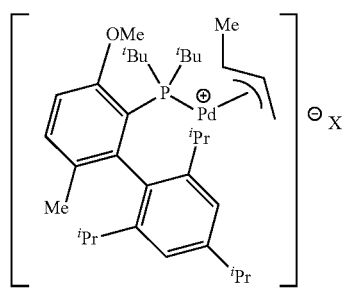

[(π-crotyl)Pd(RockPhos)]X

X = ⁻OTf: [(π-crotyl)Pd(RockPhos)]OTf;
X = ⁻PF₆: [(π-crotyl)Pd(RockPhos)]PF₆;
X = ⁻BF₄: [(π-crotyl)Pd(RockPhos)]BF₄;
X = ⁻SbF₆: [(π-crotyl)Pd(RockPhos)]SbF₆;
X = [BAr$^F_4$]⁻: [(π-crotyl)Pd(RockPhos)][BAr$^F_4$];
X = ⁻OMs: [(π-crotyl)Pd(RockPhos)]OMs

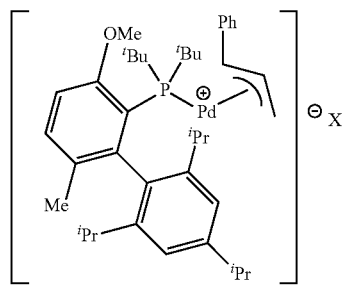

[(π-cinnamyl)Pd(RockPhos)]X

X = ⁻OTf: [(π-cinnamyl)Pd(RockPhos)]OTf;
X = ⁻PF₆: [(π-cinnamyl)Pd(RockPhos)]PF₆;
X = ⁻BF₄: [(π-cinnamyl)Pd(RockPhos)]BF₄;
X = ⁻SbF₆: [(π-cinnamyl)Pd(RockPhos)]SbF₆;
X = [BAr$^F_4$]⁻: [(π-cinnamyl)Pd(RockPhos)][BAr$^F_4$];
X = ⁻OMs: [(π-cinnamyl)Pd(RockPhos)]OMs In one particularly preferred embodiment, the complex of formula (1) may be selected from the group consisting of:

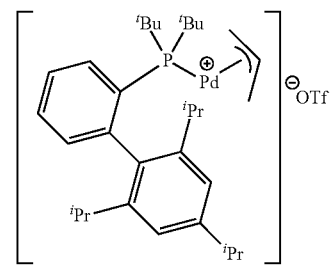

[(π-allyl)Pd(tBuXPhos)]OTf

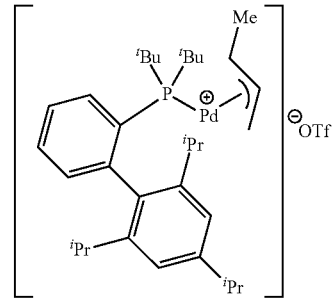

[(π-crotyl)Pd(tBuXPhos)]OTf

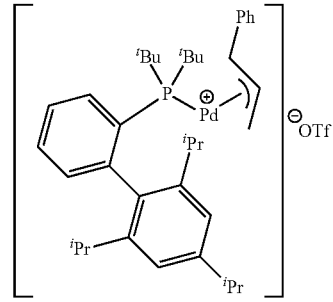

[(π-cinnamyl)Pd(tBuXPhos)]OTf

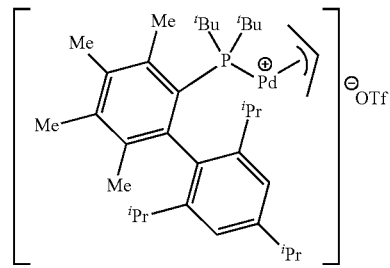

[(π-allyl)Pd(Me₄tBuXPhos)]OTf

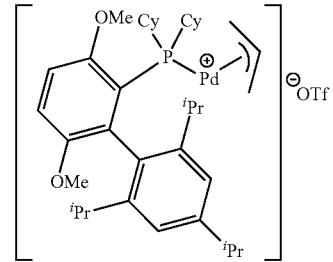

[(π-allyl)Pd(BrettPhos)]OTf

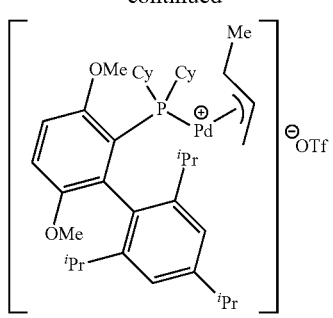

[(π-crotyl)Pd(BrettPhos)]OTf

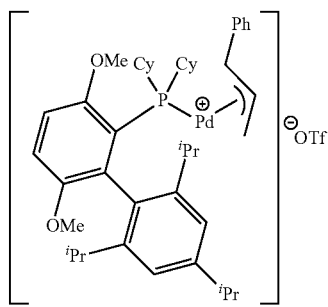

[(π-cinnamyl)Pd(BrettPhos)]OTf

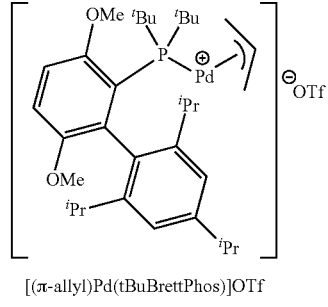

[(π-allyl)Pd(tBuBrettPhos)]OTf

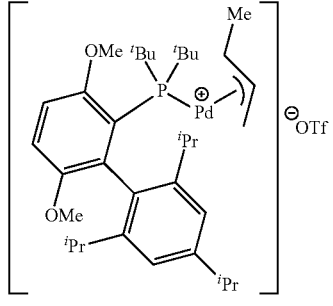

[(π-crotyl)Pd(tBuBrettPhos)]OTf

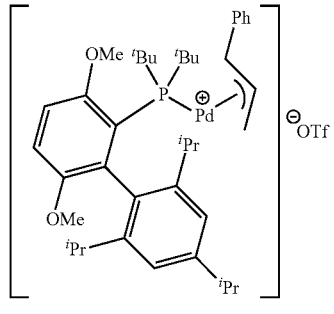

[(π-cinnamyl)Pd(tBuBrettPhos)]OTf

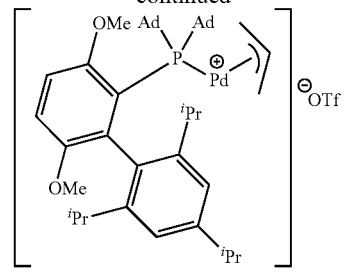

[(π-allyl)Pd(AdBrettPhos)]OTf

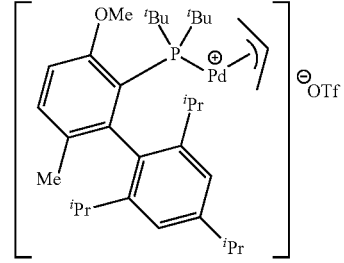

[(π-allyl)Pd(RockPhos)]OTf

In another aspect, the present invention provides a palladium(II) complex of formula (3):

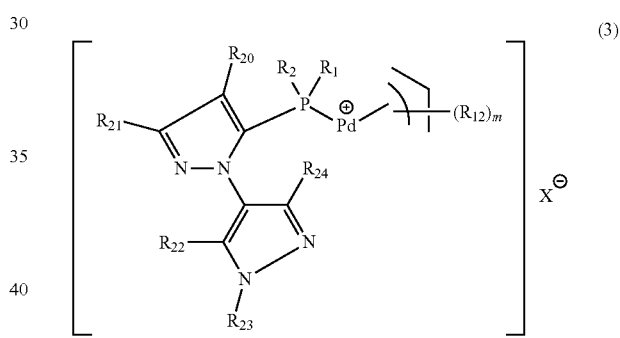

wherein:

$R_1$ and $R_2$ are independently organic groups having 1-20 carbon atoms, or $R_1$ and $R_2$ are linked to form a ring structure with E;

$R_{12}$ is an organic group having 1-20 carbon atoms;

$R_{20}$, $R_{21}$, $R_{22}$, $R_{23}$ and $R_{24}$ are independently —H or organic groups having 1-20 carbon atoms; or one or more pairs selected from $R_1/R_{20}$, $R_2/R_{20}$, $R_{20}/R_{21}$ or $R_{22}/R_{23}$ may independently form a ring structure with the atoms to which they are attached;

m is 0, 1, 2, 3, 4 or 5; and $X^{\ominus}$ is a non-coordinated anionic ligand.

The complex of formula (3) is a cationic palladium(II) complex comprising a monodentate bi-heteroaryl tertiary phosphine ligand, a non-coordinated anionic ligand and an optionally substituted π-allyl group.

$R_1$, $R_2$, $R_{12}$, m and $X^{\ominus}$ are as described above.

In one preferred embodiment, $R_1$ and $R_2$ are the same and are tert-butyl or cyclohexyl groups.

$R_{20}$, $R_{21}$, $R_{22}$, $R_{23}$ and $R_{24}$ are independently —H or organic groups having 1-20 carbon atoms. $R_{20}$, $R_{21}$, $R_{22}$, $R_{23}$ and $R_{24}$ are selected up to the limitations imposed by stability and the rules of valence. $R_{20}$ and $R_{21}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, and substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteroaryl or heterocycloalkyl groups may be independently selected from sulfur, nitrogen or/and oxygen. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3\text{-}10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, —NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$OMe)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxyphenyl)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include $C_{4\text{-}8}$-heterocycloalkyl groups, such as piperidinyl and morpholinyl.

In one preferred embodiment, both of $R_{20}$ and $R_{21}$ are —H.

$R_{22}$ and $R_{24}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted-thioalkyl, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different). The heteroatoms in the heteroaryl groups may be independently selected from sulfur, nitrogen or/and oxygen. In one embodiment, the alkyl groups may be optionally substituted with one or more (e.g. 1, 2, 3, 4, or 5) substituents such as halide (F, Cl, Br or I), alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3\text{-}10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Substituted or unsubstituted-thioalkyl groups include —S($C_{1\text{-}5}$-alkyl), such as —SMe, —SEt, —SPr (n- or i-). In one embodiment, both of $R_{22}$ and $R_{24}$ are phenyl.

$R_{23}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, and substituted and unsubstituted heteroaryl. The heteroatoms in the heteroaryl groups may be independently selected from sulfur, nitrogen or/and oxygen. In one embodiment, the alkyl groups may be optionally substituted with one or more (e.g. 1, 2, 3, 4, or 5) substituents such as halide (F, Cl, Br or I), alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. ($C_1$-$C_{10}$ dialkyl)amino), heterocycloalkyl (e.g. $C_{3\text{-}10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. In one embodiment, $R_{23}$ is phenyl.

In one preferred embodiment, each of $R_{22}$, $R_{23}$ and $R_{24}$ are phenyl groups.

In one embodiment, the monodentate bi-heteroaryl tertiary phosphine ligand is selected from the group consisting of:

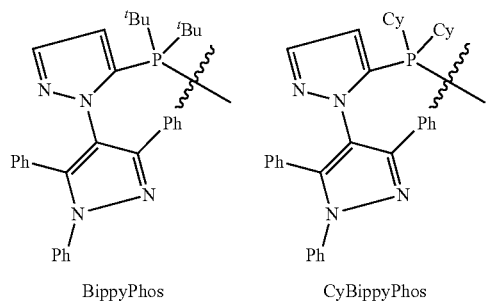

BippyPhos     CyBippyPhos

The complex of formula (3) may be selected from the group consisting of:

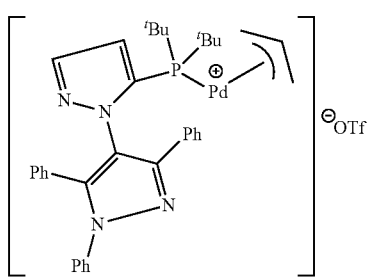

[(π-allyl)Pd(BippyPhos)]OTf

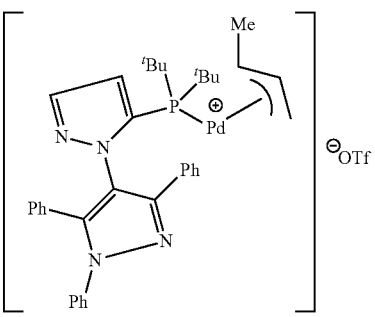

[(π-croty)Pd(BippyPhos)]OTf

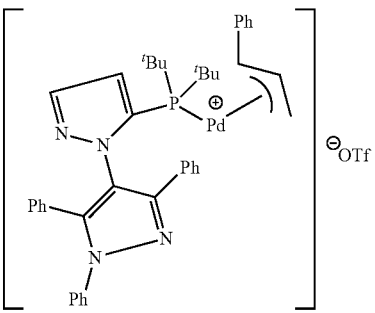

[(π-cinnamyl)Pd(BippyPhos)]OTf

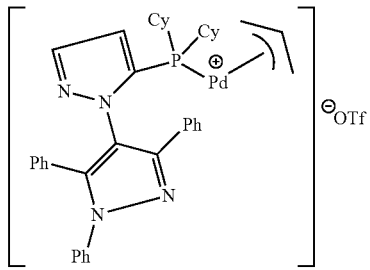

[(π-allyl)Pd(BippyPhos)]OTf

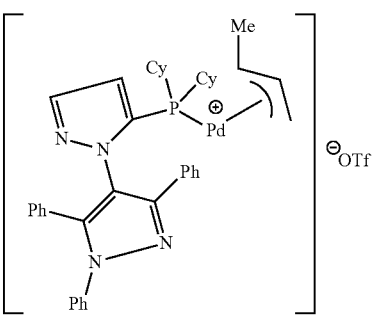

[(π-croty)Pd(BippyPhos)]OTf

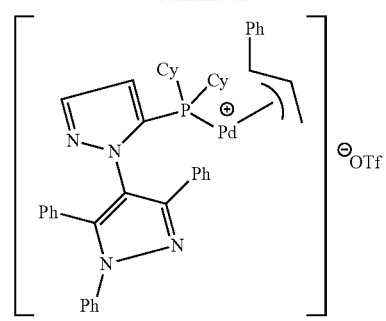

[(π-cinnamyl)Pd(BippyPhos)]OTf

The complex of formula (1) may be prepared in a process comprising the steps of:

(a) reacting a complex of formula (4) with a monodentate biaryl ligand of formula (5) to form a complex of formula (6)

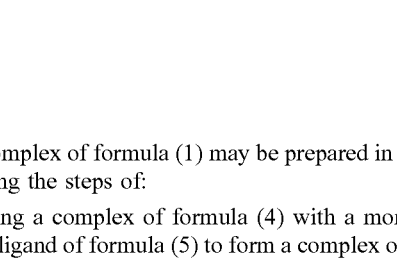

(4)

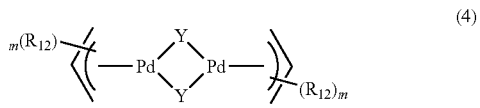

(5)

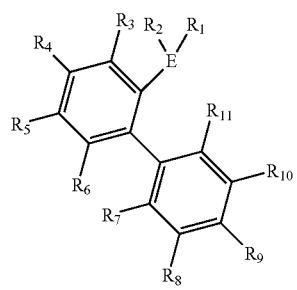

(6)

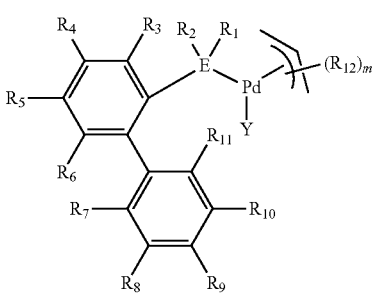

and;

(b) reacting the complex of formula (6) with a silver salt of formula (7) to form the complex of formula (1),

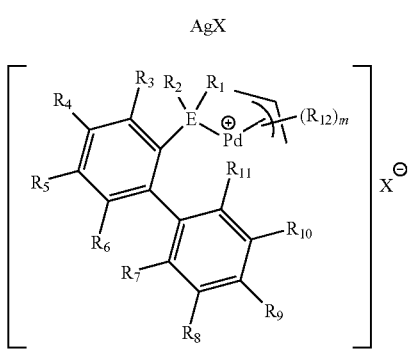

(7)

(1)

wherein:
- $R_1$ and $R_2$ are independently organic groups having 1-20 carbon atoms, or $R_1$ and $R_2$ are linked to form a ring structure with E;
- $R_3$, $R_4$, $R_5$, $R_6$, $R_7$, $R_8$, $R_9$, $R_{10}$ and $R_{11}$ are independently —H or organic groups having 1-20 carbon atoms; or one or more pairs selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$ independently form a ring structure with the atoms to which they are attached;
- $R_{12}$ is an organic group having 1-20 carbon atoms;
- m is 0, 1, 2, 3, 4 or 5;
- E is P or As;
- Y is a coordinating anionic ligand; and
- $X^\ominus$ is a non-coordinated anionic ligand.

$R_1$, $R_2$, $R_3$, $R_4$, $R_5$, $R_6$, $R_7$, $R_8$, $R_9$, $R_{10}$, $R_{11}$, $R_{12}$, m, E and $X^\ominus$ are as described above.

One or more pairs (e.g. 1, 2 or 3 pairs) selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$ may independently form a ring structure with the atoms to which they are attached. The pair or pairs are selected up to the limitations imposed by stability and the rules of valence. The ring structure may be a substituted or unsubstituted cycloalkyl, substituted or unsubstituted heterocycloalkyl, substituted or unsubstituted aryl or substituted or unsubstituted heteroaryl group.

If $R_1$, $R_2$, $R_3$, $R_4$, $R_5$, $R_6$, $R_7$, $R_8$, $R_9$, $R_{10}$ or $R_{11}$ does not form part of a pair, the groups are as described above.

$R_1/R_3$ or $R_2/R_3$ may form a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above. The pair or pairs are selected up to the limitations imposed by stability and the rules of valence.

The linking group for $R_1/R_3$ or $R_2/R_3$ may be a substituted or unsubstituted alkyl, substituted or unsubstituted alkoxy, or substituted or unsubstituted heteroalkyl. The ring structure formed from the pair or pairs selected from the group consisting of $R_4/R_5$, $R_5/R_6$, $R_7/R_8$, $R_8/R_9$, $R_9/R_{10}$ and $R_{10}/R_{11}$ may be a substituted or unsubstituted cycloalkyl, substituted or unsubstituted heterocycloalkyl, substituted or unsubstituted aryl or substituted or unsubstituted heteroaryl group. $R_1$ and $R_2$ may be independently selected from the groups defined above when they do not form a ring structure with $R_3$.

In one embodiment, $R_4$, $R_5$ and $R_6$ are —H and the pair $R_1/R_3$ or $R_2/R_3$ forms a ring structure with the atoms to which they are attached. In another embodiment, $R_4$, $R_5$ and $R_6$ are —H and the pair $R_1/R_3$ or $R_2/R_3$ forms a ring structure with the atoms to which they are attached. In either of these instances, $R_7/R_8$, $R_8/R_9$, $R_9/R_{10}$ or $R_{10}/R_{11}$ may independently form a ring structure with the carbon atoms to which they are attached or $R_7$, $R_8$, $R_9$, $R_{10}$ and $R_{11}$ are as defined above. $R_1/R_3$ or $R_2/R_3$ may form a ring structure selected from the group consisting of:

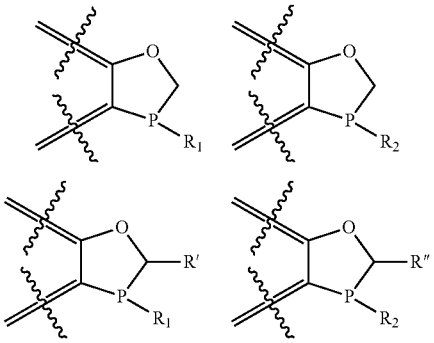

wherein:
- $R_1$ and $R_2$ are as defined above: and
- R' and R" are independently as defined above for $R_1$ and $R_2$.

In one embodiment, R' and R" are independently selected from the group consisting of methyl, propyl (n- or i-), butyl (n-, i- or t-), cyclohexyl or phenyl.

In another embodiment, $R_9$ is —H and the pairs $R_7/R_8$ and $R_{10}/R_{11}$ form a ring structure with the atoms to which they are attached. Each pair may form a substituted or unsubstituted aryl ring (for example, a phenyl ring) together with the carbon atoms to which they are attached.

Examples of phosphorus ligands include those described by Tang et al, Angew. Chem. Int. Ed. 2010, 49, 5879-5883, Zhao et al, Chem. Eur. J, 2013, 19(7), 2261-2265 and Xu et al, Journal of the American Chemical Society, 2014, 136(2), 570-573 such as:

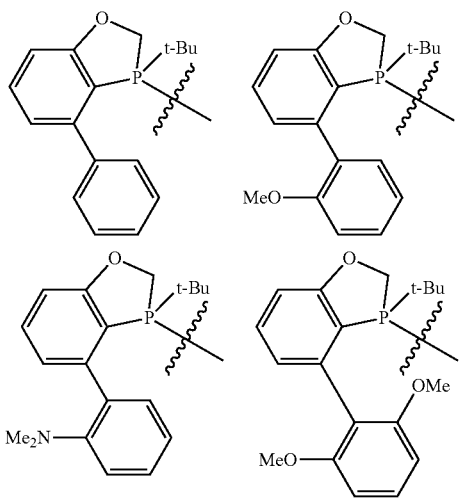

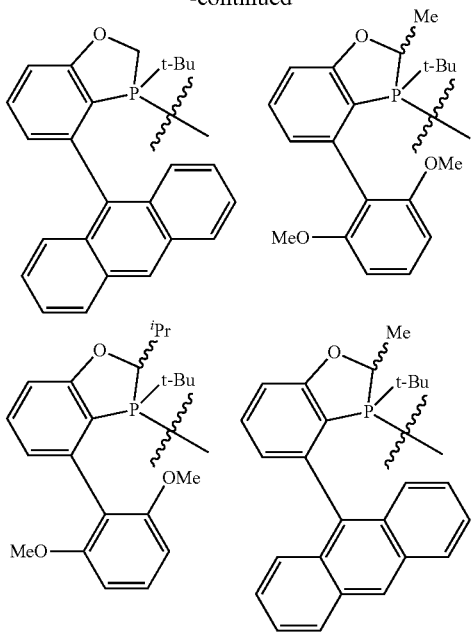

It will be understood that, in the depictions herein, where -Me or -$^i$Pr is connected by a wavy line ($\sim$), either stereoisomer may be present.

In one embodiment, $R_5$ and $R_6$ form a substituted or unsubstituted aryl ring, preferably a phenyl ring, together with the carbon atoms to which they are attached. In another embodiment, $R_7$ and $R_8$ form a substituted or unsubstituted aryl ring, preferably a phenyl ring, together with the carbon atoms to which they are attached. An example is represented below:

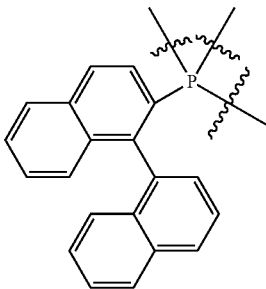

This process for the preparation of the complex of formula (1) is suitable when the monodentate biaryl ligand (5) is less sterically bulky. Without wishing to be bound by theory, it is believed that the complexes of formula (6) can be prepared as a result of balancing the steric bulk of groups $R_1$ and $R_2$ with the steric bulk of groups $R_7$, $R_8$, $R_9$, $R_{10}$ and/or $R_{11}$. For example, in the complex of formula (6), when E is P, $R_1$ and $R_2$ may be selected to be more sterically bulky than a cyclohexyl group (for example a tert-butyl group) when the substituents $R_7$, $R_8$, $R_9$, $R_{10}$ and/or $R_{11}$ are selected to be less sterically bulky (for example H). Similarly, $R_1$ and $R_2$ are typically selected to be less sterically bulky (for example a cyclohexyl group or smaller) when the substituents $R_7$, $R_8$, $R_9$, $R_{10}$ and/or $R_{11}$ are selected to be more sterically bulky (for example methoxy, iso-propyl, dimethylamino). This process cannot be typically used when the monodentate biaryl ligand (5) is extremely sterically bulky e.g. tBuXPhos, Me$_4$tBuXPhos, tBuBrettPhos, RockPhos or AdBrettPhos. In this latter instance, the process described below is more suitable.

The complex of formula (4) may be prepared according to known methods (see, for example, a) Marion, N.: Navarro, O.; Mei, J.; Stevens, E. D.; Scott, N. M.; Nolan, S. P. *J. Am. Chem. Soc.* 2006, 128, 4101. b) Auburn, P. R.; Mackenzie, P. B.; Bosnich, B. *J. Am. Chem. Soc.* 1985, 107, 2033. c) Dent, W. I.; Long, R.; Wilkinson, G. *J. Chem. Soc.* 1964, 1585. d) Nicholson, J. K.; Powell, J.; Shaw, B. L. *J. Chem. Soc.; Chem. Commun.* 1966, 174) each of which is incorporated herein by reference in its entirety for all purposes. Suitable complexes of formula (4) include:

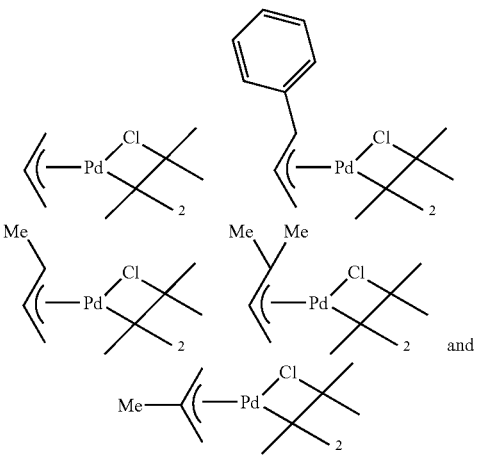

The complex of formula (4) and monodentate biaryl ligand may be combined in a solvent. In this case, the solvent is any suitable aprotic solvent or combination of aprotic solvents. Examples of aprotic solvents are toluene, benzene, tetrahydrofuran (THF), 2-methyltetrahydrofuran (2-MeTHF), dichloromethane (DCM), dioxane, acetone, acetonitrile, dimethylformamide (DMF), N-methylpyrrolidine (NMP), dimethylacetamide (DMAc), methyltertbutylether (MTBE), diethylether, hexane, heptane, pentane or ethylacetate. Preferred solvents are THF, 2-methyltetrahydrofuran, toluene, DCM or a combination thereof. The solvent may be anhydrous. The concentration of the complex of formula (4) in the solvent is preferably about 0.001 mol/L to about 3.00 mol/L and more preferably, about 0.01 mol/L to about 2.50 mol/L, such as about 0.03 mol/L to about 2.50 mol/L.

Any suitable quantity of ligand (5) may be used, although it is preferred that the molar ratio of the complex of formula (4):monodentate biaryl ligand (5) is from about 1:1.90 to about 1:2.30, such as about 1:2.0.

Y may be a halo group, preferably, Cl, Br or I, and more preferably, Cl.

The reaction mixture obtained after step (a) may be reacted directly with the silver salt of formula (7). Alternatively, the complex of formula (6) may be isolated and, if desired, purified before it is reacted with the silver salt of formula (7).

The silver salt of formula (7) (AgX) undergoes an anion exchange with the coordinating anion ligand (Y) present in the complex (6) to form a substantially insoluble silver salt AgY which precipitates out of the reaction medium. Any suitable quantity of AgX (7) may be used, although it is preferred that the molar ratio of the complex of formula (4):AgX (7) is from about 1:1.90 to about 1:2.2, such as about 1:2.0.

The reaction is preferably carried out under an inert atmosphere, such as nitrogen or argon.

The process may be carried out at a temperature in the range of about −10° C. to about 60° C., preferably about 0° C. to about 35° C. and more preferably at about room temperature (rt) (i.e. about 20° C. to about 30° C.). It is preferred that the temperature is maintained below the decomposition temperature and so when the complexes of formula (1), (4) or (6) are known to decompose within the temperature ranges given above, the temperature should be maintained below the decomposition temperature.

The reaction may be carried out for a period of from about several minutes to about 24 hours. Usually the reaction is complete within about 6 hours for a laboratory scale reaction. On completion, a proportion of the solvent may be evaporated if desired prior to recovery of the complex. Furthermore, if desired an anti-solvent (e.g. an alkane, such as pentane or hexane) may be used to precipitate the complex from the solvent. The complex product may be recovered directly by filtering, decanting or centrifuging.

Howsoever the complex is recovered, the separated complex may be washed and then dried. Drying may be performed using known methods, for example at temperatures in the range 10-60° C. and preferably 20-40° C. under 1-30 mbar vacuum for 1 hour to 5 days. If desired the complex may be recrystallised.

The complex of formula (1) or the complex of formula (3) may also be prepared in a process comprising the steps of:

(a) reacting a complex of formula (4) with a silver salt of formula (7),

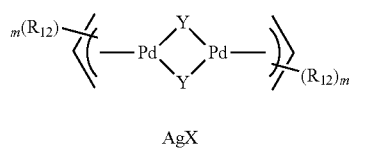

(4)

AgX (7)

and;

(b) reacting the product of step (a) with a monodentate biaryl ligand of formula (5) or a monodentate bi-heteroaryl tertiary phosphine ligand of formula (8) to form the complex of formula (1) or the complex of formula (3).

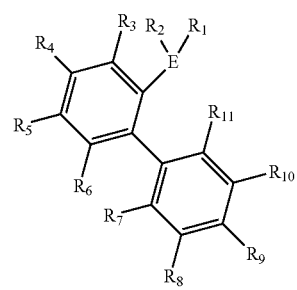

(5)

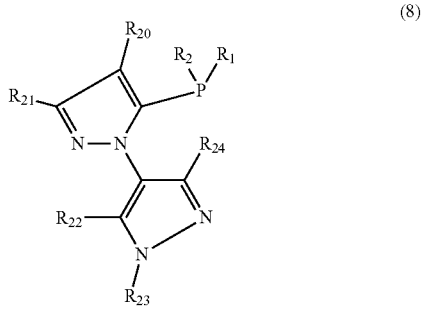

(8)

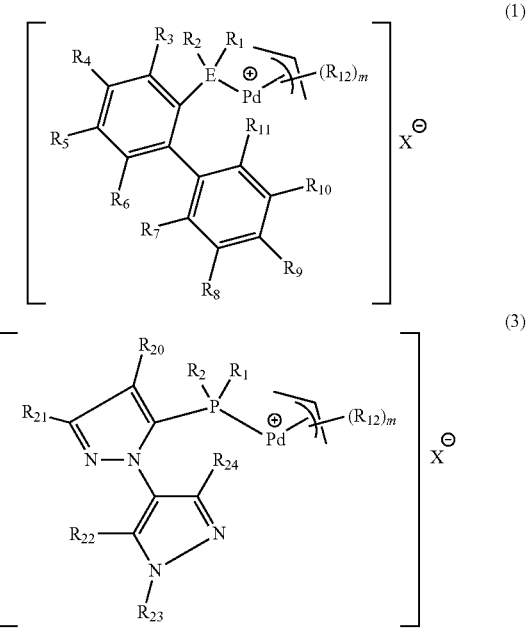

(1)

(3)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or one or more pairs selected from $R_1/R_2$, $R_2/R_3$, $R_3/R_4$, $R_4/R_5$, $R_5/R_6$, $R_7/R_8$, $R_8/R_9$, $R_9/R_{10}$ or $R_{10}/R_{11}$ independently form a ring structure with the atoms to which they are attached;
$R_{12}$ is an organic group having 1-20 carbon atoms;
$R_{20}$, $R_{21}$, $R_{22}$, $R_{23}$ and $R_{24}$ are independently —H or organic groups having 1-20 carbon atoms; or one or more pairs selected from $R_1/R_{20}$, $R_2/R_{20}$, $R_{20}/R_{21}$ or $R_{22}/R_{23}$ may independently form a ring structure with the atoms to which they are attached;
m is 0, 1, 2, 3, 4 or 5;
E is P or As;
Y is a coordinating anionic ligand; and
$X^{\ominus}$ is a non-coordinated anionic ligand.
$R_1$, $R_2$, $R_3$, $R_4$, $R_5$, $R_6$, $R_7$, $R_8$, $R_9$, $R_{10}$, $R_{11}$, $R_{12}$, $R_{20}$, $R_{21}$, $R_{22}$, $R_{23}$, $R_{24}$, m, E, Y and $X^{\ominus}$ are as described above. The complex of formula (4) and the silver salt of formula (7) are also as described above.

One or more pairs (e.g. 1, 2 or 3 pairs) selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$ may independently form a ring structure with the atoms to which they are attached. The pair or pairs are selected up to the limitations imposed by stability and the rules of valence. The ring structure may be a substituted or unsubstituted cycloalkyl, substituted or unsubstituted heterocycloalkyl, substituted or unsubstituted aryl or substituted or unsubstituted heteroaryl group.

If $R_1$, $R_2$, $R_3$, $R_4$, $R_5$, $R_6$, $R_7$, $R_8$, $R^9$, $R_{10}$ or $R_{11}$ does not form part of a pair, the groups are as described above.

$R_1/R_3$ or $R_2/R_3$ may form a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above. The pair or pairs are selected up to the limitations imposed by stability and the rules of valence.

The linking group for $R_1/R_3$ or $R_2/R_3$ may be a substituted or unsubstituted alkyl, substituted or unsubstituted alkoxy, or substituted or unsubstituted heteroalkyl. The ring structure formed from the pair or pairs selected from the group consisting of $R_4/R_5$, $R_5/R_6$, $R_7/R_8$, $R_8/R_9$, $R_9/R_{10}$ and $R_{10}/R_{11}$ may be a substituted or unsubstituted cycloalkyl, substituted or unsubstituted heterocycloalkyl, substituted or unsubstituted aryl or substituted or unsubstituted heteroaryl group. $R_1$ and $R_2$ may be independently selected from the groups defined above when they do not form a ring structure with $R_3$.

In one embodiment, $R_4$, $R_5$ and $R_6$ are —H and the pair $R_1/R_3$ or $R_2/R_3$ forms a ring structure with the atoms to which they are attached. In another embodiment, $R_4$, $R_5$ and $R_6$ are —H and the pair $R_1/R_3$ or $R_2/R_3$ forms a ring structure with the atoms to which they are attached. In either of these instances, $R_7/R_8$, $R_8/R_9$, $R_9/R_{10}$ or $R_{10}/R_{11}$ may independently form a ring structure with the carbon atoms to which they are attached or $R_7$, $R_8$, $R_9$, $R_{10}$ and $R_{11}$ are as defined above. $R_1/R_3$ or $R_2/R_3$ may form a ring structure selected from the group consisting of:

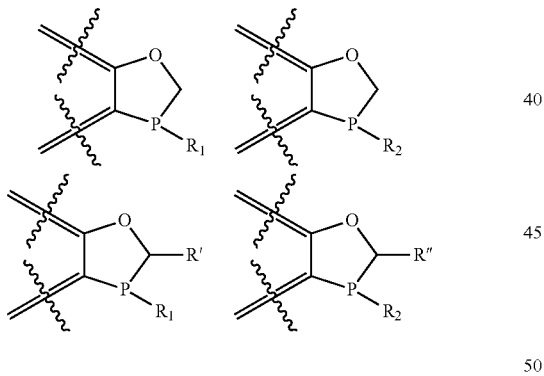

wherein:
$R_1$ and $R_2$ are as defined above: and
R' and R" are independently as defined above for $R_1$ and $R_2$.

In one embodiment, R' and R" are independently selected from the group consisting of methyl, propyl (n- or i-), butyl (n-, i- or t-), cyclohexyl or phenyl.

In another embodiment, $R_9$ is —H and the pairs $R_7/R_8$ and $R_{10}/R_{11}$ form a ring structure with the atoms to which they are attached. Each pair may form a substituted or unsubstituted aryl ring (for example, a phenyl ring) together with the carbon atoms to which they are attached.

Examples of phosphorus ligands include those described by Tang et al, Angew. Chem. Int. Ed. 2010, 49, 5879-5883, Zhao et al, Chem. Eur. J, 2013, 19(7), 2261-2265 and Xu et al, Journal of the American Chemical Society, 2014, 136(2), 570-573 such as:

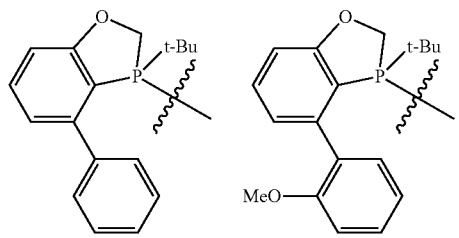

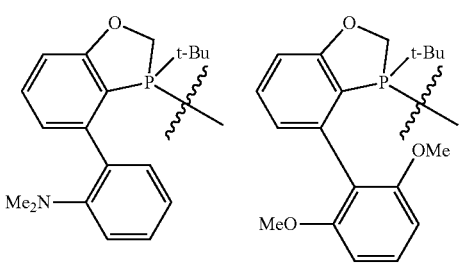

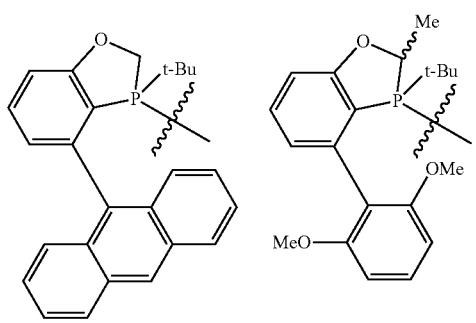

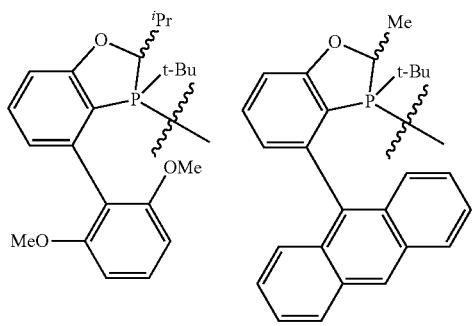

It will be understood that, in the depictions herein, where -Me or -$^i$Pr is connected by a wavy line (∿), either stereoisomer may be present.

In one embodiment, $R_5$ and $R_6$ form a substituted or unsubstituted aryl ring, preferably a phenyl ring, together with the carbon atoms to which they are attached. In another embodiment, $R_7$ and $R_8$ form a substituted or unsubstituted aryl ring, preferably a phenyl ring, together with the carbon atoms to which they are attached. An example is represented below:

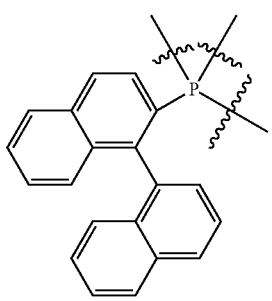

This process for the preparation of the complex of formulae (1) and (3) is suitable when the monodentate biaryl ligand (6) or monodentate bi-heteroaryl tertiary phosphine ligand (8) is extremely sterically hindered, such as those selected from the group consisting of tBuXPhos, Me₄tBuXPhos, tBuBrettPhos, RockPhos and AdBrettPhos, although this method may also be used for less sterically hindered ligands.

Without wishing to be bound by theory, it is postulated that an "[(R₁₂)ₘ-allylPd]OTf" intermediate, an allylpalladium complex functionalised with an easily dissociable counterion, such as a triflate, may be formed on reaction of the complex of formula (4) with the silver salt of formula (7). The intermediate is then reacted in situ with the ligand of formula (5) or (8).

DCM or a combination thereof. The solvent may be anhydrous. The concentration of the complex of formula (4) in the solvent is preferably about 0.001 mol/L to about 5.00 mol/L, for example, about 0.01 mol/L to about 2.50 mol/L, such as about 0.001 mol/L to about 0.25 mol/L e.g. about 0.01 mol/L to about 0.25 mol/L, such as about 0.01 mol/L to about 0.22 mol/L, e.g. about 0.03 mol/L to about 0.22 mol/L, such as about 0.05 mol/L.

The silver salt of formula (6) (AgX) undergoes an anion exchange with the coordinating anion ligand (Y) present in the complex (4) to form a substantially insoluble silver salt AgY which precipitates out of the reaction medium. Any suitable quantity of AgX (7) may be used, although it is preferred that the molar ratio of the complex of formula (4):AgX (7) is from about 1:1.90 to about 1:2.2, such as about 1:2.0.

The reaction mixture of step (a) is typically protected from light and may be stirred at room temperature for a period of time (such as about 30-60 minutes).

The product of step (a) may then reacted with the monodentate biaryl ligand of formula (5) to form a complex of formula (1). Alternatively, the product of step (a) may be reacted with the bi-heteroaryl tertiary phosphine ligand (8) to form a complex of formula (3). In one embodiment, the reaction mixture comprising the product of step (a) may be transferred (e.g. by cannula) from one flask to another flask containing the ligand (5) or (8). In another embodiment, the product of step (a) may be filtered in situ (e.g. using a

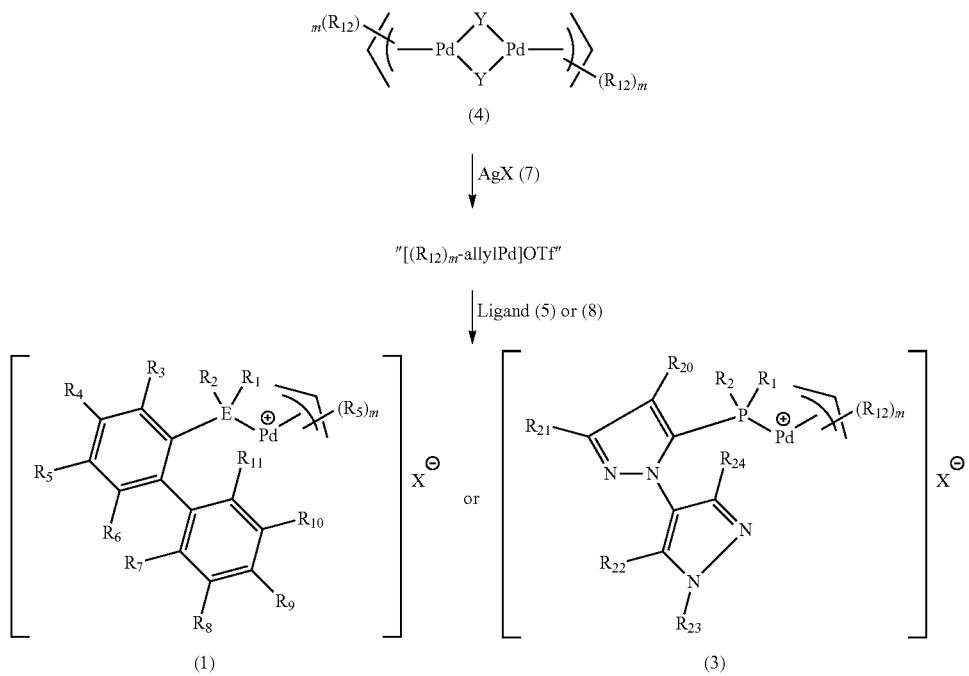

The complex of formula (4) and silver salt (7) may be combined in a solvent. In this case, the solvent is any suitable aprotic solvent or combination of aprotic solvents. Examples of aprotic solvents are toluene, benzene, tetrahydrofuran (THF), 2-methyltetrahydrofuran (2-MeTHF), dichloromethane (DCM), dioxane, acetone, acetonitrile, dimethylformamide (DMF), N-methylpyrrolidine (NMP), dimethylacetamide (DMAc), methyltertbutylether (MTBE), diethylether, hexane, heptane, pentane or ethylacetate. Preferred solvents are THF, 2-methyltetrahydrofuran, toluene, Schlenk frit) or under inert conditions. Additional solvent may be used to transfer the contents of one flask to another, for example, to rinse the flask or frit. Regardless of which embodiment is used, the insoluble silver salt AgY remains in the first flask and is not transferred to the second.

Alternatively, the ligand (either as a solid or in solution) may be added to the reaction mixture of step (a).

Any suitable quantity of ligand may be used, although it is preferred that the molar ratio of the complex of formula (4):ligand is from about 1:1.90 to about 1:2.5, such as about 1:2.0 to about 1:2.2 e.g. about 1:2.0. If desired the ligand may be used in the form of a salt, for example, a tetrafluoroborate salt. The ligand may be that of formula (5) or (8).

The reaction is preferably carried out under an inert atmosphere, such as nitrogen or argon.

The process may be carried out at a temperature in the range of about −10° C. to about 60° C., preferably about 0° C. to about 35° C. and more preferably at about room temperature (rt) (i.e. about 15° C. to about 30° C.). It is preferred that the temperature is maintained below the decomposition temperature and so when the complexes of formula (1), (3) or the product of step (a) are known to decompose within the temperature ranges given above, the temperature should be maintained below the decomposition temperature.

The reaction may be carried out for a period of from about several minutes to about 24 hours. Usually the reaction is complete in about 2.5 hours for a laboratory scale reaction. On completion, a proportion of the solvent may be evaporated if desired prior to recovery of the complex. Furthermore, if desired an anti-solvent (e.g. an alkane, such as pentane or hexane) may be used to precipitate the complex from the solvent. The complex product may be recovered directly by filtering, decanting or centrifuging.

Howsoever the complex is recovered, the separated complex may be washed and then dried. Drying may be performed using known methods, for example at temperatures in the range 10-60° C. and preferably 20-40° C. under 1-30 mbar vacuum for 1 hour to 5 days. If desired the complex may be recrystallized, although in some embodiments this may not be required as analytically pure product can be obtained without additional purification.

In certain embodiments, the complexes may be prepared in high yield. In certain embodiments, the complexes may be prepared having a high purity. In certain embodiments, the complexes are highly active catalysts. In certain embodiments, the complexes are stable to air and moisture at ambient temperatures.

Application studies of the complexes indicate that they may be easily activated under mild conditions. For example, allyl complexes may be typically activated at >60° C., and the crotyl and cinnamyl complexes may be activated readily at room temperature. If desired, however, the complexes of the present invention may be used in reactions at higher temperatures (for example, ≥ about 60° C. to ≤ about 150° C.

Without wishing to be bound by theory, it is believed that the complexes activate to form an LPd(0) species (L=phosphine ligand). Relatively benign substituted olefin by-products may also be produced on activation of the complexes. It is proposed that the enhanced reactivity of the cationic complexes of the invention (e.g. when X⁻ is OTf) vs neutral (Cl) complexes could be as a consequence of the increased electrophilicity of the cationic complexes, and/or the destabilization of a non-productive μ-allyl-bridged species with a more labile counterion. In this respect, the active "LPd(0)" species (L=ligand) may be consumed by comproportionation with the yet unreacted complex of formula (1) or (3) to form dimer complexes. The suppression of the comproportionation process may be caused by the dimer complexes becoming increasingly destabilized with increasing ligand size, substitution on the allyl group due to steric strain, and/or the use of a more labile counterion thereby retarding their propensity to form. Additionally, the fast rate of oxidative addition that the L-Pd(0) complexes exhibit (e.g. when L=biarylphosphine) should rapidly draw the active L-Pd(0) into the catalytic cycle, thus, disfavouring the non-productive comproportionation process. These mechanisms are illustrated below for a particular π-allyl complex where L is a ligand of formula (5) or (8), X is OTf⁻ and m is 1.

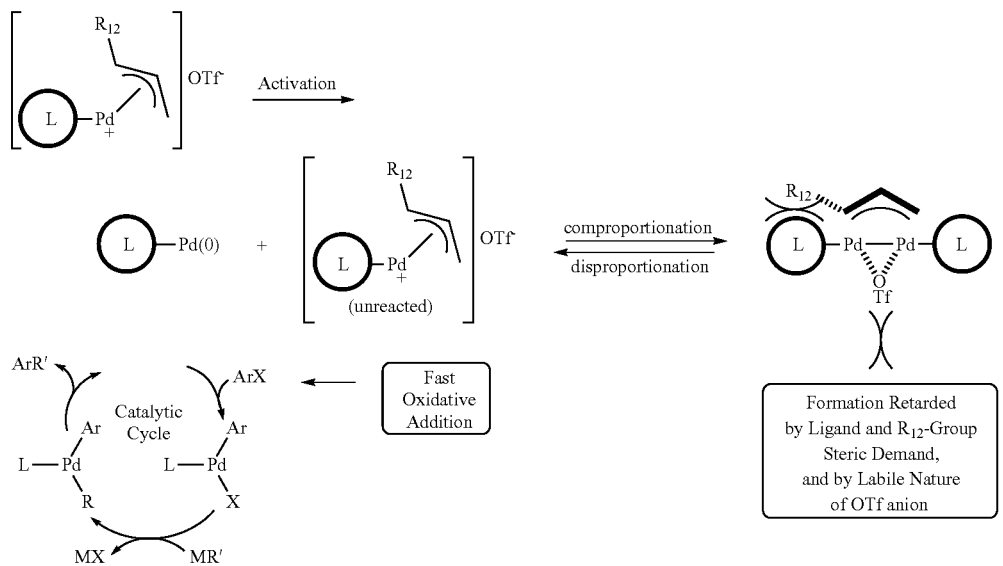

The catalysts of the present invention may be used for carbon-carbon coupling reactions. Examples of carbon-carbon coupling reactions include Heck, Suzuki, Sonogashira or Negishi reactions, ketone α-arylation reactions, aldehyde α-arylation reactions and allylic substitution reactions. The catalysts of the present invention may also be used for carbon-heteroatom coupling reactions, such as carbon-nitrogen coupling reactions (i.e. Buchwald-Hartwig reaction), or carbon-oxygen or carbon-sulfur coupling reactions. It is also envisaged that the complexes of formulae (1) or (3) may be suitable for polymerisation reactions.

In another aspect, the invention provides a process for carrying out a carbon-carbon coupling reaction in the presence of a catalyst, the process comprising the use of a complex of formula (1) as defined above or a complex of formula (3) as defined above.

In one embodiment, the process comprises the use of a complex of formula (1) as defined any one of claims 1 to 15. In another embodiment, the process comprises the use of a complex of formula (3) as defined in any one of claims 16 to 25.

In another aspect, the invention provides a process for carrying out a carbon-heteroatom coupling reaction in the presence of a catalyst, the process comprising the use of a complex of formula (1) as defined above or a complex of formula (3) as defined above.

In one embodiment, the process comprises the use of a complex of formula (1) as defined any one of claims 1 to 15. In another embodiment, the process comprises the use of a complex of formula (3) as defined in any one of claims 16 to 25.

In another aspect, the invention provides the use of a complex of formula (1) as defined above or a complex of formula (3) as defined above as a catalyst in carbon-carbon coupling reactions.

In one embodiment, the complex of formula (1) is as defined in any one of claims 1 to 15. In another embodiment, the complex of formula (3) is as defined in any one of claims 16 to 25.

In another aspect, the invention provides the use of a complex of formula (1) as defined above or a complex of formula (3) as defined above as a catalyst in carbon-heteroatom coupling reactions.

In one embodiment, the complex of formula (1) is as defined in any one of claims 1 to 15. In another embodiment, the complex of formula (3) is as defined in any one of claims 16 to 25.

Embodiments and/or optional features of the invention have been described above. Any aspect of the invention may be combined with any other aspect of the invention, unless the context demands otherwise. Any of the embodiments or optional features of any aspect may be combined, singly or in combination, with any aspect of the invention, unless the context demands otherwise.

The invention will now be described by way of the following non-limiting examples and with reference to the following figures in which.

EXAMPLES

Figure 1:
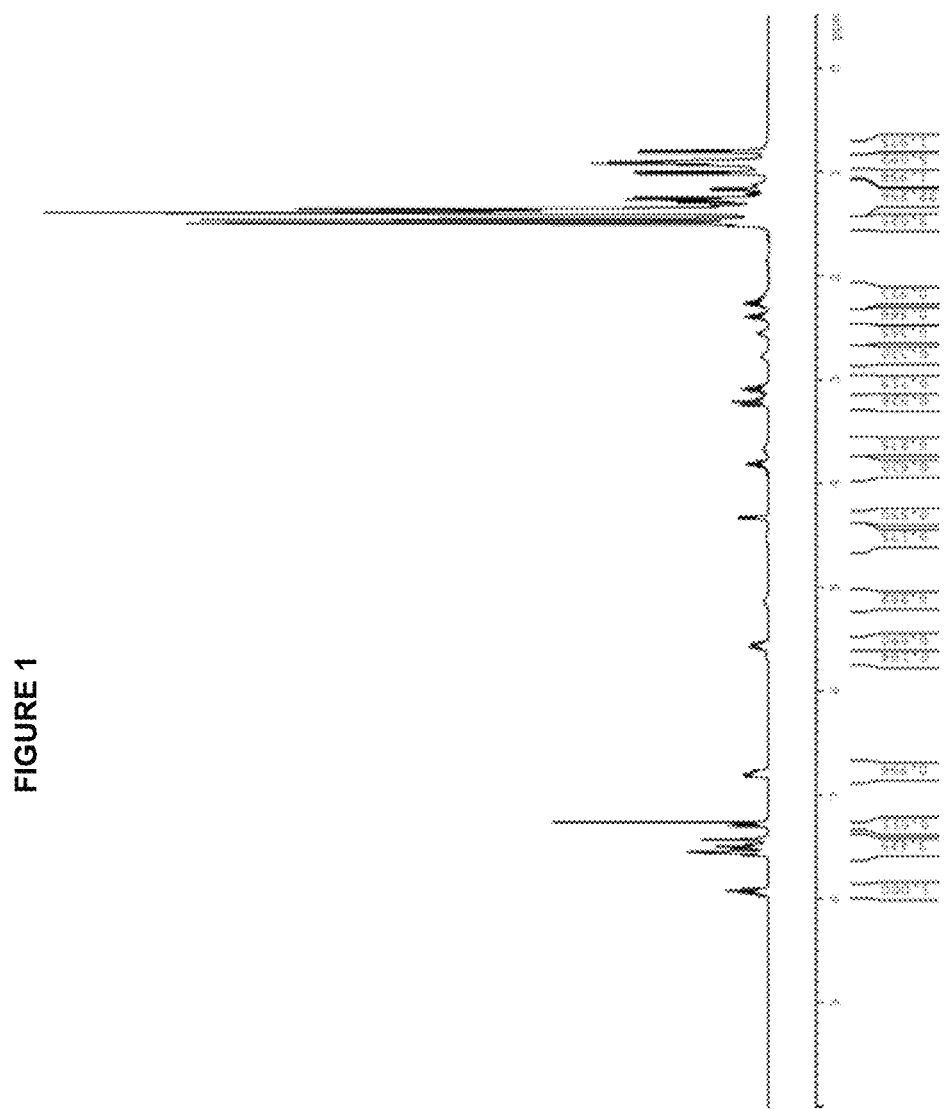
FIG. 1 is a $^1$H NMR spectrum of [(π-crotyl)Pd(tBuX-Phos)]OTf.

All solvents and reagents were purchased from commercial sources and used as received. All catalysts, ligands or precious metal precursors were obtained from Johnson Matthey Catalysis or Alfa Aesar. Flash chromatography was performed on a Teledyne ISCO CombiFlashRf using 12 g RediSepRf silica cartridges. $^{31}$P, $^1$H, $^{19}$F and $^{13}$C NMR spectra were recorded on a 400 MHz spectrometer, with chemical shifts reported relative to residual solvent as internal references (CDCl$_3$: 7.26 ppm for $^1$H NMR and 77.26 ppm for $^{13}$C NMR, C$_6$D$_6$: 7.16 ppm for $^1$H NMR and 128.06 ppm $^{13}$C NMR, DMSO-d6: 2.50 ppm for $^1$H NMR and 39.52 ppm for $^{13}$C NMR, toluene-d8: 2.08 ppm for $^1$H NMR and 20.43 ppm for $^{13}$C NMR), unless otherwise stated, while $^{31}$P{$^1$H} NMR spectra were externally referenced to 85% H$_3$PO$_4$, and $^{19}$F NMR spectra were externally referenced to CFCl$_3$. The following abbreviations were used to explain the multiplicities: s=singlet, d=doublet, t=triplet, q=quartet, quint=quintet, sept=septet, m=multiplet, b=broad, app t=apparent triplet, app d=apparent doublet, br=broad. Elemental analyses were sent to Robertson Microlit Laboratories, Inc. All reactions were carried out in individual Schlenk flasks under a nitrogen atmosphere. The purity of the isolated products was >95% as determined by $^1$H NMR, GC/MS or elemental analysis, unless otherwise noted.

Crystallographic data were obtained at 120K on a APEX Bruker-AXS CCD X-ray diffractometer equipped with a monocap collimator. Structures were solved with SHELXTL software. These data was obtained from University of Delaware X-ray Crystallography Laboratory of the Department of Chemistry and Biochemistry.

General Procedure for the Preparation of [Pd(Optionally Substituted (R$_{12}$)$_n$-Allyl)(X)]$_2$ Complexes:

Distilled H$_2$O in a three-necked roundbottom flask is purged with nitrogen for 30 minutes. PdCl$_2$ and KCl are subsequently added to the flask and the solution is stirred at room temperature for 1 h. Then, optionally substituted (R$_4$)$_n$-allyl chloride is added and the resulting reaction mixture is stirred at room temperature overnight (18-20 hrs). The reaction is extracted with chloroform, and the aqueous layer washed with chloroform three times. The organic layers are combined, dried over MgSO$_4$, filtered and concentrated in vacuo. The crude product is recrystallised from chloroform and methyl tert-butyl ether, and the resulting solid is isolated by filtration and dried in vacuo.

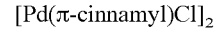

[Pd(π-cinnamyl)Cl]$_2$

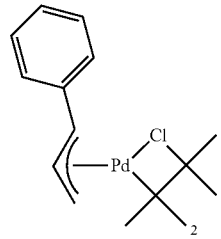

PdCl$_2$ (590 mg, 3.33 mmol); KCl (473 mg, 6.67 mmol); cinnamyl chloride (1.39 mL, 9.99 mmol); H$_2$O (83 mL). The dimer is obtained as a yellow solid.

[Pd(π-1-crotyl)Cl]₂

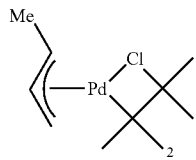

PdCl₂ (590 mg, 3.33 mmol); KCl (473 mg, 6.67 mmol); crotyl chloride (0.97 mL, 9.99 mmol); H₂O (83 mL). The dimer is obtained as a yellow solid.

[Pd(π-prenyl)Cl]₂

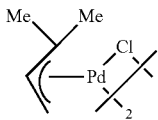

PdCl₂ (590 mg, 3.33 mmol); KCl (473 mg, 6.67 mmol); 1-chloride-3-methyl-2-butene (1.13 mL, 9.99 mmol); H₂O (83 mL). The dimer is obtained as a yellow solid.

[Pd(π-methallyl)Cl]₂

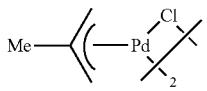

PdCl₂ (590 mg, 3.33 mmol); KCl (473 mg, 6.67 mmol); 3-chloride-2-methyl-1-propene (0.98 mL, 9.99 mmol); H₂O (83 mL). The dimer is obtained as a yellow solid (269 mg, 41%).

Example 1 (According to the Invention)

[(π-allyl)Pd(tBuBrettPhos)]OTf

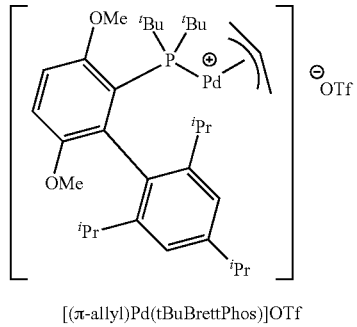

[(π-allyl)Pd(tBuBrettPhos)]OTf

A dry Schlenk flask is charged with 183 mg (0.50 mmol) of [(allyl)PdCl]₂ and 257 mg (1.0 mmol) of silver trifluoromethanesulfonate. A second dry Schlenk flask is fitted with a Schlenk frit and is charged with 485 mg (1.0 mmol) of tBuBrettPhos. The flasks are evacuated and backfilled with nitrogen. This evacuation/backfill cycle was repeated a total of three times. 10 mL of anhydrous THF is added to the first flask and the mixture is stirred for 30 min at room temperature (rt) while protecting from light. The mixture from flask one is then transferred via cannula through the Schlenk frit into the second flask to remove the AgCl. The frit is rinsed with an additional 10 mL of anhydrous THF. The mixture is stirred at room temperature for 2 hours, followed by the slow addition of 30 mL of hexanes to obtain a pale yellow precipitate. It is filtered, washed (2×10 mL of hexanes) and dried in vacuo to give 653 mg (0.84 mmol, 84%) of analytically pure (π-allyl)Pd(tBuBrettPhos)OTf as a slightly yellow solid; ¹H NMR (400 MHz, CDCl₃, δ): 7.45 (d, J=1.8 Hz, 1H), 7.28 (d, J=1.7 Hz, 1H), 7.07 (dd, J=2.9 Hz, 9.0 Hz, 1H), 6.96 (dd, J=2.9 Hz, 8.9 Hz, 1H), 5.52 (sept, J=7.1 Hz, 1H), 4.39 (app d, J=6.3 Hz, 1H), 3.83 (s, 3H), 3.35 (dd, J=9.2 Hz, 13.9 Hz, 1H), 3.32 (s, 3H), 2.97 (sept, J=6.9 Hz, 1H), 2.78 (app d, J=12.4 Hz, 1H), 2.54 (sept, J=6.7 Hz, 1H), 2.30-1.12 (m, 2H), 1.45-1.27 (m, 24H), 1.24 (dd, J=6.9 Hz, 11.8 Hz, 6H), 0.87 (d, J=6.9 Hz, 3H), 0.70 (d, J=6.9 Hz, 3H); ¹³C NMR (100 MHz, CDCl₃, δ): 156.3, 154.6 (2 peaks), 154.5, 152.2, 151.5, 136.5, 136.2, 125.8, 125.7, 125.6, 125.4, 125.2, 122.6, 119.7, 119.6, 119.4, 116.2, 115.5 (2 peaks), 112.8 (2 peaks), 112.0 (2 peaks), 99.8, 99.5, 58.4 (2 peaks), 54.7, 54.6, 39.9, 39.8, 39.3, 39.1, 34.0, 32.1, 32.0, 31.9, 31.7, 31.6 (2 peaks), 25.7, 25.5, 24.6, 24.5, 24.2 [Observed complexity due to C—F and C—P coupling]; ¹⁹F NMR (372 MHz, CDCl₃, δ): −77.9 (s, 3F); ³¹P NMR (162 MHz, CDCl₃, δ): 86.2; Anal. calcd. for C₃₅H₅₄O₅F₃PSPd: C, 53.81; H, 6.97. Found C, 53.81; H, 7.10.

Example 2

The following complexes are prepared using substantially the same procedure of Example 1.

[(π-allyl)Pd(tBuXPhos)]OTf

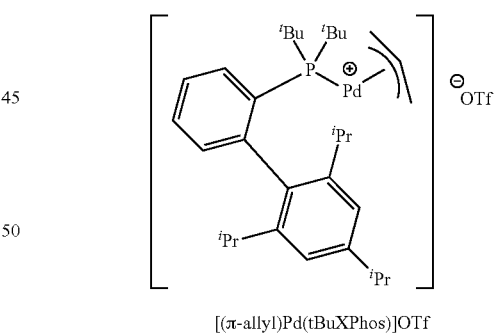

[(π-allyl)Pd(tBuXPhos)]OTf

[(allyl)PdCl]₂ (183 mg, 0.50 mmol); AgOTf (257 mg, 1.00 mmol); tBuXPhos (425 mg, 1.00 mmol); THF (10.0 mL); 2 h. Product obtained as a slightly yellow solid (708 mg, 98%); ¹H NMR (400 MHz, CDCl₃, δ): 7.92 (t, J=7.3 Hz, 1H), 7.59-7.47 (m, 3H), 7.42-7.40 (m, 1H), 6.79 (dd, J=3.2 Hz, 7.5 Hz, 1H), 5.72 (sept, J=7.2 Hz, 1H), 4.49 (d, J=6.7 Hz, 1H), 3.52 (dd, J=9.0 Hz, 14.0 Hz, 1H), 3.03 (quint, J=7.1 Hz, 1H), 2.93 (d, J=12.9 Hz, 1H), 2.67-2.62 (m, 1H), 2.50 (quint, J=7.1 Hz, 1H), 2.26 (quint, J=6.9 Hz, 1H), 1.49-1.40 (m, 9H), 1.40-1.28 (m, 21H), 0.96 (d, J=6.7 Hz, 3H), 0.88 (d, J=6.7 Hz, 3H); ¹³C NMR (100 MHz, CDCl₃, δ): 153.6, 152.7, 149.2, 146.0, 145.8, 135.1 (2 peaks), 134.9, 133.7, 133.6, 131.7, 131.6, 128.3, 128.2, 126.6, 126.2, 125.8, 122.6, 120.3 (2 peaks), 120.1 (2 peaks), 119.4, 116.2, 101.3, 101.1, 55.5, 38.3 (2 peaks), 38.2, 38.1, 33.9, 32.0, 31.7, 31.2, 31.1, 30.9, 30.8, 25.9, 25.4, 24.9, 24.5 (2 peaks), 24.1 [Observed complexity due to C—F and C—P coupling]; $^{19}$F NMR (372 MHz, CDCl$_3$, δ): −78.1 (s, 3F); $^{31}$P NMR (162 MHz, CDCl$_3$, δ): 70.1; Anal. calcd. for C$_{33}$H$_{50}$O$_3$F$_3$PSPd: C, 54.96; H, 6.99. Found C, 54.84; H, 7.13.

[(π-crotyl)Pd(tBuXPhos)]OTf

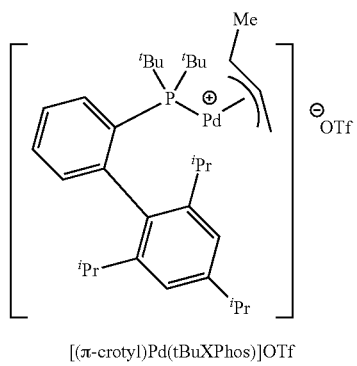

[(π-crotyl)Pd(tBuXPhos)]OTf

[(crotyl)PdCl]$_2$ (197 mg, 0.50 mmol); AgOTf (257 mg, 1.00 mmol); tBuXPhos (425 mg, 1.00 mmol); 2-MeTHF (10.0 mL); 2 h. Product obtained as a slightly yellow solid (722 mg, 98%); The spectral properties are complicated due to the presence of isomers. $^1$H NMR (400 MHz, CDCl$_3$, δ): Complex spectrum, see FIG. 1; $^{13}$C NMR (100 MHz, CDCl$_3$, δ): 153.4, 152.3, 152.0, 146.4, 146.2, 146.0, 145.8, 144.1, 135.0, 134.9, 134.7, 134.4, 134.1, 133.7, 133.6, 133.3, 133.2, 131.5 (2 peaks), 131.4 (2 peaks), 128.1 (2 peaks), 128.0, 127.1, 126.1, 125.7, 124.6, 124.1, 122.9, 122.8, 122.5, 121.7, 121.4, 119.3, 112.9 (2 peaks), 48.3, 38.9, 38.8, 38.3, 38.1, 37.5, 37.3, 33.8, 33.5, 32.0, 31.9, 31.7, 31.6, 31.3, 31.1 (2 peaks), 31.0 (2 peaks), 30.7 (2 peaks), 26.2, 25.6, 25.5, 25.4, 25.1, 24.9, 24.3, 24.2, 24.0 (2 peaks), 23.7, 23.4, 22.8, 16.4 (2 peaks) [Observed complexity due to C—F and C—P coupling]; $^{19}$F NMR (372 MHz, CDCl$_3$, δ): −77.9 (s, 3F); $^{31}$P NMR (162 MHz, CDCl$_3$, δ): 72.2, 71.7, 66.7; Anal. calcd. for C$_{34}$H$_{52}$O$_3$F$_3$PSPd: C, 55.54; H, 7.13. Found C, 55.66; H, 6.99.

[(π-cinnamyl)Pd(tBuXPhos)]OTf

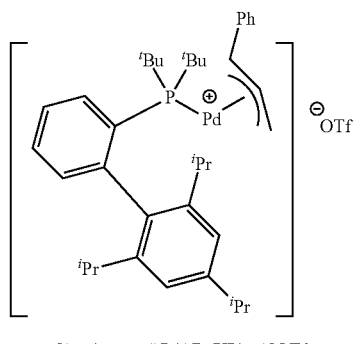

[(π-cinnamyl)Pd(tBuXPhos)]OTf

Figure 2:
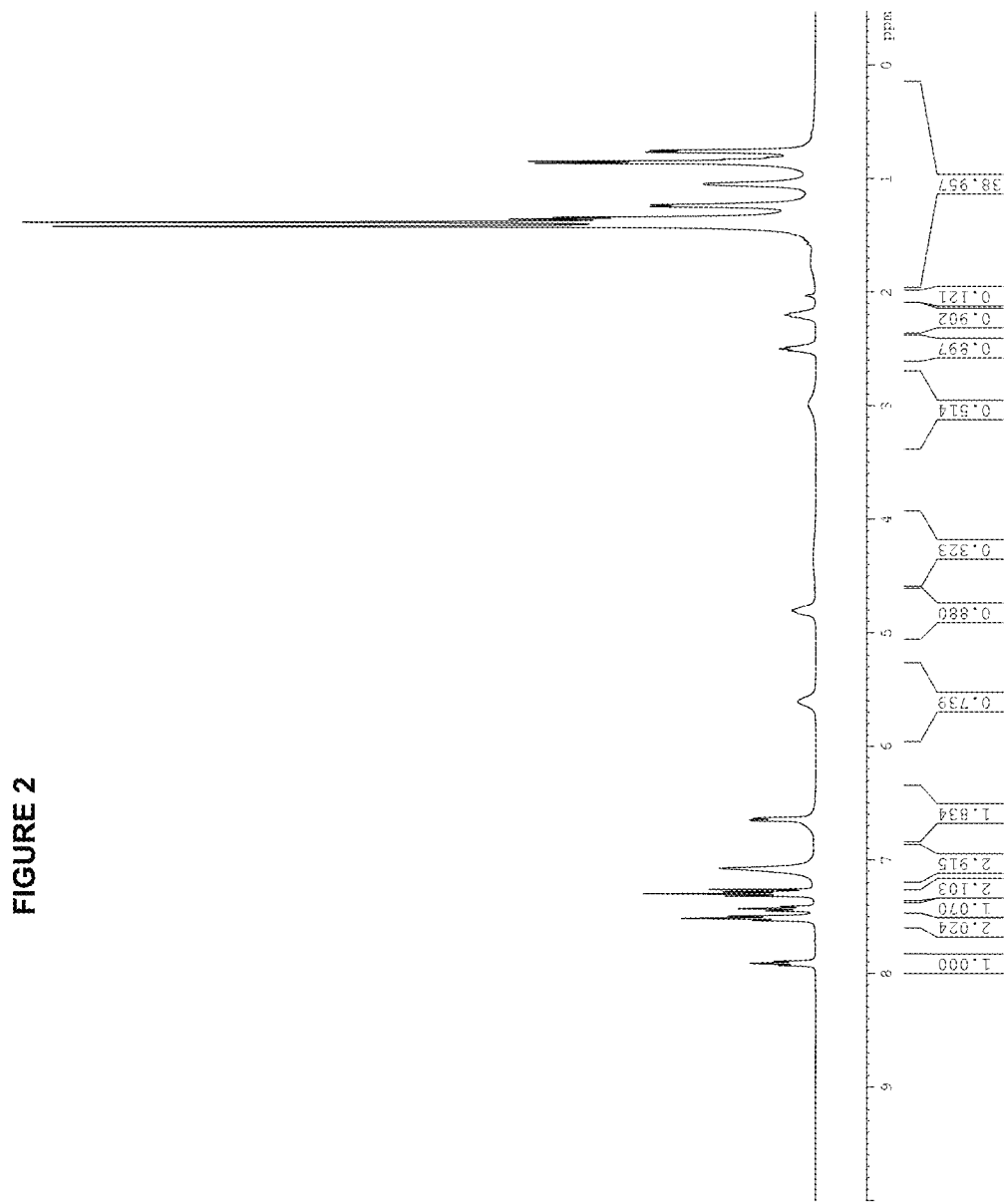
FIG. 2 is a $^1$H NMR spectrum of [(π-cinnamyl)Pd(tBuX-Phos)]OTf.

[(cinnamyl)PdCl]$_2$ (259 mg, 0.50 mmol); AgOTf (257 mg, 1.00 mmol); tBuXPhos (425 mg, 1.00 mmol); 2-MeTHF (10.0 mL); 2 h. Product obtained as a yellow solid (725 mg, 91%); $^1$H NMR (400 MHz, CDCl$_3$, δ): Complex spectrum, see FIG. 2; $^{13}$C NMR (100 MHz, CDCl$_3$, δ): 153.1, 151.5, 146.8, 146.6, 135.4, 135.1, 135.0, 134.1, 133.6, 133.5, 131.5, 130.3 (2 peaks), 129.6 (2 peaks), 128.1, 128.0, 125.2, 123.3, 122.6, 119.4, 118.9, 116.2, 110.2, 39.3, 39.1, 32.1, 31.5, 31.3 (2 peaks), 31.0, 25.7, 25.5, 24.9, 24.8, 24.4, 22.6, 22.5, 14.1 [Observed complexity due to C—F and C—P coupling]; $^{19}$F NMR (372 MHz, CDCl$_3$, δ): −78.6 (s, 3F); $^{31}$P NMR (162 MHz, CDCl$_3$, δ): 76.0; Anal. calcd. for C$_{39}$H$_{54}$O$_3$F$_3$PSPd: C, 58.75; H, 6.83. Found C, 58.81; H, 6.76.

[(π-allyl)Pd(Me$_4$tBuXPhos)]OTf

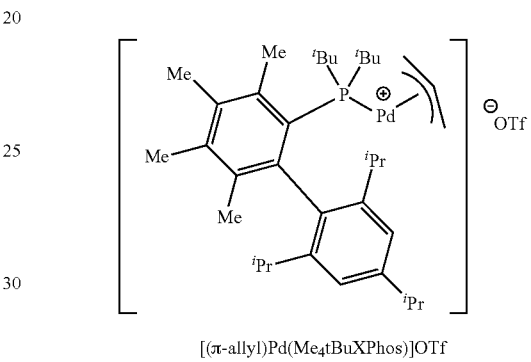

[(π-allyl)Pd(Me$_4$tBuXPhos)]OTf

[(allyl)PdCl]$_2$ (183 mg, 0.50 mmol); AgOTf (257 mg, 1.00 mmol); Me$_4$tBuXPhos (481 mg, 1.00 mmol); THF (10.0 mL); 2 h. Product obtained as a pale yellow solid (727 mg, 94%), product contains a trace amount of residual THF (~5 mol % as judged by $^1$H NMR); $^1$H NMR (400 MHz, CDCl$_3$, δ): 7.42 (s, 1H), 7.32 (s, 1H), 5.58 (sept, J=7.1 Hz, 1H), 4.53 (d, J=6.5 Hz, 1H), 3.31 (dd, J=9.5, 13.4 Hz, 1H), 3.00 (sept, J=7.3 Hz, 1H), 2.91 (d, J=12.8 Hz, 1H), 2.61 (sept, J=6.8 Hz, 1H), 2.60 (s, 3H), 2.31 (sept, J=6.6 Hz, 1H), 2.25 (s, 3H), 2.16-2.08 (m, 4H), 1.52-1.37 (m, 18H), 1.32 (d, J=7.0 Hz, 6H), 1.24 (t, J=7.6 Hz, 6H), 0.88 (d, J=6.8 Hz, 3H), 0.82 (s, 3H), 0.74 (d, J=6.6 Hz, 3H), peaks attributable to THF were observed at 3.76 and 1.85 ppm; $^{13}$C NMR (100 MHz, CDCl$_3$, δ): 155.1, 154.6, 151.4, 143.3, 143.0, 141.5 (2 peaks), 139.2, 138.5, 138.4, 137.1, 137.0, 133.6, 133.4, 125.8, 125.6, 125.5, 122.6, 120.0, 119.9, 119.4, 116.2, 116.1, 98.3, 98.0, 62.7 (2 peaks), 40.9, 40.8, 40.1, 40.0, 34.0, 33.4 (2 peaks), 32.9 (2 peaks), 32.2, 32.0, 26.9, 26.3, 26.2, 24.8, 24.6, 24.3 (2 peaks), 18.7, 17.5, 17.3 [Observed complexity due to C—F and C—P coupling], peaks attributable to THF were observed at 67.9 and 25.6 ppm; $^{19}$F NMR (372 MHz, CDCl$_3$, δ): −78.1 (s, 3F); $^{31}$P NMR (162 MHz, CDCl$_3$, δ): 93.5; Anal. calcd. for C$_{37}$H$_{58}$O$_3$F$_3$PSPd: C, 57.17; H, 7.52. Found C, 57.19; H, 7.64.

[(π-allyl)Pd(RockPhos)]OTf

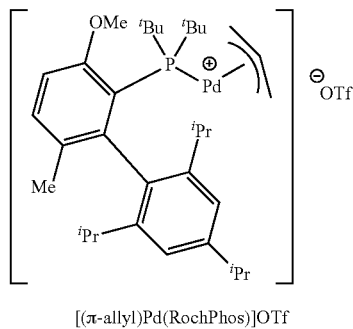

[(π-allyl)Pd(RochPhos)]OTf

[(allyl)PdCl]$_2$ (183 mg, 0.50 mmol); AgOTf (257 mg, 1.00 mmol); RockPhos (469 mg, 1.00 mmol); THF (10.0 mL); 2 h. Product obtained as a yellow solid (744 mg, 97%), product contains a trace amount of residual THF (~8 mol % as judged by $^1$H NMR); $^1$H NMR (400 MHz, CDCl$_3$, δ): 7.44 (d, J=1.3 Hz, 1H), 7.37 (d, J=1.3 Hz, 1H), 7.32 (d, J=8.5 Hz, 1H), 7.01 (dd, J=2.2, 8.4 Hz, 1H), 5.57 (sept, J=6.9 Hz, 1H), 4.44 (d, J=6.6 Hz, 1H), 3.88 (s, 3H), 3.38 (dd, J=9.4, 13.7 Hz, 1H), 3.01 (sept, J=7.1 Hz, 1H), 2.86 (d, J=12.7 Hz, 1H), 2.63 (sept, J=6.7 Hz, 1H), 2.31 (sept, J=6.8 Hz, 1H), 2.23 (dt, J=2.3, 7.5 Hz, 1H), 1.45-1.20 (m, 30H) 1.08 (s, 3H), 0.97 (d, J=6.5 Hz, 3H), 0.84 (d, J=6.8 Hz, 3H), peaks attributable to THF were observed at 3.76 and 1.85 ppm; $^{13}$C NMR (100 MHz, CDCl$_3$, δ): [Observed complexity due to C—F and C—P coupling], peaks attributable to THF were observed at 67.9 and 25.6 ppm; $^{19}$F NMR (372 MHz, CDCl$_3$, δ): -78.2 (s, 3F); $^{31}$P NMR (162 MHz, CDCl$_3$, δ): 84.8; Anal. calcd. for C$_{35}$H$_{54}$O$_4$F$_3$PSPd: C, 54.93; H, 7.11. Found C, 54.92; H, 7.25.

[(π-allyl)Pd(BippyPhos)]OTf

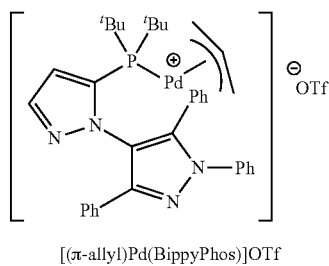

[(π-allyl)Pd(BippyPhos)]OTf

[(allyl)PdCl]$_2$ (183 mg, 0.50 mmol); AgOTf (257 mg, 1.00 mmol); BippyPhos (507 mg, 1.00 mmol); THF (10.0 mL); 2 h. Product obtained as a pale yellow solid (786 mg, 91%), and is a ⅔ MTBE solvate (MTBE/hexanes used to in the precipitation); $^1$H NMR (400 MHz, CDCl$_3$, δ): (2 isomers present in ~6:4 ratio) 8.15-8.05 (m, 1H), 7.49-7.08 (m, 15H), 7.71-7.60 (m, 1H), 6.10-5.79 (m, 1H), 4.52-4.29 (m, 2H), 4.06-3.96 (m, 0.4H), 3.85-3.75 (m, 0.6H), 3.37-3.30 (m, 0.4H), 3.02-2.92 (m, 0.6H), 0.91-0.50 (m, 18H), peaks attributable to MTBE were observed at 3.10 and 1.05 ppm; $^{13}$C NMR (100 MHz, CDCl$_3$, δ): 156.4, 154.8, 150.5, 148.0, 146.3 (2 peaks), 146.1, 146.0, 141.9, 141.5, 137.7, 137.6, 131.2, 130.5, 130.3, 129.8, 129.7, 129.4 (2 peaks), 129.2, 129.1, 129.0, 128.9, 127.9, 127.7, 125.6, 125.2, 124.6, 122.6 (2 peaks), 122.4, 121.8 (2 peaks), 119.2, 116.0, 114.9, 104.0, 103.9, 93.4, 93.2, 90.1, 89.9, 57.8, 56.9, 36.4, 36.2, 36.1 (2 peaks), 36.0, 35.9, 35.8, 29.0 (2 peaks), 28.9 (2 peaks), 28.5 (2 peaks) [Observed complexity due to C—F and C—P coupling], peaks attributable to MTBE were observed at 72.5, 49.2 and 26.8 ppm; $^{19}$F NMR (372 MHz, CDCl$_3$, δ): -80.0 (s, 3F); $^{31}$P NMR (162 MHz, CDCl$_3$, δ): 50.4, 49.5; Anal. calcd. for C$_{36}$H$_{40}$N$_4$O$_3$F$_3$PSPd.(⅔ C$_5$H$_{12}$O): C, 54.81; H, 5.61. Found C, 54.97; H, 5.70.

Example 3 (According to the Invention)

General Procedure

A dry Schlenk flask equipped with a Teflon-coated magnetic stir bar is charged with [(R-allyl)PdCl]$_2$ (0.50 mmol, 0.50 equiv) followed by AgOTf (257 mg, 1.00 mmol, 1.00 equiv). The flask is fitted with a rubber septum evacuated and backfilled with nitrogen. This evacuation/nitrogen backfill cycle is repeated two additional times. Solvent (10 mL THF or 2-MeTHF) is added and the reaction mixture is stirred at it for 30 min while protected from light. A second dry Schlenk flask is equipped with a magnetic stir bar, fitted with a Schlenk frit, and charged with the appropriate ligand (1.00 mmol, 1.00 equiv). The flask is fitted with a rubber septum and it is evacuated and backfilled with nitrogen. This evacuation/nitrogen backfill cycle is repeated two additional times. The solution from the first Schlenk flask is transferred via cannula through the Schlenk frit (to remove AgCl) and into the second Schlenk flask containing the ligand, rinsing with 5 mL of additional solvent (THF or 2-MeTHF). This mixture is stirred at it for 2 h. 30 mL of hexanes is then added to fully precipitate the product. The solid materials are then collected by suction filtration, washed with additional pentane (or hexanes), and dried in vacuo.

[(π-allyl)Pd(BrettPhos)]OTf

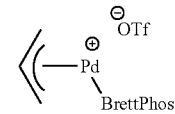

The general procedure is followed using 183 mg (0.50 mmol) of [(allyl)PdCl]$_2$, 257 mg (1.00 mmol) of AgOTf, 537 mg (1.00 mmol) of BrettPhos in anhydrous THF to give 803 mg (0.94 mmol, 94%) of the title compound as a yellow solid. The material contains ~3 wt % of THF.

$^1$H NMR (400 MHz, CDCl$_3$, δ): 7.34 (s, 1H), 7.23 (s, 1H), 7.07-6.98 (m, 1H), 6.96-6.87 (m, 1H), 5.45 (sept, J=7.52 Hz, 1H), 4.14 (d, J=6.8 Hz, 1H), 3.84 (s, 3H), 3.42 (dd, J=8.2, 13.1 Hz, 1H), 3.29 (s, 3H), 2.90 (sept, J=8.2 Hz, 1H), 2.79-2.63 (m, 1H), 2.59 (d, J=13.2 Hz, 1H), 2.55-2.41 (m, 1H), 2.40-2.25 (m, 2H), 2.14 (sept, J=7.8 Hz, 1H), 1.98-1.82 (m, 2H), 1.81-0.93 (m, 29H), 0.92-0.66 (m, 7H).

$^{13}$C NMR (100 MHz, CDCl$_3$, δ): 154.8 (2 peaks), 153.3, 151.4, 150.5, 135.0, 134.8, 125.6, 124.9, 124.8, 124.2, 123.9, 122.4, 119.5, 119.4, 119.3, 115.2, 113.7, 112.7 (2 peaks), 100.7, 100.5, 55.8, 54.7, 52.0, 38.5, 38.4, 38.3, 38.1, 33.7, 32.5, 31.5, 30.0, 27.2, 26.7, 26.6, 24.3, 24.0, 23.9, 23.8 [Observed complexity due to C—P and C—F coupling]; peaks attributable to THF are observed at 67.7 and 25.4.

$^{31}$P NMR (162 MHz, CDCl$_3$, δ): 51.4.

$^{19}$F NMR (376 MHz, CDCl$_3$, δ): -78.4 (s, 3F).

Anal. Calcd. for $C_{39}H_{58}F_3O_5PPdS$: C, 56.21; H, 7.02. Found: C, 56.46; H, 7.05.

[(π-crotyl)Pd(BrettPhos)]OTf

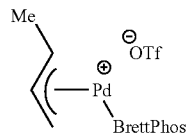

The general procedure is followed using 197 mg (0.50 mmol) of [(crotyl)PdCl]$_2$, 257 mg (1.00 mmol) of AgOTf, 537 mg (1.00 mmol) of BrettPhos in anhydrous THF to give 816 mg (0.96 mmol, 96%) of the title compound as a yellow solid. The material contains ~2 wt % of THF.

Figure 3:
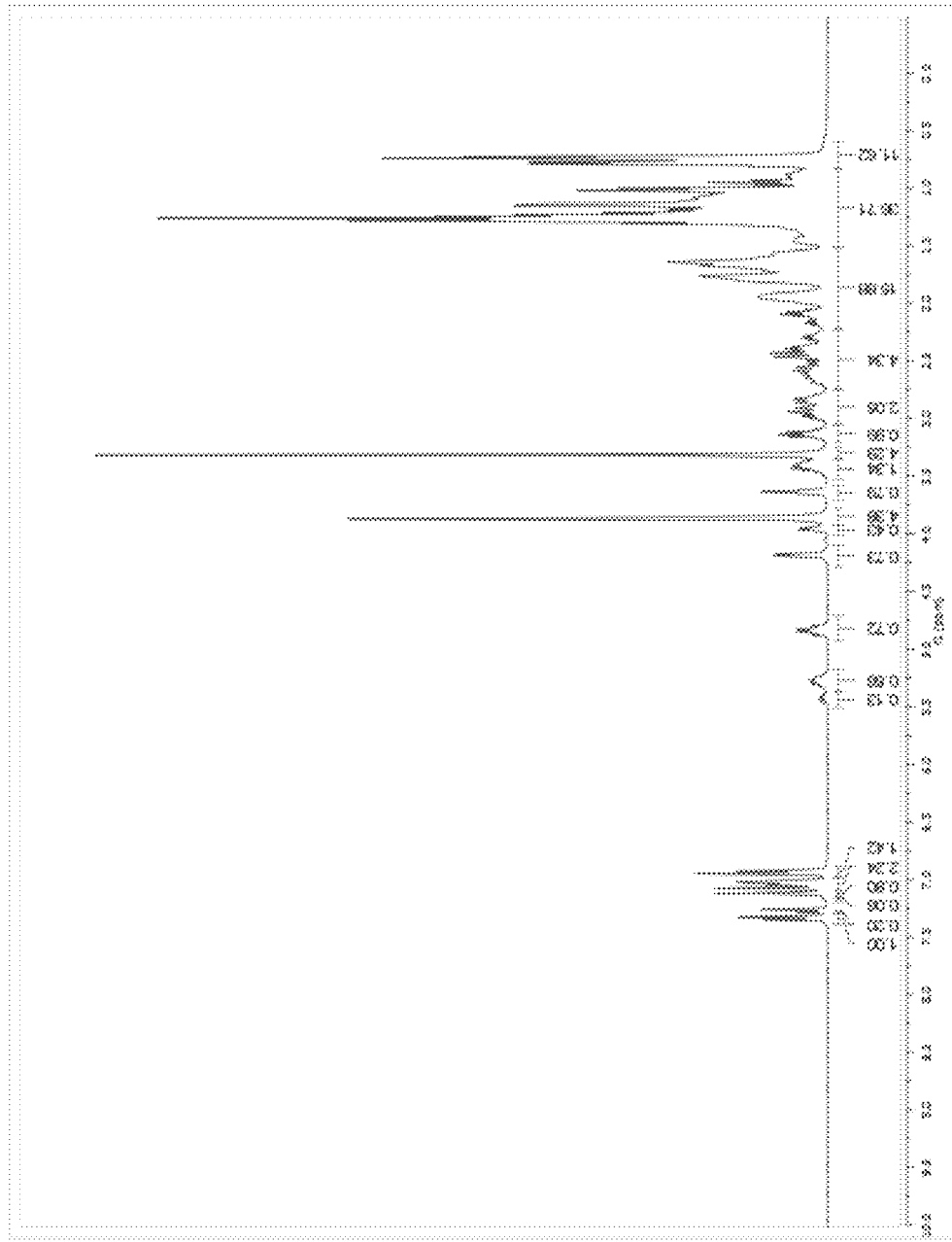
FIG. 3 is a $^1$H NMR spectrum of [(π-crotyl)Pd(BrettPhos)]OTf.
Figure 4:
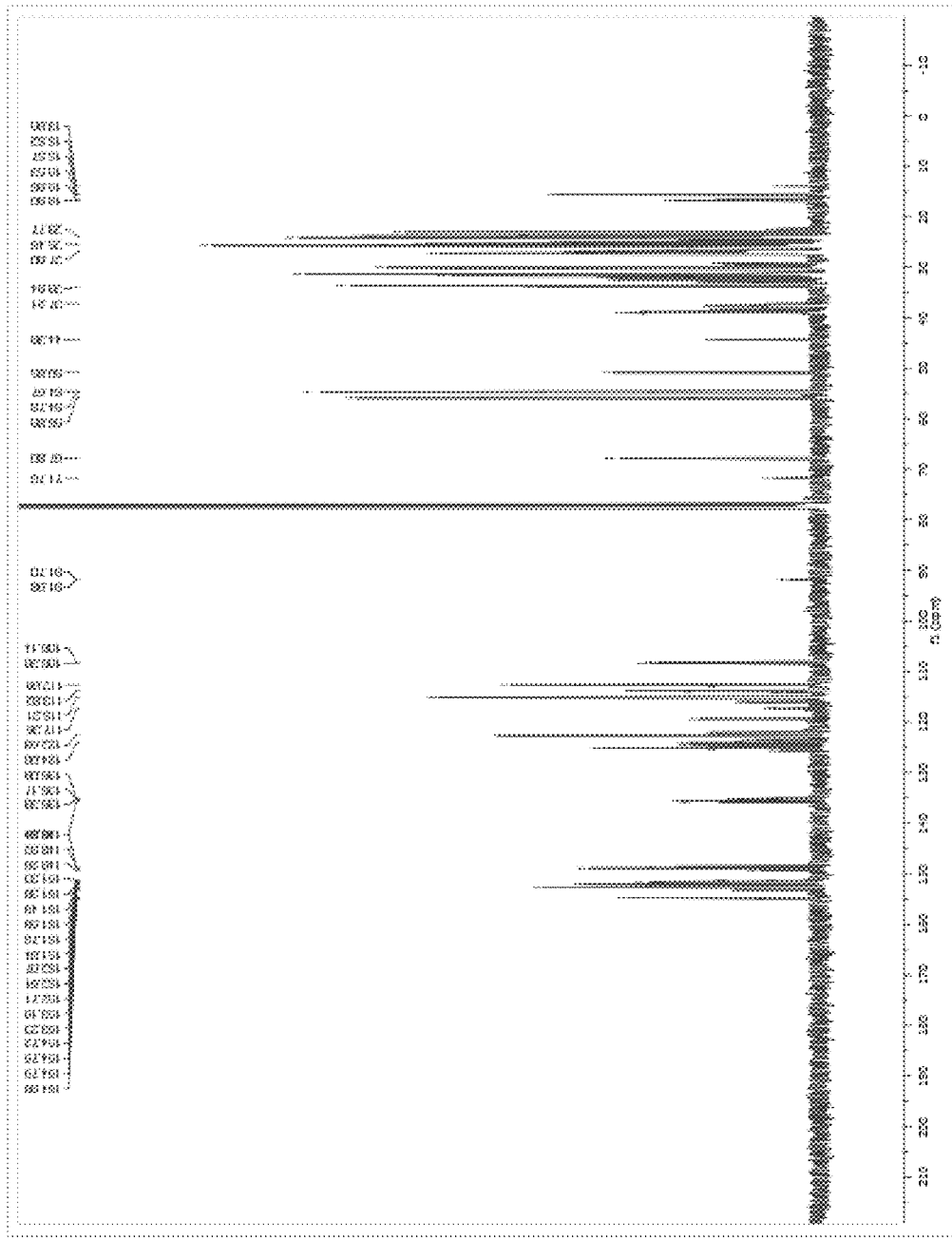
FIG. 4 is a $^{13}$C NMR spectrum of [(π-crotyl)Pd(BrettPhos)]OTf.

$^1$H NMR (400 MHz, CDCl$_3$, δ): complex spectrum—see FIG. 3.
$^{13}$C NMR (100 MHz, CDCl$_3$, δ): complex spectrum—see FIG. 4.
$^{31}$P NMR (162 MHz, CDCl$_3$, δ): 54.0, 52.2, 45.7, 43.3.
$^{19}$F NMR (376 MHz, CDCl$_3$, δ): −78.2 (s, 3F).
HRMS (ESI) m/z [M-OTf]$^+$ Calcd. for $C_{39}H_{60})_2$PPd: 697.3366. Found: 697.3384.

[(π-cinnamyl)Pd(BrettPhos)]OTf

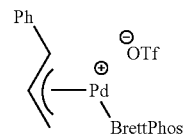

The general procedure is followed using 259 mg (0.50 mmol) of [(cinnamyl)PdCl]$_2$, 257 mg (1.00 mmol) of AgOTf, 537 mg (1.00 mmol) of BrettPhos in anhydrous 2-MeTHF to give 884 mg (0.97 mmol, 97%) of the title compound as a yellow solid.

Figure 5:
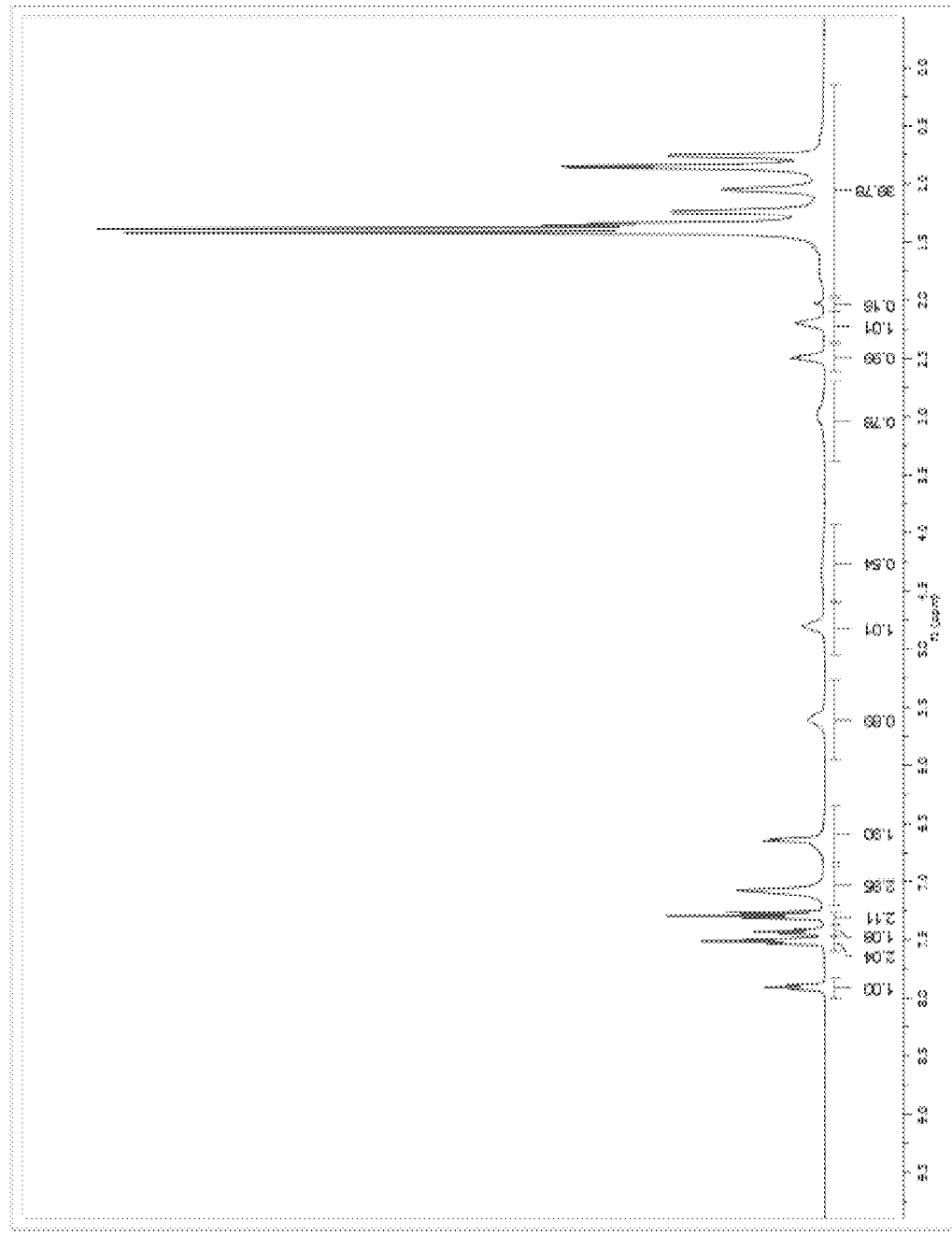
FIG. 5 is a $^1$H NMR spectrum of [(π-cinnamyl)Pd(BrettPhos)]OTf.
Figure 6:
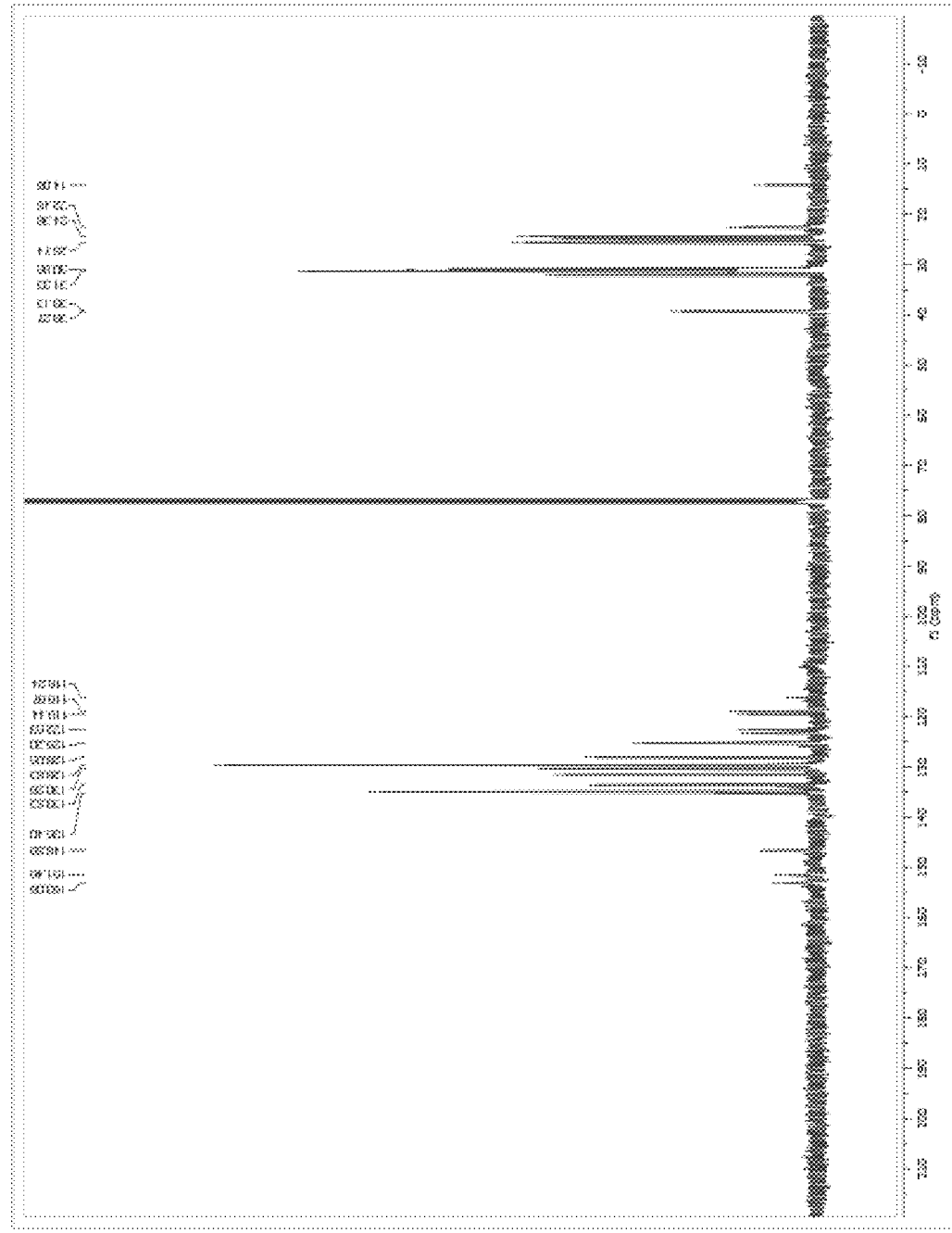
FIG. 6 is a $^{13}$C NMR spectrum of [(π-cinnamyl)Pd(BrettPhos)]OTf.

$^1$H NMR (400 MHz, CDCl$_3$, δ): complex spectrum—see FIG. 5.
$^{13}$C NMR (100 MHz, CDCl$_3$, δ): complex spectrum—see FIG. 6.
$^{31}$P NMR (162 MHz, CDCl$_3$, δ): 57.6, 39.5
$^{19}$F NMR (376 MHz, CDCl$_3$, δ): −78.1 (s, 3F).
Anal. Calcd. for $C_{45}H_{62}F_3O_5PPdS$: C, 59.43; H, 6.87. Found: C, 59.26; H, 6.68.

[(π-crotyl)Pd(tBuBrettPhos)]OTf

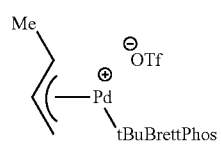

The general procedure is followed using 197 mg (0.50 mmol) of [(crotyl)PdCl]$_2$, 257 mg (1.00 mmol) of AgOTf, 485 mg (1.00 mmol) of tBuBrettPhos in anhydrous 2-MeTHF to give 784 mg (0.99 mmol, 99%) of the title compound as a light yellow solid.

Figure 7:
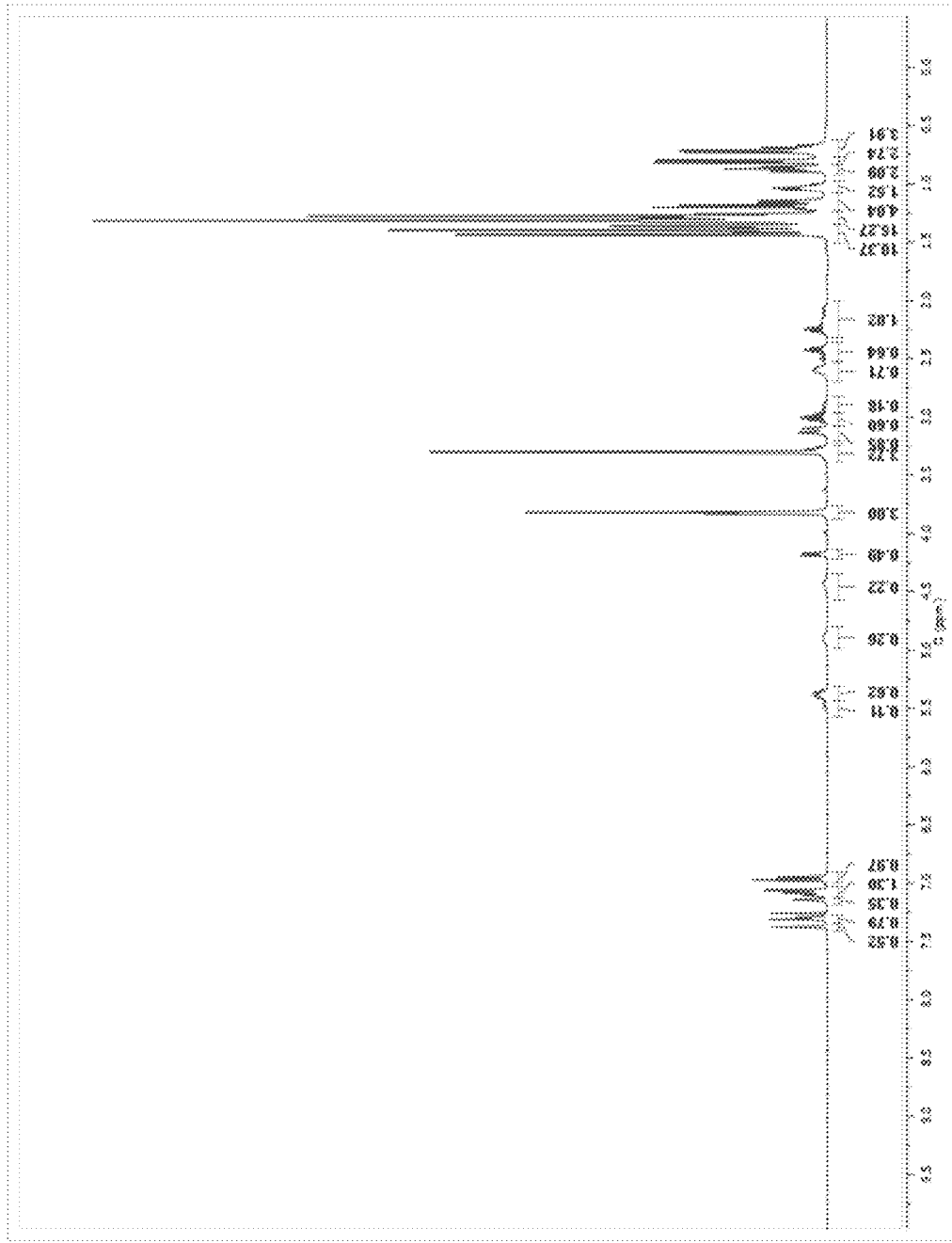
FIG. 7 is a $^1$H NMR spectrum of [(π-crotyl)Pd(tBu-BrettPhos)]OTf.
Figure 8:
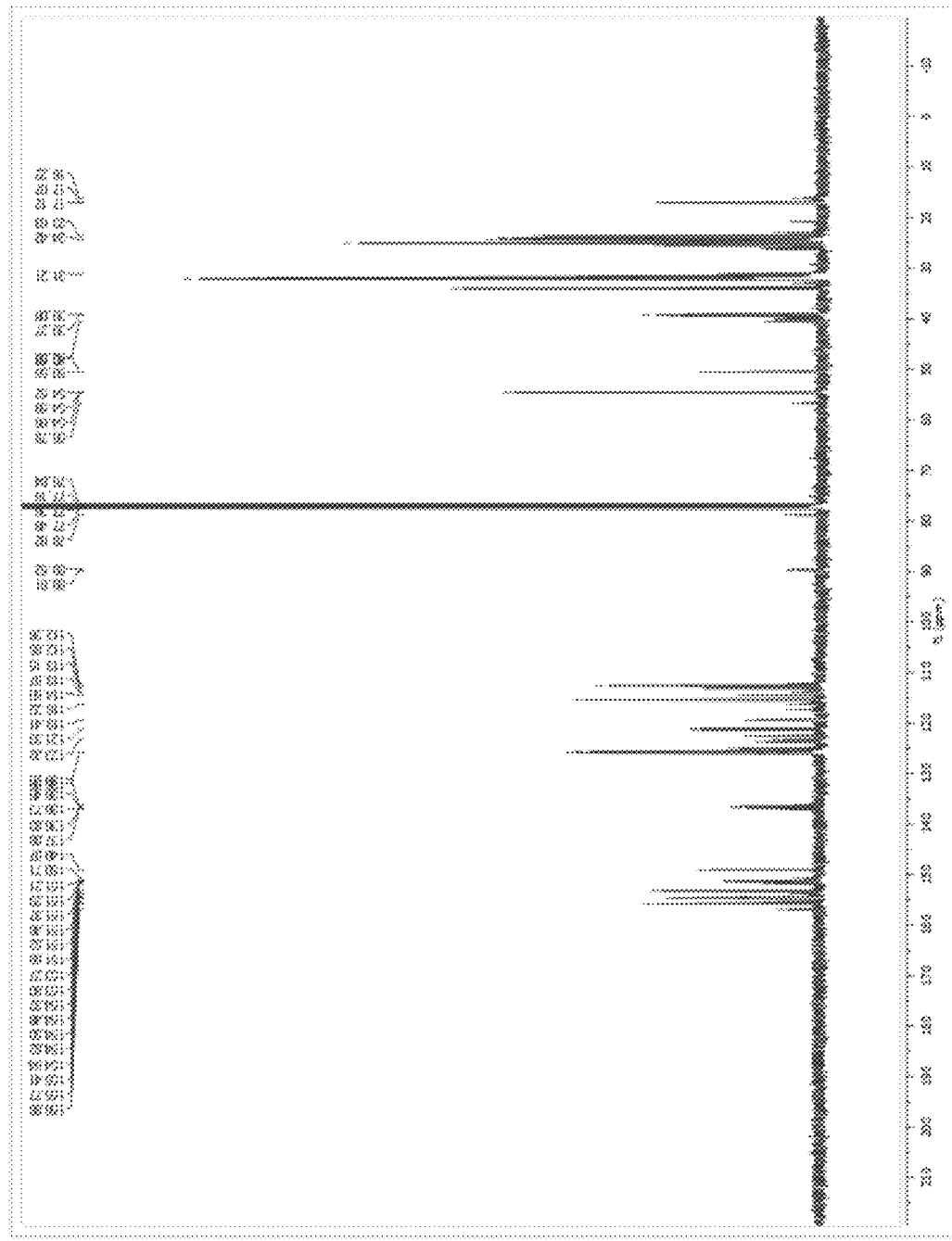
FIG. 8 is a $^{13}$C NMR spectrum of [(π-crotyl)Pd(tBu-BrettPhos)]OTf.

$^1$H NMR (400 MHz, CDCl$_3$, δ): Complex spectrum—see FIG. 7.
$^{13}$C NMR (100 MHz, CDCl$_3$, δ): Complex spectrum—see FIG. 8.
$^{31}$P NMR (162 MHz, CDCl$_3$, δ): 90.1, 88.4, 83.9.
$^{19}$F NMR (376 MHz, CDCl$_3$, δ): −78.0 (s, 3F).
Anal. Calcd. for $C_{36}H_{56}F_3O_5PPdS$: C, 54.37; H, 7.10. Found: C, 54.58; H, 7.01.

[(π-cinnamyl)Pd(tBuBrettPhos)]OTf

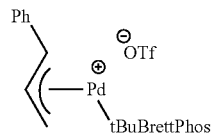

The general procedure is followed using 259 mg (0.50 mmol) of [(cinnamyl)PdCl]$_2$, 257 mg (1.00 mmol) of AgOTf, 485 mg (1.00 mmol) of tBuBrettPhos in anhydrous 2-MeTHF to give 812 mg (0.95 mmol, 95%) of the title compound as a dark yellow solid.

Figure 9:
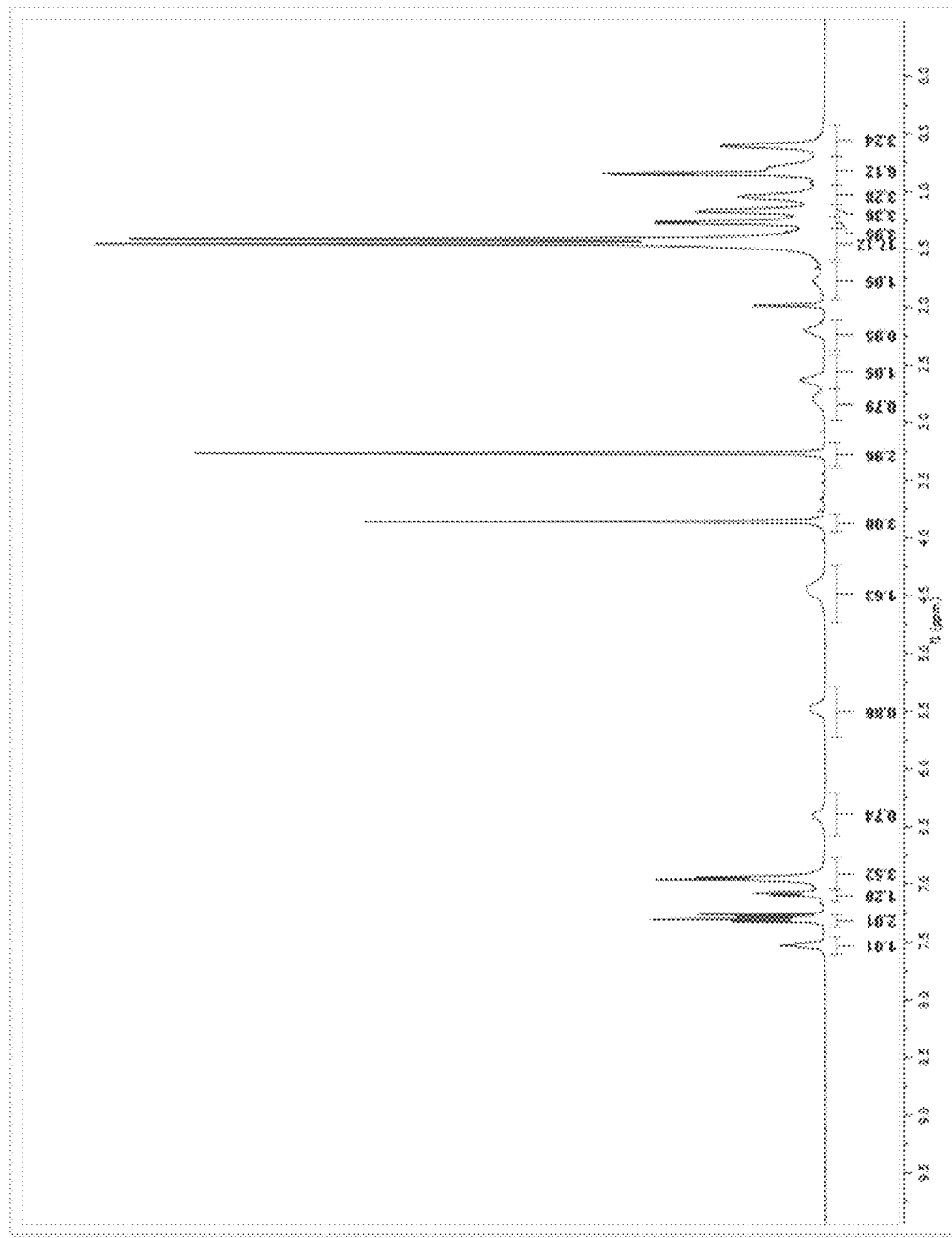
FIG. 9 is a $^1$H NMR spectrum of [(π-cinnamyl)Pd(tBu-BrettPhos)]OTf.
Figure 10:
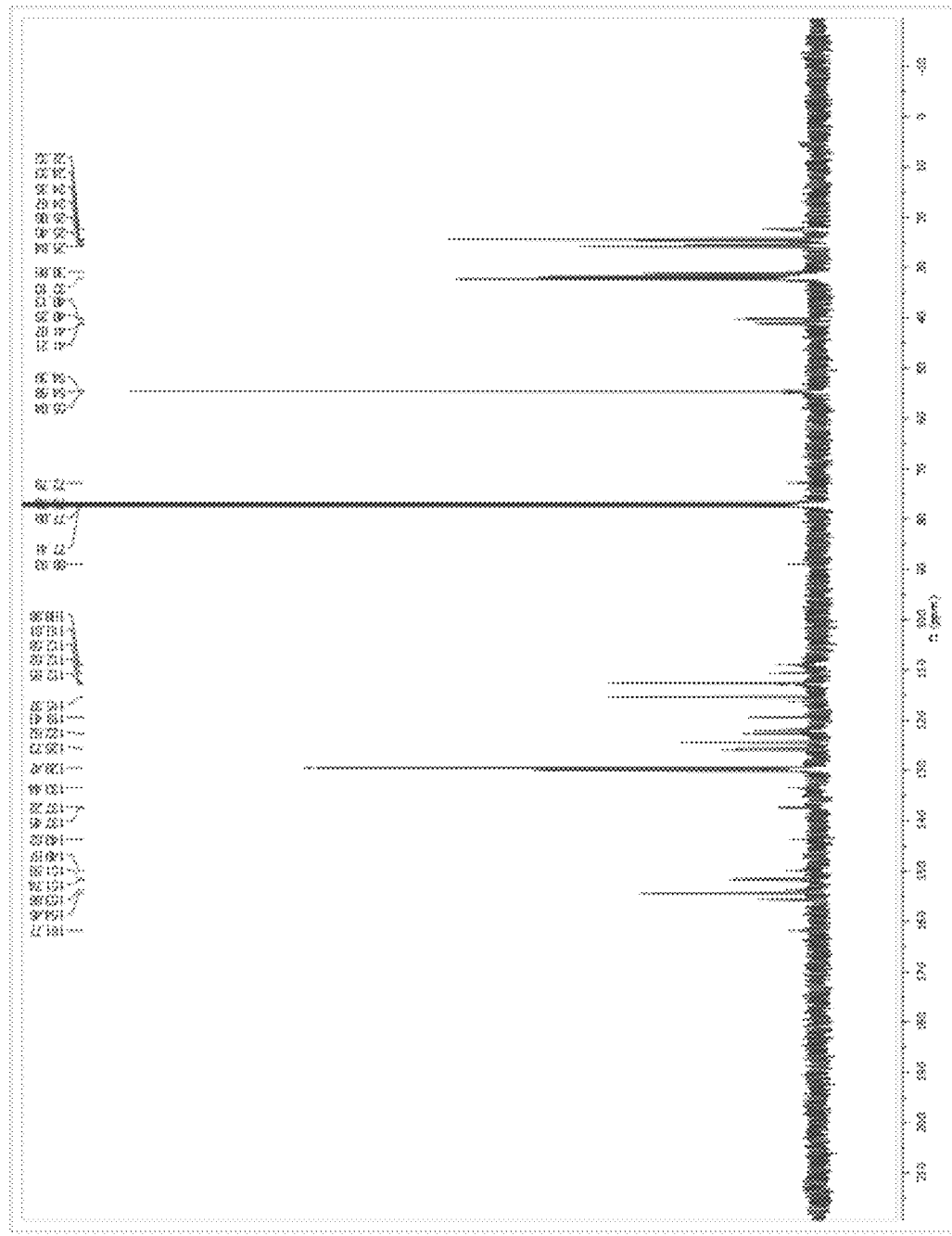
FIG. 10 is a $^{13}$C NMR spectrum of [(π-cinnamyl)Pd(tBuBrettPhos)]OTf.

$^1$H NMR (400 MHz, CDCl$_3$, δ): Complex spectrum—see FIG. 9.
$^{13}$C NMR (100 MHz, CDCl$_3$, δ): Complex spectrum—see FIG. 10.
$^{31}$P NMR (162 MHz, CDCl$_3$, δ): 94.5
$^{19}$F NMR (376 MHz, CDCl$_3$, δ): −77.9 (s, 3F).
Anal. Calcd. for $C_{41}H_{58}F_3O_5PPdS$: C, 57.44; H, 6.82. Found: C, 57.04; H, 6.77.

[(π-allyl)Pd(AdBrettPhos)]OTf

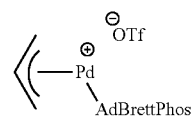

The general procedure is followed using 57.1 mg (0.156 mmol) of [(allyl)PdCl]$_2$, 80.2 mg (0.312 mmol) of AgOTf, 200 mg (0.312 mmol) of AdBrettPhos in anhydrous THF to give 265 mg (0.281 mmol, 90%) of the title compound as a tan solid. The product contained ~2 wt % of THF.

$^1$H NMR (400 MHz, CDCl$_3$, δ): 7.40 (s, 1H), 7.35 (s, 1H), 7.17 (dd, J=2.3 Hz, 8.7 Hz, 1H), 7.04 (app d, J=9.1 Hz, 1H), 5.60 (sept, J=6.8 Hz, 1H), 4.54 (d, J=6.2 Hz, 1H), 3.94 (s, 3H), 3.45-3.35 (m, 4H), 3.04 (quint, J=7.0 Hz, 1H), 2.85 (d, J=12.0 Hz, 1H), 2.63 (quint, J=6.3 Hz, 1H), 2.39-1.91 (m, 18H), 1.81-1.60 (m, 12H), 1.42-1.19 (m, 13H), 0.99-0.82 (m, 4H), 0.78 (d, J=6.7 Hz, 3H). Resonances attributable to THF are observed at 3.76 and 1.83 ppm.

$^{13}$C NMR (100 MHz, CDCl$_3$, δ): 157.1, 154.8, 154.6, 152.6, 151.7, 151.5, 137.1, 136.8, 125.9, 125.3, 124.6, 124.4, 119.3 (2 peaks), 115.4, 112.9, 112.8, 112.0 (2 peaks), 100.2, 99.9, 58.1, 54.7, 45.6, 44.8, 44.7, 42.0, 36.3, 36.2, 34.4, 31.7, 29.2, 26.0, 25.6, 25.5, 24.9, 24.6, 24.3 (2 peaks).

$^{31}$P NMR (162 MHz, CDCl$_3$, δ): 88.9
$^{19}$F NMR (376 MHz, CDCl$_3$, δ): −77.9 (s, 3F).

Example 4 (According to the Invention)

Amination with BrettPhos Complexes

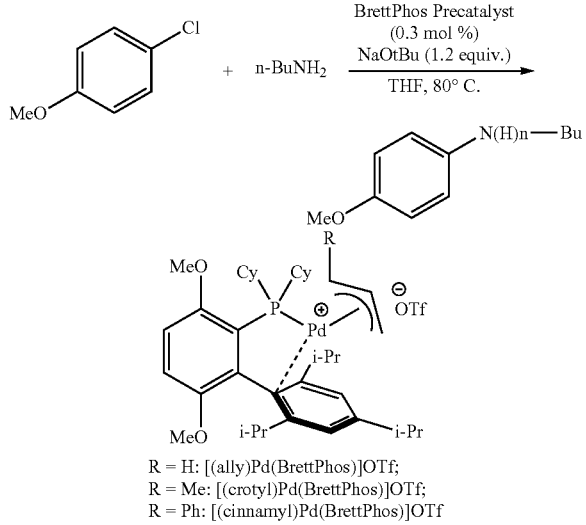

R = H: [(allyl)Pd(BrettPhos)]OTf;
R = Me: [(crotyl)Pd(BrettPhos)]OTf;
R = Ph: [(cinnamyl)Pd(BrettPhos)]OTf A dry Schlenk tube, equipped with a Teflon-coated magnetic stir bar and fitted with a rubber septum, is charged with 5.1 mg (0.003 mmol, 0.3 mol %) of [(allyl)Pd(BrettPhos)]OTf and 231 mg (2.41 mmol, 1.2 equiv) of NaOtBu. The tube is evacuated and backfilled with nitrogen. This evacuation/backfill cycle is repeated two additional times. n-Butylamine (238 μL, 2.41 mmol, 1.2 equiv), n-dodecane (GC standard; 91 μL, 0.40 mmol, 0.2 equiv), and 4-chloroanisole (250 μL, 2.04 mmol, 1.0 equiv) are added followed by 2 mL of anhydrous THF. The tube is placed in a preheated (80° C.) oil bath and stirred vigorously. The tube is then sealed. Aliquots are removed at certain time intervals and analyzed by gas chromatography to monitor conversion.

The experiment was repeated exchanging [(allyl)Pd(BrettPhos)]OTf for [(crotyl)Pd(BrettPhos)]OTf, [(cinnamyl)Pd(BrettPhos)]OTf and a BrettPhos 3$^{rd}$ generation Buchwald palladacycle (illustrated below).

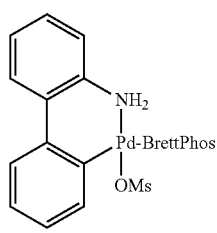

Figure 11:
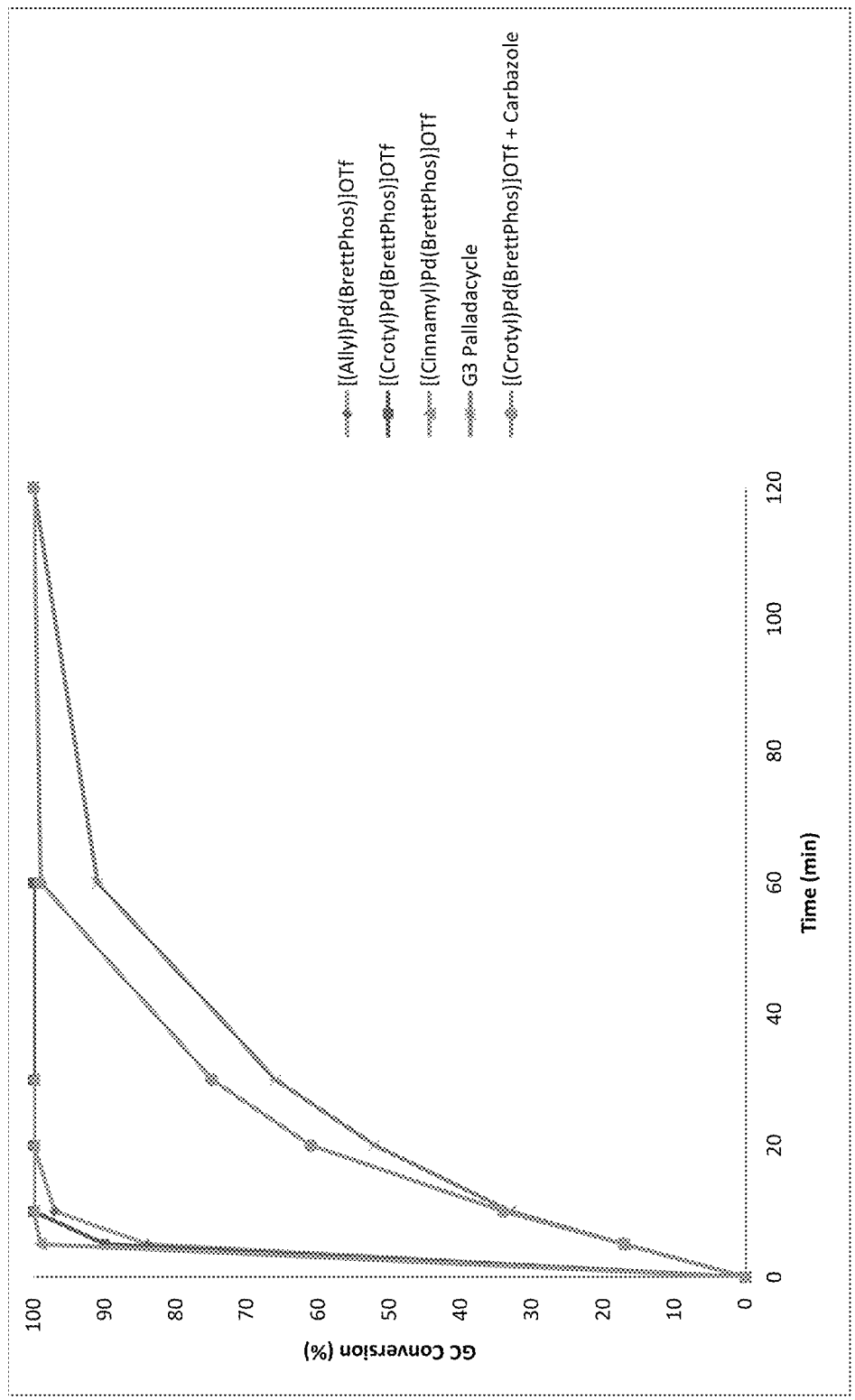
FIG. 11 illustrates the gas chromatography (GC) conversion of the amination of 4-chloroanisole with n-BuNH$_2$ with BrettPhos complexes.

FIG. 11 shows the inhibitory effect of carbazole on the reaction rate. The reaction in which carbazole is released (3$^{rd}$ generation palladacycle) proceeds significantly more slowly (full conversion in 2 hours) than reactions in which carbazole is not generated (i.e. using [(allyl)Pd(BrettPhos)]OTf, [(crotyl)Pd(BrettPhos)]OTf and [(cinnamyl)Pd(BrettPhos)]OTf). The reaction catalysed by [(crotyl)Pd(BrettPhos)]OTf with 0.3 mol % of carbazole added exhibits a significantly reduced reaction rate in which the conversion profile closely matches that of the reaction using the 3$^{rd}$ generation palladacycle. The use of [(cinnamyl)Pd(BrettPhos)]OTf results in full conversion in only 5 minutes.

Example 5 (According to the Invention)

Arylation of Tert-Butylacetate with 4-Chloroanisole

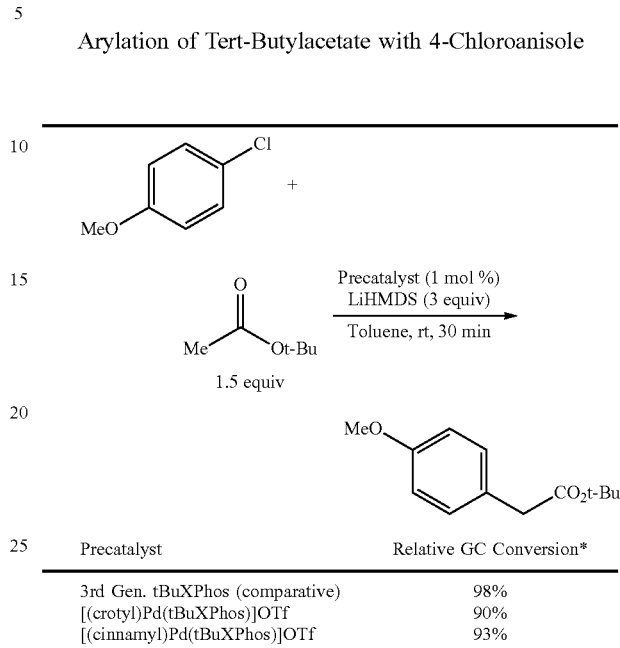

| Precatalyst | Relative GC Conversion* |
|---|---|
| 3rd Gen. tBuXPhos (comparative) | 98% |
| [(crotyl)Pd(tBuXPhos)]OTf | 90% |
| [(cinnamyl)Pd(tBuXPhos)]OTf | 93% |

*Uncorrected GC ratio of Product/SM*100%

A dry Schlenk tube, equipped with a Teflon-coated magnetic stir bar and fitted with a rubber septum, is charged with the precatalyst (0.01 mmol, 1 mol %) and the tube is evacuated and backfilled with nitrogen. This evacuation/backfill cycle is repeated two additional times. 4-Chloroanisole (1.00 mmol, 1.0 equiv) and tert-butylacetate (1.5 mmol, 1.5 equiv) are added followed by LiHMDS solution, 1.0 M in toluene (3.0 mmol, 3.0 equiv). The contents are stirred vigorously at ambient temperature for 30 minutes. The reaction mixture is then quenched by the addition of 5 mL of sat. NH$_4$Cl, and then diluted with 5 mL of EtOAc. An aliquot is removed and analyzed by gas chromatography.

The most active of the [(R-allyl)Pd(tBuXPhos)]OTf precatalysts (R=cinnamyl) compares very well with the 3$^{rd}$ generation palladacycle precatalyst in the arylation of ester enolates (both >90% conversion after 30 min at rt).

Example 6 (According to the Invention)

Arylation of Benzamide with 1-Chloro-2,5-Dimethoxybenzene

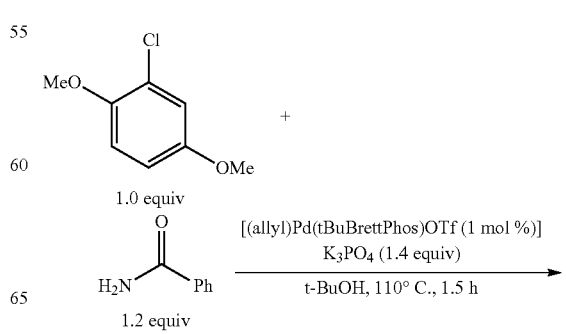

-continued

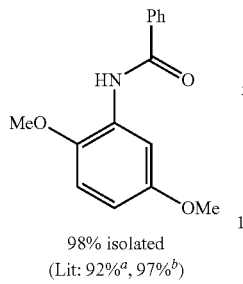

98% isolated
(Lit: 92%[a], 97%[b])

[a]Fors, B. P; Dooleweerdt, K; Zeng, Q.; Buchwald, S. L. Tetrahedron 2009, 65, 6576 [Pd(OAc)$_2$ (1 mol %), tBuBrettPhos (2.2 mol %), H$_2$O (4 mol %)]
[b]Bruno, N. C.; Buchwald, S. L. Org. Lett. 2013, 15, 2876.
[tBuBrettPhos G3 palladacycle]

A dry Schlenk tube is charged with 7.8 mg (0.015 mmol, 1.5 mol %) of [(allyl)Pd(tBuBrettPhos)]OTf, 145 mg (1.20 mmol, 1.20 equiv) of benzamide, and 297 mg (1.40 mmol, 1.40 equiv) of powdered K$_3$PO$_4$. The tube is evacuated and backfilled with nitrogen. This evacuation/backfill cycle is repeated two additional times. 1-Chloro-2,5-dimethoxybenzene (143 μL, 1.00 mmol, 1.00 equiv) is added followed by 2 mL of anhydrous t-BuOH. The tube is placed in a preheated (110° C.) oil bath and the contents are stirred vigorously. The tube is then sealed and aged in the oil bath for 90 min. The tube is then removed from the oil bath and the contents are allowed to cool to ambient temperature. The reaction mixture is diluted with 5 mL EtOAc and 5 mL of H$_2$O. The organic phase is removed and the aqueous is extracted two additional times with 5 mL portions of EtOAc. The organic extracts are combined, dried (MgSO$_4$), filtered, and concentrated in vacuo. The residue is chromatographed on silica gel with 10% EtOAc/hexanes as the eluent to give 252 mg (0.98 mmol, 98%) of the N-benzoyl-2,5-dimethoxyaniline as a light orange viscous oil.

In Pd-catalyzed amidation, the [(allyl)Pd(tBuBrettPhos)]OTf precatalyst gives a higher yield than the originally reported "water preactivation" method of catalyst generation, and compares well with the 3$^{rd}$ generation palladacycle precatalyst, giving a nearly quantitative yield of the aryl amide product. At higher temperatures, the [(allyl)Pd(tBuBrettPhos)]OTf precatalyst quickly and efficiently forms the active catalyst. Additionally, the reaction can be run with a significantly reduced catalyst loading of 0.1 mol % of [(allyl)Pd(tBuBrettPhos)]OTf, and 100% conversion/98% isolated yield is still obtained with a 16 hour reaction time.

Example 7 (According to the Invention)

Arylation of Primary Amines Catalysed by [(π-Crotyl)Pd(BrettPhos)]OTf[a]

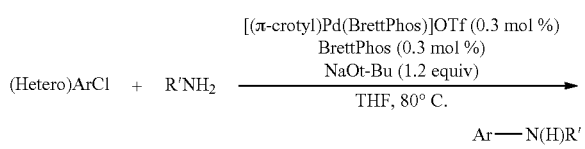

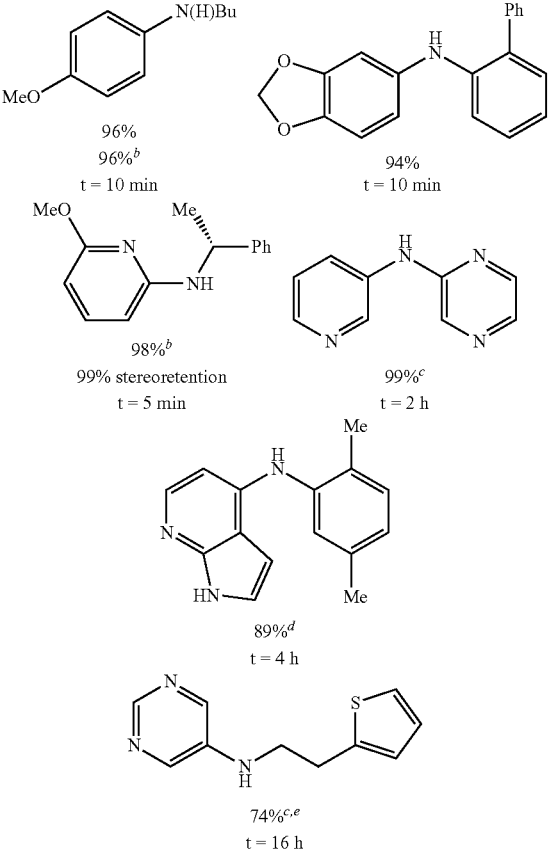

[a] General conditions: aryl/heteroarylchloride (1.00 mmol), amine (1.20 mmol), NaOt-Bu (1.2 mmol), [(π-crotyl)Pd(BrettPhos)]OTf (0.3 mol %), BrettPhos (0.3 mol %), THF (2 mL), 80° C. [b] [(π-cinnamyl)Pd(BrettPhos)]OTf (0.3 mol %) are used. [c] base is K$_2$CO$_3$ (1.4 mmol), solvent is 2-methyl-2-butanol (2 mL), 110° C. [d] base is LiHMDS (2.4 mmol), [(π-crotyl)Pd(BrettPhos)]OTf (1.0 mol %), BrettPhos (0 mol %), 65° C. [e] [(π-crotyl)Pd(BrettPhos)]OTf (1.2 mol %), BrettPhos (1.2 mol %).

N-butyl-4-methoxyaniline, N-([1,1'-biphenyl]-2-yl)benzo[d][1,3]dioxol-5-amine and (R)-6-methoxy-N-(1-phenylethyl)pyridin-2-amine are formed with fast reaction times (5-10 min) using primary aliphatic (for N-butyl-4-methoxyaniline), aromatic (for N-([1,1'-biphenyl]-2-yl)benzo[d][1,3]dioxol-5-amine), and optically active α-chiral (for (R)-6-methoxy-N-(1-phenylethyl)pyridin-2-amine) amines at 0.3 mol % catalyst loading. Notably, (R)-6-methoxy-N-(1-phenylethyl)pyridin-2-amine is formed with high stereochemical fidelity (99% stereoretention), as erosion of enantiopurity of a-chiral amines in Buchwald-Hartwig amination reactions can be problematic. Heterocyclic substrates which contain more than one nitrogen atom can also be efficiently coupled in good-high yields using [(π-crotyl)Pd(BrettPhos)]OTf (i.e. N-(pyridin-3-yl)pyrazin-2-amine, N-(2,5-dimethylphenyl)-1H-pyrrolo[2,3-b]pyridin-4-amine and N-(2-(thiophen-2-yl)ethyl)pyrimidin-5-amine) using slightly modified conditions. The similar yields of N-butyl-4-methoxyaniline are observed using [(π-crotyl)Pd(BrettPhos)]OTf and [(π-cinnamyl)Pd(BrettPhos)]OTf (96%) demonstrate the interchangeability of these complexes.

General Procedure for the Primary Amination Reactions

An oven dried Schlenk tube equipped with a Teflon-coated magnetic stir bar is charged with [(π-crotyl)Pd(BrettPhos)]OTf (0.3-1.2 mol % as indicated), BrettPhos (0.3-1.2 mol % as indicated), aryl chloride (1.00 mmol, if solid), and NaOt-Bu (1.20 mmol). The tube is evacuated and backfilled with nitrogen. This evacuation/backfill cycle is repeated two additional times. Dodecane (GC standard, 0.20 mmol), the amine (1.20 mmol), aryl chloride (1.00 mmol, if liquid), and anhydrous THF (2 mL) are added sequentially via syringe. The tube is placed in a preheated oil bath and stirred for the indicated time. The tube is then removed from the oil bath and allowed to cool to room temperature. The reaction mixture is diluted with 10 mL of EtOAc and filtered through a pad of Celite. The solution is concentrated in vacuo and the residue is chromatographed on silica gel using a Teledyne ISCO CombiFlashRf.

N-butyl-4-methoxyaniline

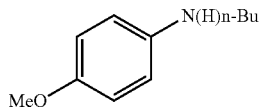

According to the general procedure, a mixture of 4-chloroanisole (123 µL, 1.00 mmol), n-butylamine (119 µL, 1.20 mmol), NaOtBu (115 mg, 1.20 mmol), [(π-crotyl)Pd(BrettPhos)]OTf (2.5 mg, 0.003 mmol), BrettPhos (1.6 mg, 0.003 mmol), and 2 mL THF are stirred at 80° C. for 10 minutes. The crude material is chromatographed on silica gel with a gradient of 0-5% EtOAc/hexanes as the eluent to give 171 mg (0.96 mmol, 96%) of N-butyl-4-methoxyaniline as a colorless oil. The spectral properties match those previously reported (Shankaraiaha, N.; Markandeya, N.; Srinivasulu, V.; Sreekanth, K.; Reddy, C. S.; Santos, L. S.; Kamal, A. *J. Org. Chem.* 2011, 76, 7017).

N-([1,1'-biphenyl]-2-yl)benzo[d][1,3]dioxol-5-amine

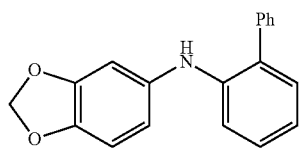 [SMILES: c1ccc(-c2ccccc2Nc2ccc3c(c2)OCO3)cc1]

According to the general procedure, a mixture of 5-chloro-1,3-benzodioxole (117 µL, 1.00 mmol), 2-aminobiphenyl (203 mg, 1.20 mmol), NaOtBu (115 mg, 1.20 mmol), [(π-crotyl)Pd(BrettPhos)]OTf (2.5 mg, 0.003 mmol), BrettPhos (1.6 mg, 0.003 mmol), and 2 mL THF are stirred at 80° C. for 10 minutes. The crude material is chromatographed on silica gel with a gradient of 0-5% EtOAc/hexanes as the eluent to give 272 mg (0.94 mmol, 94%) of N-([1,1'-biphenyl]-2-yl)benzo[d][1,3]dioxol-5-amine as a colorless oil.

$^1$H NMR (400 MHz, CDCl$_3$, δ): 7.53-7.43 (m, 4H), 7.42-7.34 (m, 1H), 7.28-7.15 (m, 3H), 7.01-6.90 (m, 1H), 6.74 (d, J=8.6 Hz, 1H), 6.69 (d, J=2.3 Hz, 1H), 6.53 (dd, J=2.3 Hz, 8.3 Hz, 1H), 5.93 (s, 2H), 5.51 (s, 1H).

$^{13}$C NMR (100 MHz, CDCl$_3$, δ): 148.3, 143.1, 141.9, 139.2, 137.7, 130.9, 130.3, 129.5, 129.1, 128.5, 127.6, 120.1, 115.8, 113.6, 108.7, 103.2, 101.2.

Anal. Calcd. for C$_{19}$H$_{15}$NO$_2$: C, 78.87; H, 5.23; N, 4.84. Found: C, 78.91; H, 5.29; N, 4.79.

(R)-6-methoxy-N-(1-phenylethyl)pyridin-2-amine

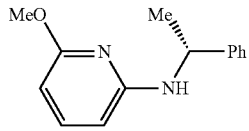 [SMILES: COc1cccc(N[C@H](C)c2ccccc2)n1]

According to the general procedure, a mixture of 2-chloro-6-methoxypyridine (119 µL, 1.00 mmol), (R)-(+)-α-methylbenzylamine (98% ee, 153 µL, 1.20 mmol), NaOtBu (115 mg, 1.20 mmol), [(π-cinnamyl)Pd(BrettPhos)]OTf (2.7 mg, 0.003 mmol), BrettPhos (1.6 mg, 0.003 mmol), and 1 mL THF are stirred at 80° C. for 5 minutes. The crude material is chromatographed on silica gel with a gradient of 0-5% EtOAc/hexanes as the eluent to give 223 mg (0.98 mmol, 98%) of (R)-6-methoxy-N-(1-phenylethyl)pyridin-2-amine as a colorless oil. [α]$_D^{25}$=−38.2° (c. 1.03 CHCl$_3$). The enantiomeric excess is measured to be 97% by chiral HPLC analysis (Chiracel OD-H column, 5% IPA/Hexanes, 1 mL/min, 254 nm). Racemic material is prepared in an identical experiment using racemic α-methylbenzylamine.

$^1$H NMR (400 MHz, CDCl$_3$, δ): 7.41-7.29 (m, 4H), 7.28-7.19 (m, 2H), 6.00 (d, J=8.0 Hz, 1H), 5.77 (d, J=8.1 Hz, 1H), 4.89-4.63 (m, 2H), 3.81 (s, 3H), 1.54 (d, J=7.2 Hz, 3H).

$^{13}$C NMR (100 MHz, CDCl$_3$, δ): 163.6, 157.0, 145.2, 140.1, 128.7, 127.0, 126.0, 98.2, 97.9, 53.2, 52.1, 24.4.

Anal. Calcd. for C$_{14}$H$_{16}$N$_2$O: C, 73.66; H, 7.06. Found: C, 73.96; H, 6.97.

N-(pyridin-3-yl)pyrazin-2-amine

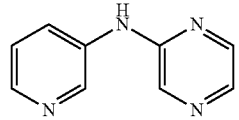 [SMILES: c1cncc(Nc2cnccn2)c1]

The general procedure is followed with the following modifications: A mixture of 3-chloropyridine (95 µL, 1.00 mmol), 2-aminopyrazine (114 mg, 1.20 mmol), K$_2$CO$_3$ (194 mg, 1.40 mmol), [(π-crotyl)Pd(BrettPhos)]OTf (2.5 mg, 0.003 mmol), BrettPhos (1.6 mg, 0.003 mmol), and 2 mL t-AmOH are stirred at 110° C. for 2 hours. The crude material is chromatographed on silica gel with a gradient of 0-5% MeOH/CH$_2$Cl$_2$ as the eluent to give 170 mg (0.99 mmol, 99%) of N-(pyridin-3-yl)pyrazin-2-amine as a white solid. The spectral properties match those previously reported (Fors, B. P.; Davis, N. R.; Buchwald, S. L. *J. Am. Chem. Soc.* 2009, 131, 5766).

N-(2,5-dimethylphenyl)-1H-pyrrolo[2,3-b]pyridin-4-amine

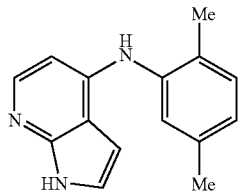 [SMILES: Cc1ccc(C)c(Nc2ccnc3[nH]ccc23)c1]

An oven dried Schlenk tube equipped with a Teflon-coated magnetic stir bar is charged with [(π-crotyl)Pd(BrettPhos)]OTf (8.5 mg, 1.2 mol), and 4-chloro-7-azaindole (153 mg, 1.00 mmol). The tube is evacuated and backfilled with nitrogen. This evacuation/backfill cycle is repeated two additional times. 2,5-Dimethylaniline (150 µL, 1.20 mmol) and 2.4 mL of LiHMDS solution in THF (2.4 mmol) are added sequentially via syringe. The tube is placed in a preheated oil bath (65° C.) and stirred for 4 hours. The tube is then removed from the oil bath and allowed to cool to room temperature, and 2 mL of 1M HCl (aq) is added followed by 15 mL EtOAc. The contents of the tube are then poured into a separatory funnel containing 20 mL of sat. NaHCO$_3$. The aqueous is extracted with EtOAc (3×15 mL), and the combined extracts are washed with brine, dried over anhydrous MgSO$_4$, concentrated in vacuo, and the residue is chromatographed on silica gel using a Teledyne ISCO CombiFlashRf using a gradient of 0-10% MeOH/CH$_2$Cl$_2$ as the eluent to give 223 mg (0.94 mmol, 94%) of N-(2,5-dimethylphenyl)-1H-pyrrolo[2,3-b]pyridin-4-amine as a light brown solid.

$^1$H NMR (400 MHz, CDCl$_3$, δ): 12.2 (br, s, 1H), 8.10 (d, J=5.1 Hz, 1H), 7.37-7.11 (m, 3H), 6.99 (d, J=7.4 Hz, 1H), 6.42 (d, J=5.7 Hz, 1H), 6.38 (d, J=2.5 Hz, 1H), 6.08 (s, 1H), 2.36 (s, 3H), 2.27 (s, 3H).

$^{13}$C NMR (100 MHz, CDCl$_3$, δ): 150.2, 145.7, 143.9, 138.3, 136.7, 131.0, 129.6, 126.1, 125.3, 122.4, 108.8, 99.3, 96.9, 21.1, 17.6.

HRMS (ESI) m/z [M+H]$^+$ Calcd. for C$_{15}$H$_{16}$N$_3$: 238.1344. Found: 238.1341.

N-(2-(thiophen-2-yl)ethyl)pyrimidin-5-amine

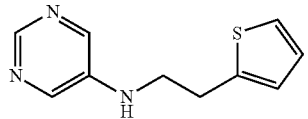 [SMILES: c1csc(CCNc2cncnc2)c1]

The general procedure was followed with the following modifications: A mixture of 5-bromopyrimidine (159 mg, 1.00 mmol), 2-thiophenemethylamine (140 µL, 1.20 mmol), K$_2$CO$_3$ (194 mg, 1.40 mmol), [(π-crotyl)Pd(BrettPhos)]OTf (10.2 mg, 0.012 mmol), BrettPhos (6.4 mg, 0.012 mmol), and 2 mL t-AmOH are stirred at 110° C. for 19 hours. The crude material is chromatographed on silica gel with a gradient of 25-75% EtOAc/hexanes as the eluent to give 152 mg (0.74 mmol, 74%) of N-(2-(thiophen-2-yl)ethyl)pyrimidin-5-amine as an off-white solid.

$^1$H NMR (400 MHz, CDCl$_3$, δ): 8.60 (s, 1H), 8.10 (s, 2H), 7.19 (dd, J=1.2 Hz, 3.2 Hz, 1H), 6.97 (dd, J=7.4 Hz, 5.3 Hz, 1H), 6.89-6.83 (m, 1H), 3.89 (br s, 1H), 3.47 (q, J=6.5 Hz, 2H), 3.16 (app t, J=6.5 Hz, 2H).

$^{13}$C NMR (100 MHz, CDCl$_3$, δ): 148.9, 141.5, 141.2, 140.7, 127.3, 125.8, 124.5, 44.4, 29.5.

Anal. Calcd. for C$_{10}$H$_{11}$N$_3$S: C, 58.51; H, 5.40; N, 20.47. Found: C, 58.28; H, 5.43; N, 20.42.

Example 8 (According to the Invention)

C-N cross coupling reactions using [(π-allyl)Pd(tBuBrettPhos)]OTf$^a$

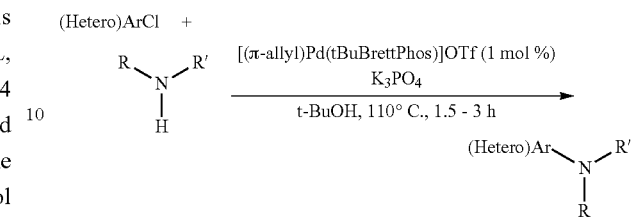

Primary Amides: 1 mol % of [(π-allyl)Pd(tBuBrettPhos)]OTf

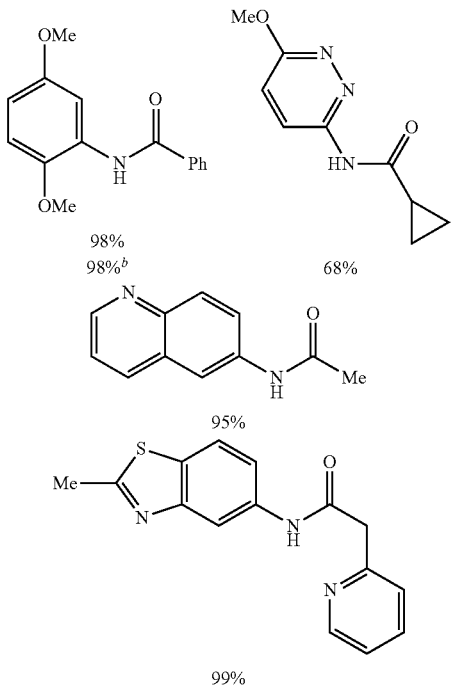

Cyclic Amides/Oxazolidinone: 1.5 mol % of [(π-allyl)Pd(tBuXPhos)]OTf

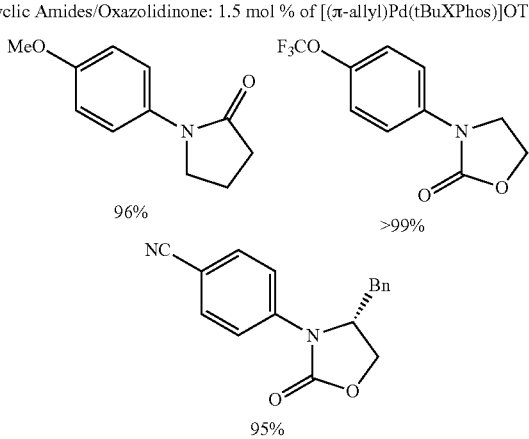

-continued

2-Aminothiazole: 1.5 mol % of [(π-allyl)Pd(tBuXPhos)]OTf

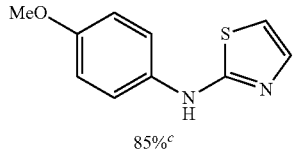

85%[c]

[a] General conditions - primary amides: (hetero)arylchloride (1.00 mmol), amide (1.20 mmol), [(p-allyl)Pd(tBuBrettPhos)]OTf (1.0 mol %), K₃PO₄ (1.4 mmol), t-BuOH (2 mL), 110° C.; cyclic amides: (hetero)arylchloride (1.00 mmol), amide (1.20 mmol), [(p-allyl)Pd(tBuBrettPhos)]OTf (1.5 mol %), K₃PO₄ (1.4 mmol), t-BuOH (2 mL), 110° C.; 2-aminothiazole: 4-bromoanisole (1.00 mmol), 2-aminothiazole (1.20 mmol), [(p-allyl)Pd(tBuXPhos)]OTf (1.5 mol %), K₂CO₃ (1.4 mmol), t-BuOH (2 mL), 110° C.; [b] 0.1 mol% of [(p-allyl)Pd(tBuBrettPhos)]OTf used, 16 h reaction time.

The tBuBrettPhos-based catalyst [(π-allyl)Pd(tBuBrettPhos)]OTf shows excellent reactivity in challenging C—N cross-coupling reactions. The results are summarized in the table above. The arylation of primary amides are highly efficient giving aryl amide products generally with high yields using 1.0 mol % of [(π-allyl)Pd(tBuBrettPhos)]OTf. The exception is the synthesis of N-(6-methoxypyridazin-3-yl)cyclopropanecarboxamide, which still gives the product in 68% yield. Notably, in the reaction to form N-(2,5-dimethoxyphenyl)benzamide, the catalyst loading could be lowered to 0.1 mol % with a longer reaction time without a deleterious effect on yield. Additionally, cyclic secondary amides as well as a cyclic oxazolidinone prove to be excellent substrates if the catalyst loading is increased to 1.5 mol %, as 1-(4-methoxyphenyl)pyrrolidin-2-one, 3-(4-(trifluoromethoxy)phenyl)oxazolidin-2-one and (S)-4-(4-benzyl-2-oxooxazolidin-3-yl)benzonitrile are all formed in ≥95% yields. With [(π-allyl)Pd(tBuBrettPhos)]OTf, 2-aminothiazole is efficiently coupled with 4-bromoanisole to produce N-(4-methoxyphenyl)thiazol-2-amine in 85% yield in the absence of acetate.

General Procedure for the Arylation Reactions of Primary Amides

An oven dried Schlenk tube equipped with a Teflon-coated magnetic stir bar is charged with [(π-allyl)Pd(tBuBrettPhos)]OTf (7.8 mg, 0.01 mmol, 1 mol %), aryl chloride (1.00 mmol, if solid), amide (1.20 mmol), and K₃PO₄ (297 mg, 1.40 mmol). The tube is capped with a rubber septum and is evacuated and backfilled with nitrogen. This evacuation/backfill cycle is repeated two additional times. The aryl chloride (1.00 mmol, if liquid), and anhydrous tBuOH (2 mL) are added sequentially via syringe. The tube is placed in a preheated oil bath (110° C.), sealed, and stirred for 1.5 hours unless otherwise indicated. The tube is then removed from the oil bath and allowed to cool to room temperature. H₂O (5 mL) was added, and the aqueous phase is extracted with EtOAc (3×5 mL). The organic extracts are combined, dried over anhydrous MgSO₄, filtered, and concentrated in vacuo. The residue is chromatographed on silica gel using a Teledyne ISCO CombiFlashRf.

N-(2,5-dimethoxyphenyl)benzamide

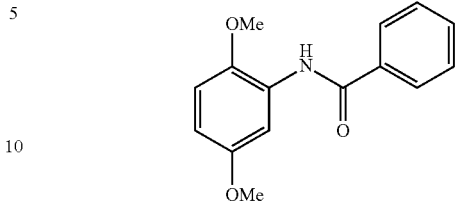

According to the general procedure, a mixture of 2-chloro-1,4-dimethoxybenzene (143 mL, 1.00 mmol), benzamide (145 mg, 1.20 mmol), K₃PO₄ (297 mg, 1.40 mmol), [(π-allyl)Pd(tBuBrettPhos)]OTf (7.8 mg, 0.01 mmol), and 2 mL of anhydrous tBuOH are stirred at 110° C. for 1.5 hours. The crude material is chromatographed on silica gel with 10% EtOAc/hexanes as the eluent to give 252 mg (0.98 mmol, 96%) of N-(2,5-dimethoxyphenyl)benzamide as a near-colorless oil. The spectroscopic properties match those previously reported (Fors, B. P. Dooleweerdt, K.; Zeng, Q.; Buchwald, S. L. *Tetrahedron* 2009, 65, 6576).

A similar experiment using 0.8 mg of [(p-allyl)Pd(tBuBrettPhos)]OTf (0.001 mmol, 0.1 mol %) and a 16 hour stir time gives 251 mg (0.98 mmol, 98%) of N-(2,5-dimethoxyphenyl)benzamide as a colorless oil.

N-(6-methoxypyridazin-3-yl)cyclopropanecarboxamide

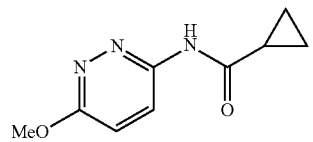

According to the general procedure, a mixture of 3-chloro-6-methoxypyridazine (145 mg, 1.00 mmol), cyclopropanecarboxamide (102 mg, 1.20 mmol), K₃PO₄ (297 mg, 1.40 mmol), [(π-allyl)Pd(tBuBrettPhos)]OTf (7.8 mg, 0.01 mmol), and 2 mL of anhydrous tBuOH are stirred at 110° C. for 2 hours. The crude material is chromatographed on silica gel with a gradient of 0-2.5% MeOH/CH₂Cl₂ as the eluent to give 132 mg (0.68 mmol, 68%) of N-(6-methoxypyridazin-3-yl)cyclopropanecarboxamide as a white solid.

$^1$H NMR (400 MHz, CDCl₃, δ): 11.2 (br s, 1H), 8.54 (d, J=8.5 Hz, 1H), 7.02 (d, J=8.5 Hz, 1H), 3.98 (s, 3H), 2.57-2.46 (m, 1H), 1.14-1.06 (m, 2H), 0.93-0.84 (m, 2H).

$^{13}$C NMR (100 MHz, CDCl₃, δ): 174.0, 162.4, 152.9, 123.8, 119.8, 54.4, 15.5, 8.79.

Anal. Calcd. for C₉H₁₁N₃O₂: C, 55.95; H, 5.74; N, 21.75. Found: C, 56.18; H, 5.76; N, 21.70.

N-(quinolin-6-yl)acetamide

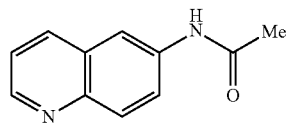 [SMILES: CC(=O)Nc1ccc2ncccc2c1]

According to the general procedure, a mixture of 6-chloroquinoline (164 mg, 1.00 mmol), acetamide (71 mg, 1.20 mmol), K$_3$PO$_4$ (297 mg, 1.40 mmol), [(π-allyl)Pd(tBuBrettPhos)]OTf (7.8 mg, 0.01 mmol), and 2 mL of anhydrous tBuOH are stirred at 110° C. for 1.5 hours. The crude material is chromatographed on silica gel with a gradient of 0-4% MeOH/CH$_2$Cl$_2$ as the eluent to give 132 mg (0.95 mmol, 95%) of N-(quinolin-6-yl)acetamide as a pale yellow solid.

$^1$H NMR (400 MHz, CDCl$_3$, δ): 8.86-8.64 (m, 2H), 8.38 (s, 1H), 8.06 (d, J=7.7 Hz, 1H), 7.97 (d, J=9.5 Hz, 1H), 7.59 (dd, J=2.5 Hz, 9.1 Hz, 1H), 7.34 (dd, J=3.9 Hz, 8.6 Hz, 1H), 0.88 (s, 3H).

$^{13}$C NMR (100 MHz, CDCl$_3$, δ): 169.3, 149.2, 145.4, 136.4, 136.2, 129.8, 129.0, 123.5, 121.7, 116.3, 24.7.

Anal. Calcd. for C$_{11}$H$_{10}$N$_2$O: C, 70.95; H, 5.41; N, 15.04. Found: C, 70.66; H, 5.51; N, 14.94.

N-(2-methylbenzo[d]thiazol-5-yl)-2-(pyridin-2-yl)acetamide

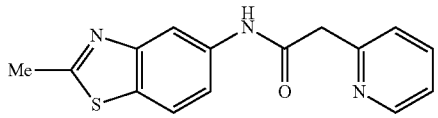 [SMILES: Cc1nc2cc(NC(=O)Cc3ccccn3)ccc2s1]

According to the general procedure, a mixture of 5-chloro-2-methylbenzothiazole (184 mg, 1.00 mmol), 2-(pyridine-2-yl)acetamide (143 mg, 1.20 mmol), K$_3$PO$_4$ (297 mg, 1.40 mmol), [(π-allyl)Pd(tBuBrettPhos)]OTf (7.8 mg, 0.01 mmol), and 2 mL of anhydrous tBuOH are stirred at 110° C. for 1.5 hours. The crude material is chromatographed on silica gel with a gradient of 0-2% MeOH/CH$_2$Cl$_2$ as the eluent to give 279 mg (0.99 mmol, 99%) of N-(2-methylbenzo[d]thiazol-5-yl)-2-(pyridin-2-yl)acetamide as a pale yellow-green solid.

$^1$H NMR (400 MHz, DMSO-d$_6$, δ): 10.4 (br s, 1H), 8.51 (d, J=4.6 Hz, 1H), 8.32 (d, J=1.8 Hz, 1H), 7.91 (d, J=8.5 Hz, 1H), 7.76 (td, J=1.5 Hz, 7.4 Hz, 1H), 7.57 (dd, J=1.5 Hz, 8.5 Hz, 1H), 7.42 (d, J=7.5 Hz, 1H), 7.27 (dd, J=4.9 Hz, 7.4 Hz, 1H), 3.90 (s, 2H), 2.76 (s, 3H).

$^{13}$C NMR (100 MHz, DMSO-d$_6$, δ): 168.3, 167.9, 156.0, 153.5, 149.0, 137.6, 136.5, 129.5, 124.0, 121.9, 121.8, 117.0, 111.9, 45.9, 19.8.

HRMS (ESI) m/z [M+H]$^+$ Calcd. for C$_{15}$H$_{14}$N$_3$OS: 284.0858. Found: 284.0861.

N-(benzo[d][1,3]dioxol-5-yl)nicotinamide

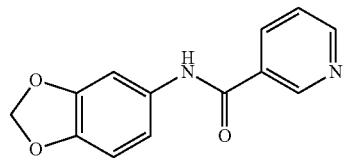 [SMILES: O=C(Nc1ccc2c(c1)OCO2)c1cccnc1]

According to the general procedure, a mixture of 6-chloroquinoline (164 mg, 1.00 mmol), acetamide (71 mg, 1.20 mmol), K$_3$PO$_4$ (297 mg, 1.40 mmol), [(π-allyl)Pd(tBuBrettPhos)]OTf (7.8 mg, 0.01 mmol), and 2 mL of anhydrous tBuOH are stirred at 110° C. for 1.5 hours. The crude material is chromatographed on silica gel with a gradient of 0-4% MeOH/CH$_2$Cl$_2$ as the eluent to give 132 mg (0.95 mmol, 95%) of N-(benzo[d][1,3]dioxol-5-yl)nicotinamide as a pale yellow solid.

$^1$H NMR (400 MHz, DMSO-d$_6$, δ): 10.3 (br s, 1H), 9.08 (d, J=1.7 Hz, 1H), 8.75 (dd, J=1.6 Hz, 4.9 Hz, 1H), 8.26 (td, J=1.9 Hz, 8.1 Hz, 1H), 7.44 (dd, J=4.7 Hz, 7.9 Hz, 1H), 7.43 (d, J=2.0 Hz, 1H), 7.18 (dd, J=2.0 Hz, 8.4 Hz, 1H), 6.91 (d, J=8.4 Hz, 1H), 6.02 (s, 2H).

$^{13}$C NMR (100 MHz, DMSO-d$_6$, δ): 163.7, 152.0, 148.6, 147.0, 143.5, 135.3, 133.1, 130.6, 123.5, 113.4, 108.0, 102.5, 101.1.

Anal. Calcd. for C$_{13}$H$_{10}$N$_2$O$_3$: C, 64.46; H, 4.16; N, 11.56. Found: C, 64.60; H, 4.37; N, 11.16.

General Procedure for the Arylation Reactions of Cyclic Amide/Oxazolidinones

An oven dried Schlenk tube equipped with a Teflon-coated magnetic stir bar is charged with [(π-allyl)Pd(tBuBrettPhos)]OTf (11.7 mg, 0.015 mmol, 1.5 mol %), aryl chloride (1.00 mmol, if solid), amide/oxazolidinone (1.20 mmol, if solid), and K$_3$PO$_4$ (297 mg, 1.40 mmol). The tube is capped with a rubber septum and is evacuated and backfilled with nitrogen. This evacuation/backfill cycle is repeated two additional times. The amide (1.20 mmol, if liquid) aryl chloride (1.00 mmol, if liquid), and anhydrous tBuOH (2 mL) are added sequentially via syringe. The tube is placed in a preheated oil bath (110° C.), sealed, and stirred for 3 hours. The tube is then removed from the oil bath and allowed to cool to room temperature. H$_2$O (5 mL) was added, and the aqueous phase is extracted with EtOAc (3×5 mL). The organic extracts are combined, dried over anhydrous MgSO$_4$, filtered, and concentrated in vacuo. The residue is chromatographed on silica gel using a Teledyne ISCO CombiFlashRf.

1-(4-methoxyphenyl)pyrrolidin-2-one

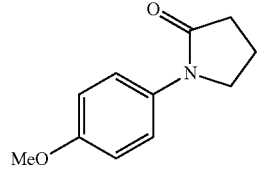 [SMILES: COc1ccc(N2CCCC2=O)cc1]

According to the general procedure, a mixture of 4-chloroanisole (123 mL, 1.00 mmol), 2-pyrrolidinone (91 mL, 1.20 mmol), K$_3$PO$_4$ (297 mg, 1.40 mmol), [(π-allyl)Pd(tBuBrettPhos)]OTf (11.7 mg, 0.015 mmol), and 2 mL of anhydrous tBuOH are stirred at 110° C. for 3 hours. The crude material is chromatographed on silica gel with a gradient of 40-100% EtOAc/hexanes as the eluent to give 183 mg (0.96 mmol, 96%) of 1-(4-methoxyphenyl)pyrrolidin-2-one as a white solid. The spectroscopic properties match those previously reported (Easton, C. J.; Pitt, M. J.; Ward, C. M. *Tetrahedron* 1995, 51, 12781).

3-(4-(trifluoromethoxy)phenyl)oxazolidin-2-one

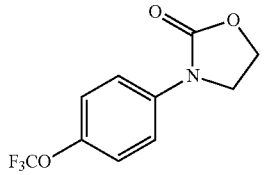 [SMILES: O=C1OCCN1c1ccc(OC(F)(F)F)cc1]

According to the general procedure, a mixture of 1-chloro-4-trifluoromethoxybenzene (144 mL, 1.00 mmol), 2-oxazolidinone (105 mg, 1.20 mmol), K$_3$PO$_4$ (297 mg, 1.40 mmol), [(π-allyl)Pd(tBuBrettPhos)]OTf (11.7 mg, 0.015 mmol), and 2 mL of anhydrous tBuOH are stirred at 110° C. for 3 hours. The crude material is chromatographed on silica gel with a gradient of 0-40% EtOAc/hexanes as the eluent to give 247 mg (1.00 mmol, 100%) of 3-(4-(trifluoromethoxy)phenyl)oxazolidin-2-one as a white solid.

$^1$H NMR (400 MHz, CDCl$_3$, δ): 7.55 (app d, J=9.5 Hz, 2H), 7.20 (app d, J=8.8 Hz, 2H), 4.51-4.40 (m, 2H), 4.07-3.98 (m, 2H).

$^{13}$C NMR (100 MHz, CDCl$_3$, δ): 155.3, 145.2, 137.1, 121.8, 120.6 (q, J$_{C-F}$=256 Hz), 119.4, 61.4, 45.2.

HRMS (ESI) m/z [M+H]$^+$ Calcd. for C$_{10}$H$_9$F$_3$NO$_3$: 248.0535. Found: 248.0537.

(S)-4-(4-benzyl-2-oxooxazolidin-3-yl)benzonitrile

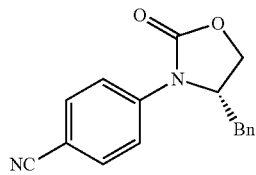 [SMILES: N#Cc1ccc(N2C(=O)OC[C@@H]2Cc2ccccc2)cc1]

According to the general procedure, a mixture of 4-chlorobenzonitrile (138 mg, 1.00 mmol), (S)-(−)-4-benzyl-2-oxazolidinone (186 mg, 1.20 mmol), K$_3$PO$_4$ (297 mg, 1.40 mmol), [(π-allyl)Pd(tBuBrettPhos)]OTf (11.7 mg, 0.015 mmol), and 2 mL of anhydrous tBuOH are stirred at 110° C. for 3 hours. The crude material is chromatographed on silica gel with a gradient of 0-40% EtOAc/hexanes as the eluent to give 265 mg (0.95 mmol, 95%) of (S)-4-(4-benzyl-2-oxooxazolidin-3-yl)benzonitrile as a brown solid. The spectroscopic properties match those previously reported (Ghosh, A.; Sieser, J. E.; Riou, M.; Cai, W.; Rivera-Ruiz, L. *Org. Lett.* 2003, 5, 2207).

N-(4-methoxyphenyl)thiazol-2-amine

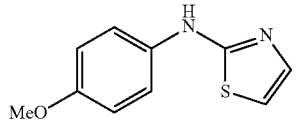 [SMILES: COc1ccc(Nc2nccs2)cc1]

An oven dried Schlenk tube equipped with a Teflon-coated magnetic stir bar is charged with [(π-allyl)Pd(tBuBrettPhos)]OTf (11.7 mg, 0.015 mmol, 1.5 mol %), 2-aminothiazole (100 mg, 1.00 mmol), and K$_2$CO$_3$ (194 mg, 1.40 mmol). The tube is capped with a rubber septum and is evacuated and backfilled with nitrogen. This evacuation/backfill cycle is repeated two additional times. 4-Bromoanisole (125 mL, 1.00 mmol) and anhydrous tBuOH (4 mL) are added sequentially via syringe. The tube is placed in a preheated oil bath (110° C.), sealed, and stirred for 3 hours. The tube is then removed from the oil bath and diluted with 10 mL of EtOAc and H$_2$O (5 mL). The aqueous phase is extracted (3×5 mL of EtOAc). The combined extracts are washed with brine (5 mL), dried over anhydrous MgSO$_4$, filtered, and concentrated in vacuo. The residue is chromatographed on silica gel using a Teledyne ISCO CombiFlashRf with a gradient of 0-3% MeOH/CH$_2$Cl$_2$ as the eluent to give 176 mg (0.85 mmol, 85%) of N-(4-methoxyphenyl)thiazol-2-amine as a tan solid. The spectroscopic properties match those previously reported (McGowan, M. A.; Henderson, J. L.; Buchwald, S. L. *Org. Lett.* 2012, 14, 1432).

Example 9 (According to the Invention)

Coupling Reactions Using Allylpalladium Precatalysts

Several cationic complexes of the present invention are evaluated to assess their efficiency in a wider scope of cross-coupling reactions. These include cross-coupling reactions involving sulphonamides, alcohols and indoles.

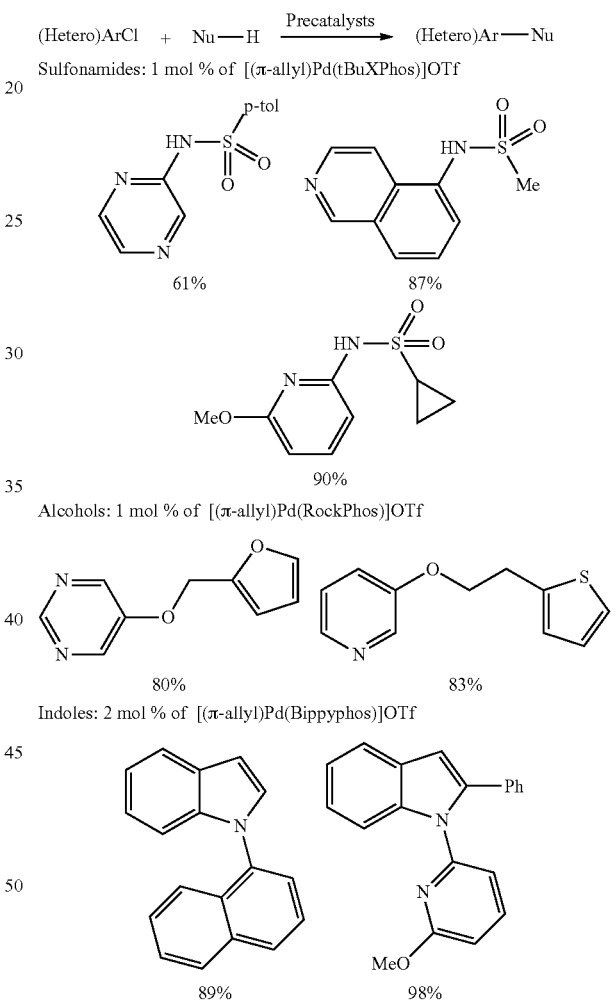

General Procedure for the Sulfonamidation Reactions

An oven dried threaded 2 dram, 17×60 mm reaction vial equipped with a Teflon-coated magnetic stir bar is charged with [(π-allyl)Pd(tBuXPhos)]OTf (7.2 mg, 0.01 mmol, 1 mol %), aryl halide (1.20 mmol, if solid), sulfonamide (1.00 mmol), and K$_3$PO$_4$ (318 mg, 1.50 mmol). The vial is capped with a polypropylene cap with PTFE-faced silicone septum and is evacuated and backfilled with nitrogen through a needle. This evacuation/backfill cycle is repeated two additional times. Anhydrous 2-methyl-2-butanol (4 mL) and the aryl halide (1.20 mmol, if liquid) are added sequentially via syringe. The nitrogen needle is removed and the vial is placed on a preheated aluminum block (110° C.) and stirred for 3 hours. The vial is then removed from the heating block and allowed to cool to room temperature. Saturated ammonium chloride (10 mL) is added, and the aqueous phase is extracted with EtOAc (3×10 mL). The organic extracts are combined, dried over anhydrous MgSO₄, filtered, and concentrated in vacuo. The residue is chromatographed on silica gel using a Teledyne ISCO CombiFlashRf.

4-methyl-N-(pyrazin-2-yl)benzenesulfonamide

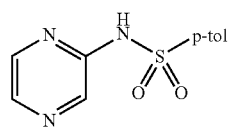

According to the general procedure, a mixture of 2-chloropyrazine (107 µL, 1.20 mmol), p-toluenesulfonamide (171 mg, 1.00 mmol), K₃PO₄ (318 mg, 1.50 mmol), [(π-allyl)Pd(tBuXPhos)]OTf (7.2 mg, 0.01 mmol), and 4 mL of anhydrous 2-methyl-2-butanol are stirred at 110° C. for 3 hours. The crude material is chromatographed on silica gel with a gradient of 0-100% EtOAc/hexanes as the eluent to give 152 mg (0.61 mmol, 61%) of 4-methyl-N-(pyrazin-2-yl)benzenesulfonamide as a white solid. The spectroscopic properties match those previously reported (Baffoe, J.; Hoe, M. Y.; Touré, B. B. *Org. Lett.* 2010, 12, 1532).

N-(isoquinolin-5-yl)methanesulfonamide

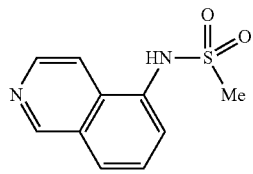

According to the general procedure, a mixture of 5-bromoisoquinoline (250 mg, 1.20 mmol), methanesulfonamide (95 mg, 1.00 mmol), K₃PO₄ (318 mg, 1.50 mmol), [(π-allyl)Pd(tBuXPhos)]OTf (7.2 mg, 0.01 mmol), and 4 mL of anhydrous 2-methyl-2-butanol are stirred at 110° C. for 3 hours. The crude material is chromatographed on silica gel with a gradient of 0-5% MeOH/CH₂Cl₂ as the eluent to give 194 mg (0.87 mmol, 87%) of N-(isoquinolin-5-yl)methanesulfonamide as an off-white solid.

¹H NMR (400 MHz, DMSO-d₆, δ): 9.92 (s, 1H), 9.34 (s, 1H), 8.58 (app d, J=5.9 Hz, 1H), 8.12 (app d, J=5.9 Hz, 1H), 8.03 (app d, J=8.1 Hz, 1H), 7.78 (app d, J=7.4 Hz, 1H), 7.69 (app t, J=7.9 Hz, 1H), 3.06 (s, 3H).

¹³C NMR (100 MHz, DMSO-d₆, δ): 152.4, 143.1, 132.3, 131.7, 129.0, 127.4, 126.6, 125.9, 116.0, 39.92.

Anal. Calcd. for C₁₀H₁₀N₂O₂S: C, 54.04; H, 4.54; N, 12.60. Found: C, 54.05; H, 4.26; N, 12.38.

N-(6-methoxypyridin-2-yl)cyclopropanesulfonamide

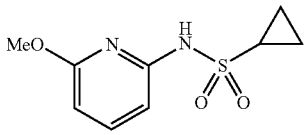 [SMILES: COc1cccc(NS(=O)(=O)C2CC2)n1]

According to the general procedure, a mixture of 2-chloro-6-methoxypyridine (143 µL, 1.20 mmol), cyclopropanesulfonamide (121 mg, 1.00 mmol), K₃PO₄ (318 mg, 1.50 mmol), [(π-allyl)Pd(tBuXPhos)]OTf (7.2 mg, 0.01 mmol), and 4 mL of anhydrous 2-methyl-2-butanol are stirred at 110° C. for 3 hours. The crude material is chromatographed on silica gel with a gradient of 0-40% EtOAc/hexanes as the eluent to give 207 mg (0.90 mmol, 90%) of N-(6-methoxypyridin-2-yl)cyclopropanesulfonamide as a white solid.

¹H NMR (400 MHz, CDCl₃, δ): 7.52 (t, J=7.9 Hz, 1H), 7.00 (bs, 1H), 6.79 (d, J=7.8 Hz, 1H), 6.45 (d, J=8.1 Hz, 1H), 3.86 (s, 3H), 2.79-2.73 (m, 1H), 1.30-1.26 (m, 2H), 1.03-0.98 (m, 2H).

¹³C NMR (100 MHz, CDCl₃, δ): 163.7, 149.1, 141.0, 105.8, 103.6, 53.9, 31.3, 6.1.

Anal. Calcd. for C₉H₁₂N₂O₃S: C, 47.36; H, 5.30; N, 12.27. Found: C, 47.42; H, 5.27; N, 12.19.

General Procedure for the C—O Coupling Reactions

An oven dried threaded 2 dram, 17×60 mm reaction vial equipped with a Teflon-coated magnetic stir bar is charged with [(π-allyl)Pd(RockPhos)]OTf (7.7 mg, 0.01 mmol, 1 mol %), aryl halide (1.00 mmol, if solid), and K₃PO₄ (318 mg, 1.50 mmol). The vial is capped with a polypropylene cap with PTFE-faced silicone septum and is evacuated and backfilled with nitrogen through a needle. This evacuation/backfill cycle is repeated two additional times. Anhydrous toluene (1 mL), the aryl halide (1.00 mmol, if liquid), and alcohol (1.50 mmol) are added sequentially via syringe. The nitrogen needle is removed and the vial is placed on a preheated aluminum block (100° C.) and stirred for 16 hours. The vial is then removed from the heating block and allowed to cool to room temperature. The reaction mixture is diluted with 10 mL of EtOAc, filtered through a pad of Celite, and concentrated in vacuo. The residue is chromatographed on silica gel using a Teledyne ISCO CombiFlashRf.

5-(furan-2-ylmethoxy)pyrimidine

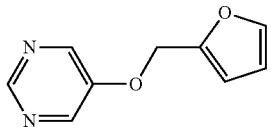 [SMILES: c1coc(COc2cncnc2)c1]

According to the general procedure, a mixture of 5-bromopyrimidine (159 mg, 1.00 mmol), furfuryl alcohol (130 µL, 1.50 mmol), K₃PO₄ (318 mg, 1.50 mmol), [(π-allyl)Pd(RockPhos)]OTf (7.7 mg, 0.01 mmol), and 1 mL of anhydrous toluene are stirred at 100° C. for 16 hours. The crude material is chromatographed on silica gel with a gradient of 0-50% EtOAc/hexanes as the eluent to give 141 mg (0.80 mmol, 80%) of 5-(furan-2-ylmethoxy)pyrimidine as a yellow oil.

¹H NMR (400 MHz, CDCl₃, δ): 8.83 (s, 1H), 8.46 (s, 2H), 7.43 (s, 1H), 6.45 (app d, J=2.9 Hz, 1H), 6.37-6.36 (m, 1H), 5.08 (s, 2H).

¹³C NMR (100 MHz, CDCl₃, δ): 152.6, 152.1, 148.8, 144.4, 143.9, 111.4, 110.9, 63.0.

HRMS (ESI) m/z: [M+H]⁺ Calcd. for C₉H₉N₂O₂: 177.0664. Found: 177.0661.

3-(2-(thiophen-2-yl)ethoxy)pyridine

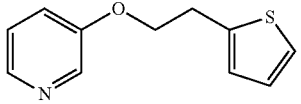 [SMILES: c1cncc(OCCc2cccs2)c1]

According to the general procedure, a mixture of 3-chloropyridine (94 µL, 1.00 mmol), 2-thiopheneethanol (167 µL, 1.50 mmol), K₃PO₄ (318 mg, 1.50 mmol), [(π-allyl)Pd(RockPhos)]OTf (7.7 mg, 0.01 mmol), and 1 mL of anhydrous toluene are stirred at 100° C. for 16 hours. The crude material is chromatographed on silica gel with a gradient of 0-100% EtOAc/hexanes as the eluent to give 170 mg (0.83 mmol, 83%) of 3-(2-(thiophen-2-yl)ethoxy)pyridine as a colorless oil.

¹H NMR (400 MHz, CDCl₃, δ): 8.31 (s, 1H), 8.20 (s, 1H), 7.18-7.15 (m, 3H), 6.95-6.90 (m, 2H), 4.21 (t, J=6.7 Hz, 2H), 3.31 (t, J=6.7 Hz, 2H).

¹³C NMR (100 MHz, CDCl₃, δ): 155.0, 142.6, 140.0, 138.3, 127.1, 125.9, 124.3, 124.0, 121.4, 68.9, 30.1.

Anal. Calcd. for C₁₁H₁₁NOS: C, 64.36; H, 5.40; N, 6.82. Found: C, 64.31; H, 5.64; N, 6.91.

Indole Arylation Reactions 1-(naphthalen-1-yl)-1H-indole

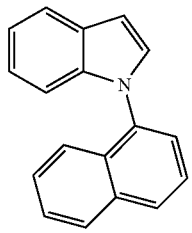 [SMILES: c1ccc2c(-n3ccc4ccccc43)cccc2c1]

An oven dried threaded 2 dram, 17×60 mm reaction vial equipped with a Teflon-coated magnetic stir bar is charged with [(π-allyl)Pd(Bippyphos)]OTf (8.0 mg, 0.01 mmol, 2 mol %), BippyPhos (5.1 mg, 0.01 mmol, 2 mol %), indole (58.6 mg, 0.50 mmol), and NaOt-Bu (67.3 mg, 0.70 mmol). The vial is capped with a polypropylene cap with PTFE-faced silicone septa and is evacuated and backfilled with nitrogen through a needle. This evacuation/backfill cycle is repeated two additional times. Anhydrous toluene (2 mL) and 1-bromonaphthalene (70.0 µL, 0.50 mmol) are added sequentially via syringe. The nitrogen needle is removed and the vial is placed on a preheated aluminum block (110° C.) and stirred for 16 hours. The tube is then removed from the heating block and allowed to cool to room temperature. The reaction mixture is diluted with 5 mL of EtOAc, filtered through a pad of Celite, and concentrated in vacuo. The residue is chromatographed on silica gel using a Teledyne ISCO CombiFlashRf with a gradient of 0-5% EtOAc/hexanes as the eluent to give 109 mg (0.45 mmol, 89%) of 1-(naphthalen-1-yl)-1H-indole as a white solid. The spectroscopic properties match those previously reported (Diness, F.; Fairlie, D. P. Angew. Chem. Int. Ed. 2012, 51, 8012).

1-(6-methoxypyridin-2-yl)-2-phenyl-1H-indole

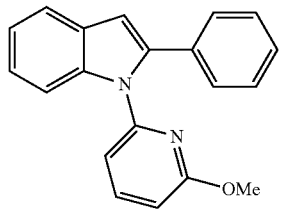 [SMILES: COc1cccc(-n2c(-c3ccccc3)cc3ccccc32)n1]

An oven dried threaded 2 dram, 17×60 mm reaction vial equipped with a Teflon-coated magnetic stir bar is charged with [(π-allyl)Pd(Bippyphos)]OTf (16 mg, 0.02 mmol, 2 mol %), BippyPhos (10 mg, 0.02 mmol, 2 mol %), 2-phenylindole (193 mg, 1.00 mmol), and NaOt-Bu (135 mg, 1.40 mmol). The vial is capped with a polypropylene cap with PTFE-faced silicone septum and is evacuated and backfilled with nitrogen. This evacuation/backfill cycle is repeated two additional times. Anhydrous toluene (4 mL) and 2-chloro-6-methoxypyridine (119 µL, 1.00 mmol) are added sequentially via syringe. The nitrogen needle is removed and the vial is placed on a preheated aluminum block (110° C.) and stirred for 16 hours. The tube is then removed from the heating block and allowed to cool to room temperature. The reaction mixture is diluted with 10 mL of EtOAc, filtered through a pad of Celite, and concentrated in vacuo. The residue is chromatographed on silica gel using a Teledyne ISCO CombiFlashRf with a gradient of 0-5% EtOAc/hexanes as the eluent to give 293 mg (0.98 mmol, 98%) of 1-(6-methoxypyridin-2-yl)-2-phenyl-1H-indole as a colorless oil.

¹H NMR (400 MHz, CDCl₃, δ): 7.75 (d, J=7.8 Hz, 1H), 7.69 (d, J=7.8 Hz, 1H), 7.55 (t, J=7.8 Hz, 1H), 7.31-7.20 (m, 7H), 6.80 (s, 1H), 6.67-6.62 (m, 2H), 3.76 (s, 3H).

¹³C NMR (100 MHz, CDCl₃, δ): 163.7, 149.6, 140.6, 140.1, 138.4, 133.5, 129.0, 128.9, 128.3, 127.5, 123.0, 121.5, 120.8, 113.6, 111.7, 108.6, 105.6, 53.8.

The invention claimed is:

1. A palladium(II) complex of formula (1):

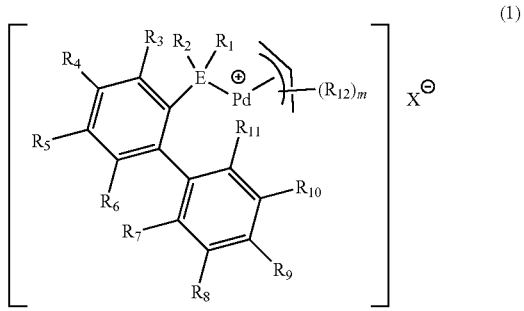

wherein:

Pd⊕ is a cationic palladium atom;

R₁ and R₂ are, independently, an organic group having 1-20 carbon atoms, or R₁ and R₂ are linked to form a ring structure with E;

R₃, R₄, R₅, R₆, R₇, R₈, R₉, R₁₀ and R₁₁ are, independently, —H or an organic group having 1-20 carbon atoms; or R₁/R₃ or R₂/R₃ forms a ring structure with the atoms to which they are attached and in this instance R₄/R₅, R₅/R₆, R₇/R₈, R₈/R₉, R₉/R₁₀ or R₁₀/R₁₁, independently, form a ring structure with the carbon atoms to which they are attached or R₁, R₂, R₄, R₅, R₆, R₇, R₈, R₉, R₁₀ and R₁₁ are as defined above;

R₁₂ is an organic group having 1-20 carbon atoms;

m is 0, 1, 2, 3, 4 or 5;

E is P or As; and

X⁻ is a non-coordinated anionic ligand.

2. A palladium(II) complex according to claim 1, wherein E is P.

3. A palladium(II) complex according to claim 1, wherein R₁ and R₂ are, independently, substituted or unsubstituted straight-chain alkyl, substituted or unsubstituted branched-chain alkyl, substituted or unsubstituted cycloalkyl, substituted or unsubstituted aryl, or substituted or unsubstituted heteroaryl wherein the heteroatoms of the substituted or unsubstituted heteroaryl are, independently, sulfur, nitrogen or oxygen.

4. A palladium(II) complex according to claim 1, wherein R₃, R₄, R₅ and R₆ are, independently, —H, substituted or unsubstituted straight-chain alkyl, substituted or unsubstituted branched-chain alkyl, substituted or unsubstituted cycloalkyl, substituted or unsubstituted alkoxy, substituted or unsubstituted aryl, substituted or unsubstituted heteroaryl, substituted or unsubstituted —N(alkyl)₂ (wherein the alkyl is the same or different and is, independently, a straight-chain or branched-chain alkyl), substituted or unsubstituted —N(cycloalkyl)₂ (wherein the cycloalkyl is the same or different), substituted or unsubstituted —N(aryl)₂ (wherein the aryl is the same or different), substituted or unsubstituted —N(heteroaryl)₂ (wherein the heteroaryl is the same or different) or substituted or unsubstituted heterocycloalkyl.

5. A palladium(II) complex according to claim 4, wherein R₃, R₄, R₅ and R₆ are —H.

6. A palladium(II) complex according to claim 4, wherein R₃, R₄, R₅ and R₆ are, independently, a straight-chain alkyl.

7. A palladium(II) complex according to claim 1, wherein two of R₃, R₄, R₅ and R₆ are —H, and the other two of R₃, R₄, R₅ and R₆ are, independently, unsubstituted straight-chain alkyl, unsubstituted branched-chain alkyl, unsubstituted cycloalkyl, or unsubstituted alkoxy.

8. A palladium(II) complex according to claim 1, wherein R₇, R₈, R₉, R₁₀ and R₁₁ are, independently, —H, substituted or unsubstituted straight-chain alkyl, substituted or unsubstituted branched-chain alkyl, substituted or unsubstituted cycloalkyl, substituted or unsubstituted alkoxy, substituted or unsubstituted aryl, substituted or unsubstituted heteroaryl, substituted or unsubstituted —N(alkyl)₂ (wherein the alkyl is the same or different and is, independently, a straight-chain or branched-chain alkyl), substituted or unsubstituted —N(cycloalkyl)₂ (wherein the cycloalkyl is the same or different), substituted or unsubstituted —N(aryl)₂ (wherein the aryl is the same or different), substituted or unsubstituted —N(heteroaryl)₂ (wherein the heteroaryl is the same or different) or substituted or unsubstituted heterocycloalkyl.

9. A palladium(II) complex according to claim 7, wherein R₇, R₈, R₉, R₁₀ and R₁₁ are —H.

10. A palladium(II) complex according to claim 7, wherein three of R₇, R₈, R₉, R₁₀ and R₁₁ are —H, and the other two of R₇, R₈, R₉, R₁₀ and R₁₁ are, independently, unsubstituted straight-chain alkyl, unsubstituted branched-chain alkyl, unsubstituted cycloalkyl, unsubstituted alkoxy, unsubstituted —N(alkyl)₂ (wherein the alkyl is the same or different and, independently, straight-chain or branched-chain alkyl), or unsubstituted —N(aryl)₂ (wherein the aryl is the same or different).

11. A palladium(II) complex according to claim 7, wherein two of R₇, R₈, R₉, R₁₀ and R₁₁ are —H, and the other three of R₇, R₈, R₉, R₁₀ and R₁₁ are, independently, unsubstituted straight-chain alkyl, unsubstituted branched-chain alkyl, unsubstituted cycloalkyl, unsubstituted alkoxy, unsubstituted —N(alkyl)₂ (wherein the alkyl is the same or different and, independently, straight-chain or branched-chain alkyl) or unsubstituted —N(aryl)₂ (wherein the aryl is the same or different).

12. A palladium(II) complex according to claim 1, wherein the

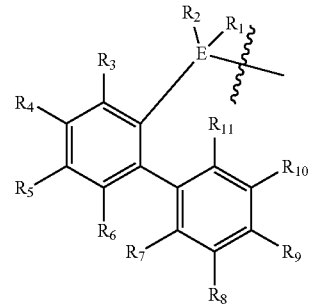

moiety is a monodentate tertiary phosphine ligand that is:

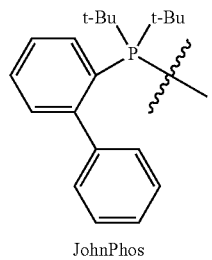 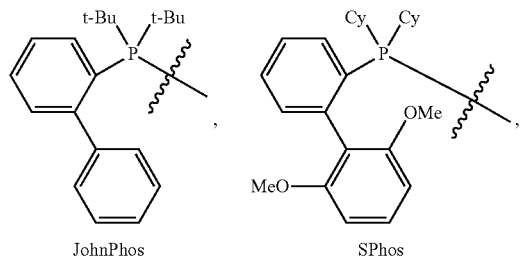

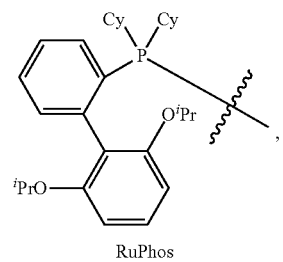 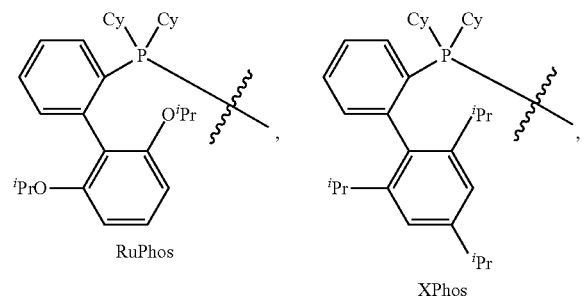

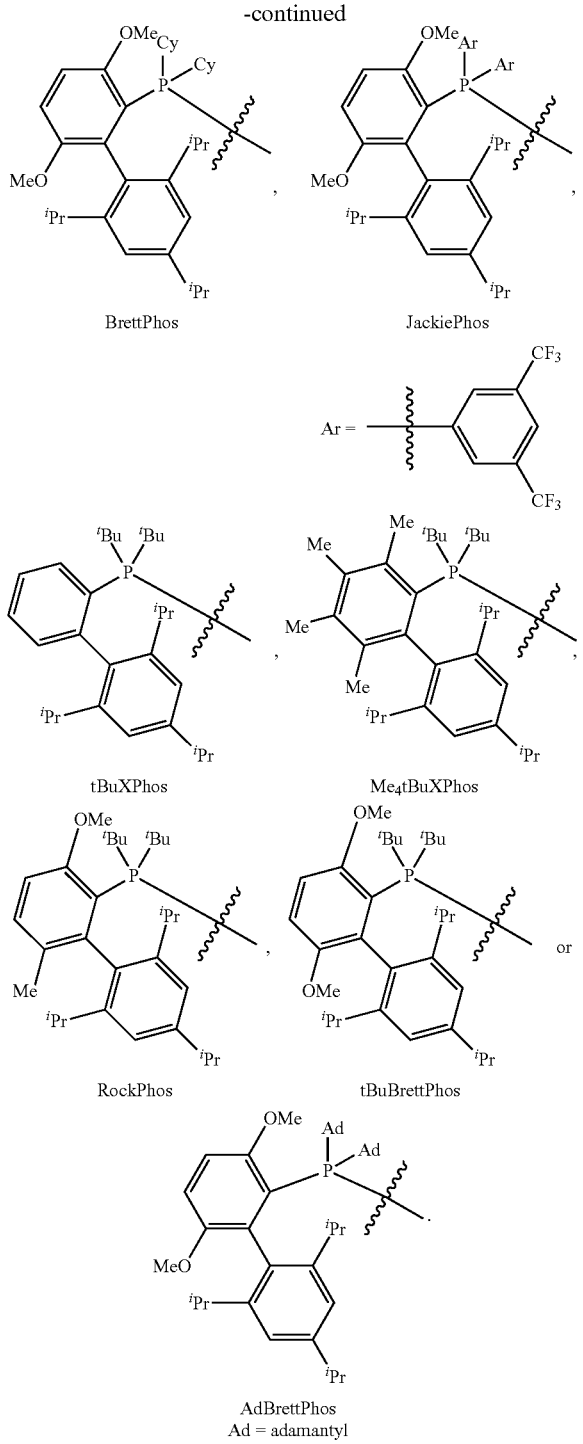

BrettPhos, JackiePhos

Ar = tBuXPhos, Me₄tBuXPhos

RockPhos, tBuBrettPhos

AdBrettPhos
Ad = adamantyl

13. A palladium(II) complex according to claim 1, wherein each $R_{12}$ is, independently, substituted or unsubstituted straight-chain alkyl, substituted or unsubstituted branched-chain alkyl, substituted or unsubstituted cycloalkyl, substituted or unsubstituted aryl, or substituted or unsubstituted heteroaryl wherein the heteroatoms of the heteroaryl are, independently, sulfur, nitrogen or oxygen.

14. A palladium(II) complex according to claim 1, wherein $X^{\oplus}$ is triflate, tetrafluoroborate, hexafluoroantimonate, hexafluorophosphate, $[B[3,5-(CF_3)_2C_6H_3]_4]^-$ or mesylate.

15. A palladium(II) complex according to claim 1, wherein the complex of formula (1) is:

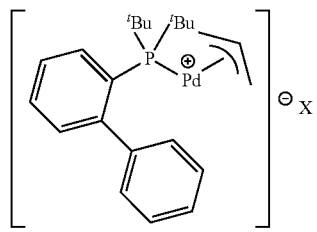

[(π-allyl)Pd(JohnPhos)]X wherein:

X = ⁻OTf: [(π-allyl)Pd(JohnPhos)]OTf;
X = ⁻PF₆: [(π-allyl)Pd(JohnPhos)]PF₆;
X = ⁻BF₄: [(π-allyl)Pd(JohnPhos)]BF₄;
X = ⁻SbF₆: [(π-allyl)Pd(JohnPhos)]SbF₆;
X = [BAr$^F_4$]⁻: [(π-allyl)Pd(JohnPhos)][BAr$^F_4$]; or
X = ⁻OMs: [(π-allyl)Pd(JohnPhos)]OMs,

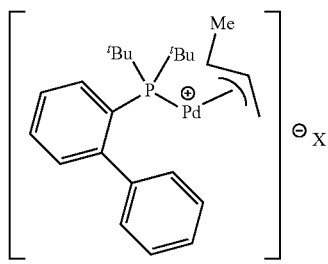

[(π-crotyl)Pd(JohnPhos)]X wherein:

X = ⁻OTf: [(π-crotyl)Pd(JohnPhos)]OTf;
X = ⁻PF₆: [(π-crotyl)Pd(JohnPhos)]PF₆;
X = ⁻BF₄: [(π-crotyl)Pd(JohnPhos)]BF₄;
X = ⁻SbF₆: [(π-crotyl)Pd(JohnPhos)]SbF₆;
X = [BAr$^F_4$]⁻: [(π-crotyl)Pd(JohnPhos)][BAr$^F_4$]; or
X = ⁻OMs: [(π-crotyl)Pd(JohnPhos)]OMs,

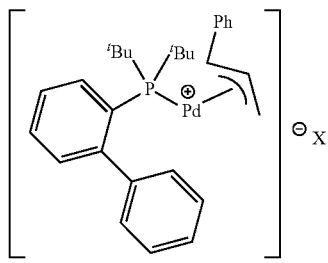

[(π-cinnamyl)Pd(JohnPhos)]X wherein:

X = ⁻OTf: [(π-cinnamyl)Pd(JohnPhos)]OTf;
X = ⁻PF₆: [(π-cinnamyl)Pd(JohnPhos)]PF₆;
X = ⁻BF₄: [(π-cinnamyl)Pd(JohnPhos)]BF₄;
X = ⁻SbF₆: [(π-cinnamyl)Pd(JohnPhos)]SbF₆;
X = [BAr$^F_4$]⁻: [(π-cinnamyl)Pd(JohnPhos)][BAr$^F_4$]; or
X = ⁻OMs: [(π-cinnamyl)Pd(JohnPhos)]OMs,

89
-continued

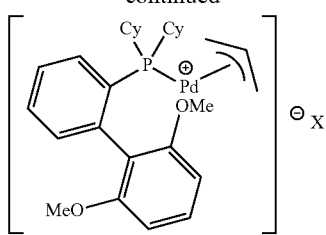

[(π-allyl)Pd(SPhos)]X wherein:
X = ⁻OTf: [(π-allyl)Pd(SPhos)]OTf;
X = ⁻PF$_6$: [(π-allyl)Pd(SPhos)]PF$_6$;
X = ⁻BF$_4$: [(π-allyl)Pd(SPhos)]BF$_4$;
X = ⁻SbF$_6$: [(π-allyl)Pd(SPhos)]SbF$_6$;
X = [BAr$^F_4$]⁻: [(π-allyl)Pd(SPhos)][BAr$^F_4$]; or
X = ⁻OMs: [(π-allyl)Pd(SPhos)]OMs,

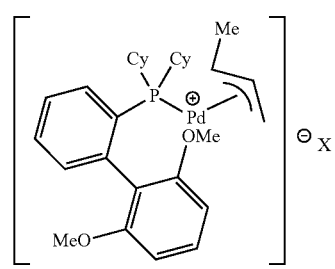

[(π-crotyl)Pd(SPhos)]X wherein:
X = ⁻OTf: [(π-crotyl)Pd(SPhos)]OTf;
X = ⁻PF$_6$: [(π-crotyl)Pd(SPhos)]PF$_6$;
X = ⁻BF$_4$: [(π-crotyl)Pd(SPhos)]BF$_4$;
X = ⁻SbF$_6$: [(π-crotyl)Pd(SPhos)]SbF$_6$;
X = [BAr$^F_4$]⁻: [(π-crotyl)Pd(SPhos)][BAr$^F_4$]; or
X = ⁻OMs: [(π-crotyl)Pd(SPhos)]OMs,

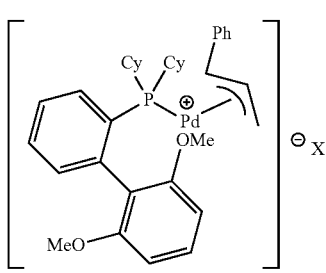

[(π-cinnamyl)Pd(SPhos)]X wherein:
X = ⁻OTf: [(π-cinnamyl)Pd(SPhos)]OTf;
X = ⁻PF$_6$: [(π-cinnamyl)Pd(SPhos)]PF$_6$;
X = ⁻BF$_4$: [(π-cinnamyl)Pd(SPhos)]BF$_4$;
X = ⁻SbF$_6$: [(π-cinnamyl)Pd(SPhos)]SbF$_6$;
X = [BAr$^F_4$]⁻: [(π-cinnamyl)Pd(SPhos)][BAr$^F_4$]; or
X = ⁻OMs: [(π-cinnamyl)Pd(SPhos)]OMs,

90
-continued

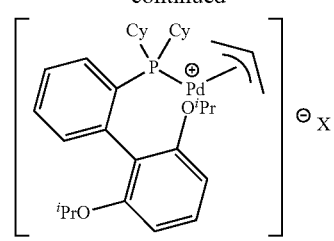

[(π-allyl)Pd(RuPhos)]X wherein:
X = ⁻OTf: [(π-allyl)Pd(RuPhos)]OTf;
X = ⁻PF$_6$: [(π-allyl)Pd(RuPhos)]PF$_6$;
X = ⁻BF$_4$: [(π-allyl)Pd(RuPhos)]BF$_4$;
X = ⁻SbF$_6$: [(π-allyl)Pd(RuPhos)]SbF$_6$;
X = [BAr$^F_4$]⁻: [(π-allyl)Pd(RuPhos)][BAr$^F_4$]; or
X = ⁻OMs: [(π-allyl)Pd(RuPhos)]OMs,

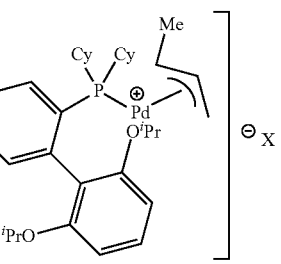

[(π-crotyl)Pd(RuPhos)]X wherein:
X = ⁻OTf: [(π-crotyl)Pd(RuPhos)]OTf;
X = ⁻PF$_6$: [(π-crotyl)Pd(RuPhos)]PF$_6$;
X = ⁻BF$_4$: [(π-crotyl)Pd(RuPhos)]BF$_4$;
X = ⁻SbF$_6$: [(π-crotyl)Pd(RuPhos)]SbF$_6$;
X = [BAr$^F_4$]⁻: [(π-crotyl)Pd(RuPhos)][BAr$^F_4$]; or
X = ⁻OMs: [(π-crotyl)Pd(RuPhos)]OMs,

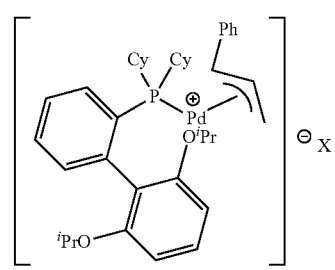

[(π-cinnamyl)Pd(RuPhos)]X wherein:
X = ⁻OTf: [(π-cinnamyl)Pd(RuPhos)]OTf;
X = ⁻PF$_6$: [(π-cinnamyl)Pd(RuPhos)]PF$_6$;
X = ⁻BF$_4$: [(π-cinnamyl)Pd(RuPhos)]BF$_4$;
X = ⁻SbF$_6$: [(π-cinnamyl)Pd(RuPhos)]SbF$_6$;
X = [BAr$^F_4$]⁻: [(π-cinnamyl)Pd(RuPhos)][BAr$^F_4$]; or
X = ⁻OMs: [(π-cinnamyl)Pd(RuPhos)]OMs, -continued

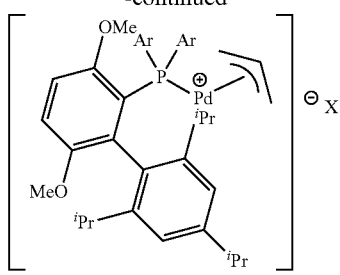

[(π-allyl)Pd(JackiePhos)]X wherein:

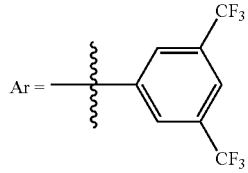

X = ⁻OTf: [(π-allyl)Pd(JackiePhos)]OTf;
X = ⁻PF₆: [(π-allyl)Pd(JackiePhos)]PF₆;
X = ⁻BF₄: [(π-allyl)Pd(JackiePhos)]BF₄;
X = ⁻SbF₆: [(π-allyl)Pd(JackiePhos)]SbF₆;
X = [BAr$^F$₄]⁻: [(π-allyl)Pd(JackiePhos)][BAr$^F$₄]; or
X = ⁻OMs: [(π-allyl)Pd(JackiePhos)]OMs,

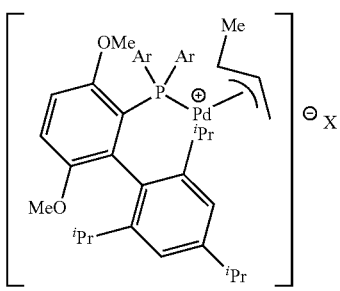

[(π-crotyl)Pd(JackiePhos)]X wherein:

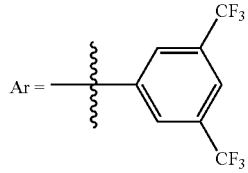

X = ⁻OTf: [(π-crotyl)Pd(JackiePhos)]OTf;
X = ⁻PF₆: [(π-crotyl)Pd(JackiePhos)]PF₆;
X = ⁻BF₄: [(π-crotyl)Pd(JackiePhos)]BF₄;
X = ⁻SbF₆: [(π-crotyl)Pd(JackiePhos)]SbF₆;
X = [BAr$^F$₄]⁻: [(π-crotyl)Pd(JackiePhos)][BAr$^F$₄]; or
X = ⁻OMs: [(π-crotyl)Pd(JackiePhos)]OMs, -continued

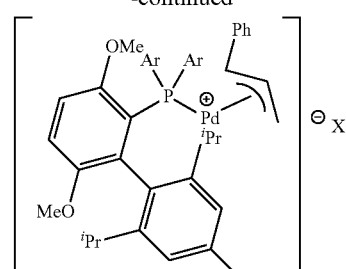

[(π-cinnamyl)Pd(JackiePhos)]X wherein:

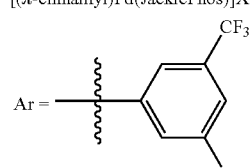

X = ⁻OTf: [(π-cinnamyl)Pd(JackiePhos)]OTf;
X = ⁻PF₆: [(π-cinnamyl)Pd(JackiePhos)]PF₆;
X = ⁻BF₄: [(π-cinnamyl)Pd(JackiePhos)]BF₄;
X = ⁻SbF₆: [(π-cinnamyl)Pd(JackiePhos)]SbF₆;
X = [BAr$^F$₄]⁻: [(π-cinnamyl)Pd(JackiePhos)][BAr$^F$₄]; or
X = ⁻OMs: [(π-cinnamyl)Pd(JackiePhos)]OMs,

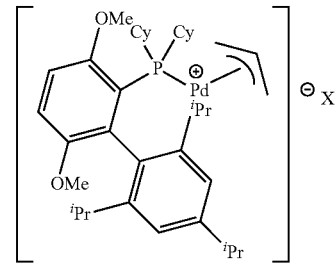

[(π-allyl)Pd(BrettPhos)]X wherein:

X = ⁻OTf: [(π-allyl)Pd(BrettPhos)]OTf;
X = ⁻PF₆: [(π-allyl)Pd(BrettPhos)]PF₆;
X = ⁻BF₄: [(π-allyl)Pd(BrettPhos)]BF₄;
X = ⁻SbF₆: [(π-allyl)Pd(BrettPhos)]SbF₆;
X = [BAr$^F$₄]⁻: [(π-allyl)Pd(BrettPhos)][BAr$^F$₄]; or
X = ⁻OMs: [(π-allyl)Pd(BrettPhos)]OMs,

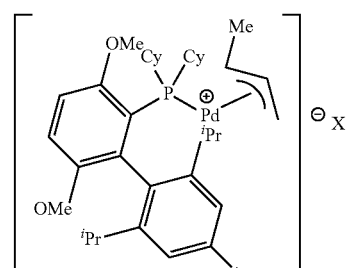

[(π-crotyl)Pd(BrettPhos)]X wherein:

X = ⁻OTf: [(π-crotyl)Pd(BrettPhos)]OTf;
X = ⁻PF₆: [(π-crotyl)Pd(BrettPhos)]PF₆;
X = ⁻BF₄: [(π-crotyl)Pd(BrettPhos)]BF₄;
X = ⁻SbF₆: [(π-crotyl)Pd(BrettPhos)]SbF₆;
X = [BAr$^F$₄]⁻: [(π-crotyl)Pd(BrettPhos)][BAr$^F$₄]; or
X = ⁻OMs: [(π-crotyl)Pd(BrettPhos)]OMs,

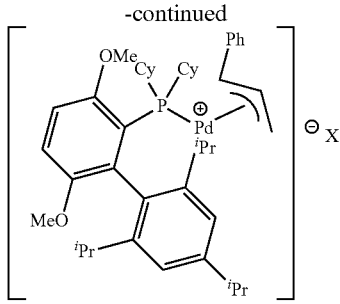

[(π-cinnamyl)Pd(BrettPhos)]X wherein:
X = ⁻OTf: [(π-cinnamyl)Pd(BrettPhos)]OTf;
X = ⁻PF₆: [(π-cinnamyl)Pd(BrettPhos)]PF₆;
X = ⁻BF₄: [(π-cinnamyl)Pd(BrettPhos)]BF₄;
X = ⁻SbF₆: [(π-cinnamyl)Pd(BrettPhos)]SbF₆;
X = [BAr$^F_4$]⁻: [(π-cinnamyl)Pd(BrettPhos)][BAr$^F_4$]; or
X = ⁻OMs: [(π-cinnamyl)Pd(BrettPhos)]OMs,

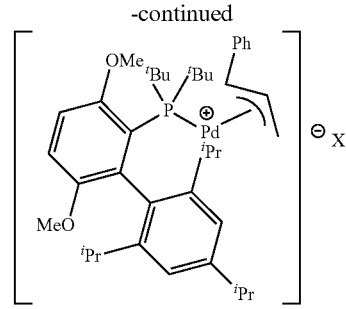

[(π-cinnamyl)Pd(tBuBrettPhos)]X wherein:
X = ⁻OTf: [(π-cinnamyl)Pd(tBuBrettPhos)]OTf;
X = ⁻PF₆: [(π-cinnamyl)Pd(tBuBrettPhos)]PF₆;
X = ⁻BF₄: [(π-cinnamyl)Pd(tBuBrettPhos)]BF₄;
X = ⁻SbF₆: [(π-cinnamyl)Pd(tBuBrettPhos)]SbF₆;
X = [BAr$^F_4$]⁻: [(π-cinnamyl)Pd(tBuBrettPhos)][BAr$^F_4$]; or
X = ⁻OMs: [(π-cinnamyl)Pd(tBuBrettPhos)]OMs,

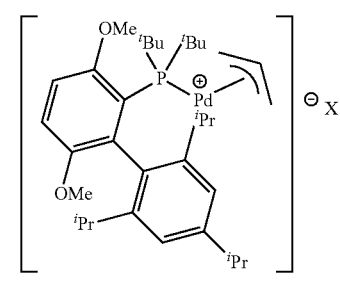

[(π-allyl)Pd(tBuBrettPhos)]X wherein:
X = ⁻OTf: [(π-allyl)Pd(tBuBrettPhos)]OTf;
X = ⁻PF₆: [(π-allyl)Pd(tBuBrettPhos)]PF₆;
X = ⁻BF₄: [(π-allyl)Pd(tBuBrettPhos)]BF₄;
X = ⁻SbF₆: [(π-allyl)Pd(tBuBrettPhos)]SbF₆;
X = [BAr$^F_4$]⁻: [(π-allyl)Pd(tBuBrettPhos)][BAr$^F_4$]; or
X = ⁻OMs: [(π-allyl)Pd(tBuBrettPhos)]OMs,

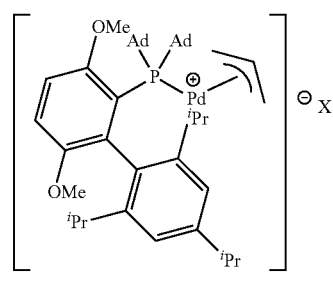

[(π-allyl)Pd(AdBrettPhos)]X wherein:
X = ⁻OTf: [(π-allyl)Pd(AdBrettPhos)]OTf;
X = ⁻PF₆: [(π-allyl)Pd(AdBrettPhos)]PF₆;
X = ⁻BF₄: [(π-allyl)Pd(AdBrettPhos)]BF₄;
X = ⁻SbF₆: [(π-allyl)Pd(AdBrettPhos)]SbF₆;
X = [BAr$^F_4$]⁻: [(π-allyl)Pd(AdBrettPhos)][BAr$^F_4$]; or
X = ⁻OMs: [(π-allyl)Pd(AdBrettPhos)]OMs,

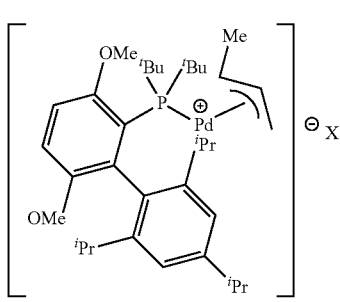

[(π-crotyl)Pd(tBuBrettPhos)]X wherein:
X = ⁻OTf: [(π-crotyl)Pd(tBuBrettPhos)]OTf;
X = ⁻PF₆: [(π-crotyl)Pd(tBuBrettPhos)]PF₆;
X = ⁻BF₄: [(π-crotyl)Pd(tBuBrettPhos)]BF₄;
X = ⁻SbF₆: [(π-crotyl)Pd(tBuBrettPhos)]SbF₆;
X = [BAr$^F_4$]⁻: [(π-crotyl)Pd(tBuBrettPhos)][BAr$^F_4$]; or
X = ⁻OMs: [(π-crotyl)Pd(tBuBrettPhos)]OMs,

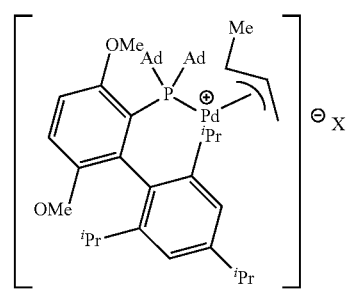

[(π-crotyl)Pd(AdBrettPhos)]X wherein:
X = ⁻OTf: [(π-crotyl)Pd(AdBrettPhos)]OTf;
X = ⁻PF₆: [(π-crotyl)Pd(AdBrettPhos)]PF₆;
X = ⁻BF₄: [(π-crotyl)Pd(AdBrettPhos)]BF₄;
X = ⁻SbF₆: [(π-crotyl)Pd(AdBrettPhos)]SbF₆;
X = [BAr$^F_4$]⁻: [(π-crotyl)Pd(AdBrettPhos)][BAr$^F_4$]; or
X = ⁻OMs: [(π-crotyl)Pd(AdBrettPhos)]OMs,

95

-continued

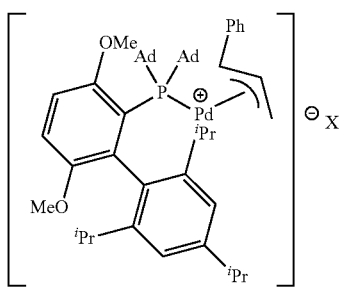

[(π-cinnamyl)Pd(AdBrettPhos)]X wherein:
X = ⁻OTf: [(π-cinnamyl)Pd(AdBrettPhos)]OTf;
X = ⁻PF$_6$: [(π-cinnamyl)Pd(AdBrettPhos)]PF$_6$;
X = ⁻BF$_4$: [(π-cinnamyl)Pd(AdBrettPhos)]BF$_4$;
X = ⁻SbF$_6$: [(π-cinnamyl)Pd(AdBrettPhos)]SbF$_6$;
X = [BAr$^F_4$]⁻: [(π-cinnamyl)Pd(AdBrettPhos)][BAr$^F_4$]; or
X = ⁻OMs: [(π-cinnamyl)Pd(AdBrettPhos)]OMs,

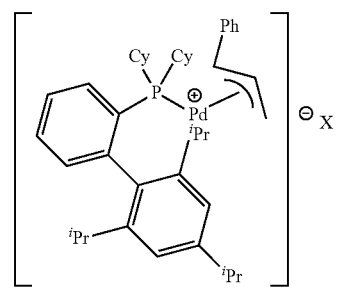

[(π-allyl)Pd(XPhos)]X wherein:
X = ⁻OTf: [(π-allyl)Pd(XPhos)]OTf;
X = ⁻PF$_6$: [(π-allyl)Pd(XPhos)]PF$_6$;
X = ⁻BF$_4$: [(π-allyl)Pd(XPhos)]BF$_4$;
X = ⁻SbF$_6$: [(π-allyl)Pd(XPhos)]SbF$_6$;
X = [BAr$^F_4$]⁻: [(π-allyl)Pd(XPhos)][BAr$^F_4$]; or
X = ⁻OMs: [(π-allyl)Pd(XPhos)]OMs,

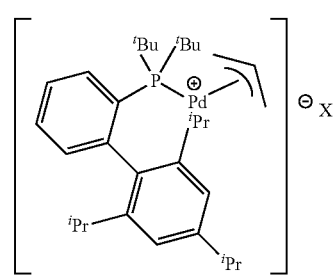

[(π-crotyl)Pd(XPhos)]X wherein:
X = ⁻OTf: [(π-crotyl)Pd(XPhos)]OTf;
X = ⁻PF$_6$: [(π-crotyl)Pd(XPhos)]PF$_6$;
X = ⁻BF$_4$: [(π-crotyl)Pd(XPhos)]BF$_4$;
X = ⁻SbF$_6$: [(π-crotyl)Pd(XPhos)]SbF$_6$;
X = [BAr$^F_4$]⁻: [(π-crotyl)Pd(XPhos)][BAr$^F_4$]; or
X = ⁻OMs: [(π-crotyl)Pd(XPhos)]OMs,

96

-continued

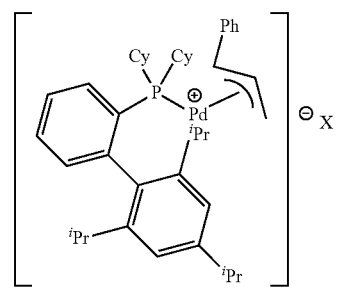

[(π-cinnamyl)Pd(XPhos)]X wherein:
X = ⁻OTf: [(π-cinnamyl)Pd(XPhos)]OTf;
X = ⁻PF$_6$: [(π-cinnamyl)Pd(XPhos)]PF$_6$;
X = ⁻BF$_4$: [(π-cinnamyl)Pd(XPhos)]BF$_4$;
X = ⁻SbF$_6$: [(π-cinnamyl)Pd(XPhos)]SbF$_6$;
X = [BAr$^F_4$]⁻: [(π-cinnamyl)Pd(XPhos)][BAr$^F_4$]; or
X = ⁻OMs: [(π-cinnamyl)Pd(XPhos)]OMs,

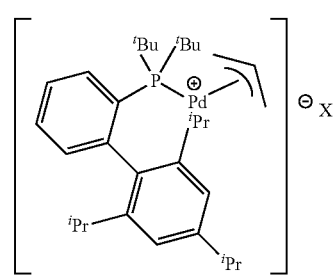

[(π-allyl)Pd(tBuXPhos)]X wherein:
X = ⁻OTf: [(π-allyl)Pd(tBuXPhos)]OTf;
X = ⁻PF$_6$: [(π-allyl)Pd(tBuXPhos)]PF$_6$;
X = ⁻BF$_4$: [(π-allyl)Pd(tBuXPhos)]BF$_4$;
X = ⁻SbF$_6$: [(π-allyl)Pd(tBuXPhos)]SbF$_6$;
X = [BAr$^F_4$]⁻: [(π-allyl)Pd(tBuXPhos)][BAr$^F_4$]; or
X = ⁻OMs: [(π-allyl)Pd(tBuXPhos)]OMs,

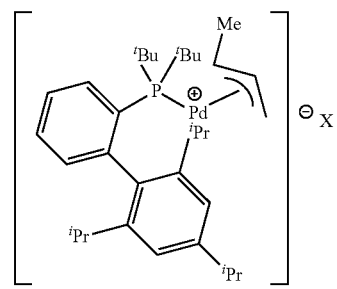

[(π-crotyl)Pd(tBuXPhos)]X wherein:
X = ⁻OTf: [(π-crotyl)Pd(tBuXPhos)]OTf;
X = ⁻PF$_6$: [(π-crotyl)Pd(tBuXPhos)]PF$_6$;
X = ⁻BF$_4$: [(π-crotyl)Pd(tBuXPhos)]BF$_4$;
X = ⁻SbF$_6$: [(π-crotyl)Pd(tBuXPhos)]SbF$_6$;
X = [BAr$^F_4$]⁻: [(π-crotyl)Pd(tBuXPhos)][BAr$^F_4$]; or
X = ⁻OMs: [(π-crotyl)Pd(tBuXPhos)]OMs, -continued

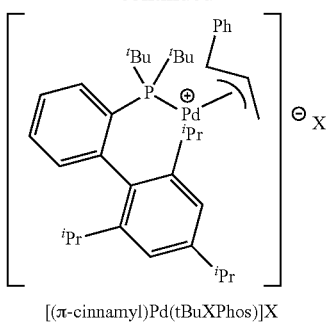

[(π-cinnamyl)Pd(tBuXPhos)]X wherein:
X = ⁻OTf: [(π-cinnamyl)Pd(tBuXPhos)]OTf;
X = ⁻PF₆: [(π-cinnamyl)Pd(tBuXPhos)]PF₆;
X = ⁻BF₄: [(π-cinnamyl)Pd(tBuXPhos)]BF₄;
X = ⁻SbF₆: [(π-cinnamyl)Pd(tBuXPhos)]SbF₆;
X = [BAr$^F_4$]⁻: [(π-cinnamyl)Pd(tBuXPhos)][BAr$^F_4$]; or
X = ⁻OMs: [(π-cinnamyl)Pd(tBuXPhos)]OMs,

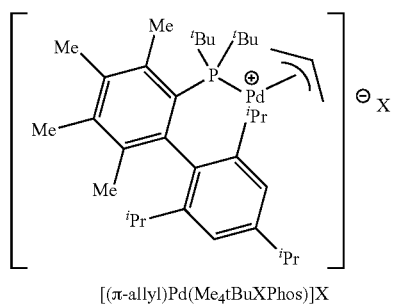

[(π-allyl)Pd(Me₄tBuXPhos)]X wherein:
X = ⁻OTf: [(π-allyl)Pd(Me₄tBuXPhos)]OTf;
X = ⁻PF₆: [(π-allyl)Pd(Me₄tBuXPhos)]PF₆;
X = ⁻BF₄: [(π-allyl)Pd(Me₄tBuXPhos)]BF₄;
X = ⁻SbF₆: [(π-allyl)Pd(Me₄tBuXPhos)]SbF₆;
X = [BAr$^F_4$]⁻: [(π-allyl)Pd(Me₄tBuXPhos)][BAr$^F_4$]; or
X = ⁻OMs: [(π-allyl)Pd(Me₄tBuXPhos)]OMs,

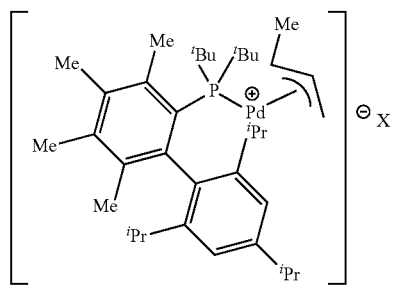

[(π-crotyl)Pd(Me₄tBuXPhos)]X wherein:
X = ⁻OTf: [(π-crotyl)Pd(Me₄tBuXPhos)]OTf;
X = ⁻PF₆: [(π-crotyl)Pd(Me₄tBuXPhos)]PF₆;
X = ⁻BF₄: [(π-crotyl)Pd(Me₄tBuXPhos)]BF₄;
X = ⁻SbF₆: [(π-crotyl)Pd(Me₄tBuXPhos)]SbF₆;
X = [BAr$^F_4$]⁻: [(π-crotyl)Pd(Me₄tBuXPhos)][BAr$^F_4$]; or
X = ⁻OMs: [(π-crotyl)Pd(Me₄tBuXPhos)]OMs, -continued

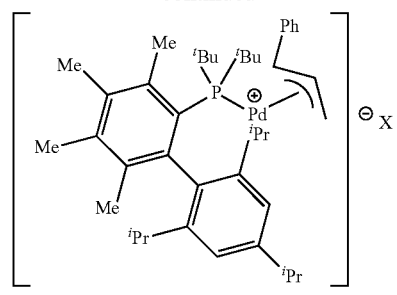

[(π-cinnamyl)Pd(Me₄tPhos)]X wherein:
X = ⁻OTf: [(π-cinnamyl)Pd(Me₄tBuXPhos)]OTf;
X = ⁻PF₆: [(π-cinnamyl)Pd(Me₄tBuXPhos)]PF₆;
X = ⁻BF₄: [(π-cinnamyl)Pd(Me₄tBuXPhos)]BF₄;
X = ⁻SbF₆: [(π-cinnamyl)Pd(Me₄tBuXPhos)]SbF₆;
X = [BAr$^F_4$]⁻: [(π-cinnamyl)Pd(Me₄tBuXPhos)][BAr$^F_4$]; or
X = ⁻OMs: [(π-cinnamyl)Pd(Me₄tBuXPhos)]OMs,

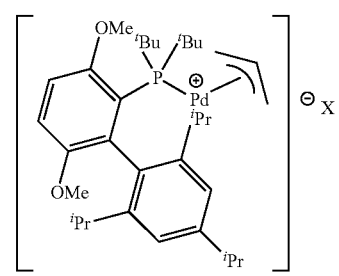

[(π-allyl)Pd(RockPhos)]X wherein:
X = ⁻OTf: [(π-allyl)Pd(RockPhos)]OTf;
X = ⁻PF₆: [(π-allyl)Pd(RockPhos)]PF₆;
X = ⁻BF₄: [(π-allyl)Pd(RockPhos)]BF₄;
X = ⁻SbF₆: [(π-allyl)Pd(RockPhos)]SbF₆;
X = [BAr$^F_4$]⁻: [(π-allyl)Pd(RockPhos)][BAr$^F_4$]; or
X = ⁻OMs: [(π-allyl)Pd(RockPhos)]OMs,

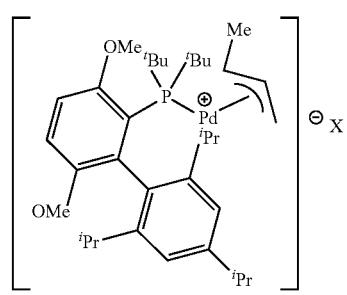

[(π-crotyl)Pd(RockPhos)]X wherein:
X = ⁻OTf: [(π-crotyl)Pd(RockPhos)]OTf;
X = ⁻PF₆: [(π-crotyl)Pd(RockPhos)]PF₆;
X = ⁻BF₄: [(π-crotyl)Pd(RockPhos)]BF₄;
X = ⁻SbF₆: [(π-crotyl)Pd(RockPhos)]SbF₆;
X = [BAr$^F_4$]⁻: [(π-crotyl)Pd(RockPhos)][BAr$^F_4$]; or
X = ⁻OMs: [(π-crotyl)Pd(RockPhos)]OMs, or -continued

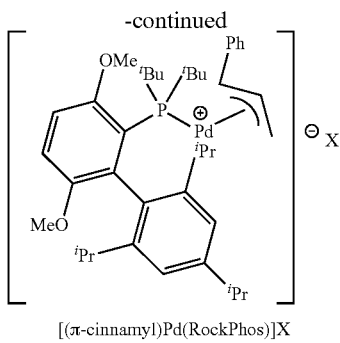

[(π-cinnamyl)Pd(RockPhos)]X wherein:
X = ⁻OTf: [(π-cinnamyl)Pd(RockPhos)]OTf;
X = ⁻PF₆: [(π-cinnamyl)Pd(RockPhos)]PF₆;
X = ⁻BF₄: [(π-cinnamyl)Pd(RockPhos)]BF₄;
X = ⁻SbF₆: [(π-cinnamyl)Pd(RockPhos)]SbF₆;
X = [BAr$^F_4$]⁻: [(π-cinnamyl)Pd(RockPhos)][BAr$^F_4$]; or
X = ⁻OMs: [(π-cinnamyl)Pd(RockPhos)]OMs.

16. A palladium(II) complex of formula (3):

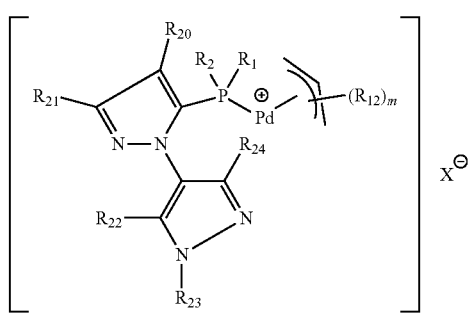

(3)

wherein:
$R_1$ and $R_2$ are, independently, an organic group having 1-20 carbon atoms, or $R_1$ and $R_2$ are linked to form a ring structure with E;
$R_{12}$ is an organic group having 1-20 carbon atoms;
$R_{20}$, $R_{21}$, $R_{22}$, $R_{23}$ and $R_{24}$ are, independently, —H or an organic group having 1-20 carbon atoms; or
one or more pairs of $R_1/R_{20}$, $R_2/R_{20}$, $R_{20}/R_{21}$ or $R_{22}/R_{23}$, independently, form a ring structure with the atoms to which they are attached;
m is 0, 1, 2, 3, 4 or 5; and
$X^⊕$ is a non-coordinated anionic ligand.

17. A palladium(II) complex according to claim 16, wherein $R_1$ and $R_2$ are, independently, substituted or unsubstituted straight-chain alkyl, substituted or unsubstituted branched-chain alkyl, substituted or unsubstituted cycloalkyl, substituted or unsubstituted aryl, or substituted or unsubstituted heteroaryl wherein the heteroatoms of the heteroaryl are independently, sulfur, nitrogen or oxygen.

18. A palladium(II) complex according to claim 16, wherein each $R_{12}$ is, independently, substituted or unsubstituted straight-chain alkyl, substituted or unsubstituted branched-chain alkyl, substituted or unsubstituted cycloalkyl, substituted or unsubstituted aryl, or substituted or unsubstituted heteroaryl wherein the heteroatoms of the heteroaryl are, independently, sulfur, nitrogen or oxygen.

19. A palladium(II) complex according to claim 16, wherein $X^⊕$ is triflate, tetrafluoroborate, hexafluoroantimonate, hexafluorophosphate, [B[3,5-(CF₃)₂C₆H₃]₄]⁻ or mesylate.

20. A palladium(II) complex according to claim 16, wherein $R_{20}$ and $R_{21}$ are, independently, —H, substituted or unsubstituted straight-chain alkyl, substituted or unsubstituted branched-chain alkyl, substituted or unsubstituted cycloalkyl, substituted or unsubstituted alkoxy, substituted or unsubstituted aryl, or substituted or unsubstituted heteroaryl, substituted or unsubstituted —N(alkyl)₂ (wherein the alkyl is the same or different and, independently, straight-chain or branched-chain alkyl), substituted or unsubstituted —N(cycloalkyl)₂ (wherein the cycloalkyl is the same or different), substituted or unsubstituted —N(aryl)₂ (wherein the aryl is the same or different), substituted or unsubstituted —N(heteroaryl)₂ (wherein the heteroaryl is the same or different) or substituted or unsubstituted heterocycloalkyl.

21. A palladium(II) complex according to claim 20, wherein $R_{20}$ and $R_{21}$ are —H.

22. A palladium(II) complex according to claim 16, wherein $R_{22}$ and $R_{24}$ are, independently, —H, substituted or unsubstituted straight-chain alkyl, substituted or unsubstituted branched-chain alkyl, substituted or unsubstituted cycloalkyl, substituted or unsubstituted alkoxy, substituted or unsubstituted thioalkyl, substituted or unsubstituted aryl, substituted or unsubstituted heteroaryl, substituted or unsubstituted —N(alkyl)₂ (wherein the alkyl is the same or different and, independently, straight-chain or branched-chain alkyl), substituted or unsubstituted —N(cycloalkyl)₂ (wherein the cycloalkyl is the same or different), substituted or unsubstituted —N(aryl)₂ (wherein the aryl is the same or different), or substituted or unsubstituted —N(heteroaryl)₂ (wherein the heteroaryl is the same or different).

23. A palladium(II) complex according to claim 16, wherein $R_{23}$ is —H, substituted or unsubstituted straight-chain alkyl, substituted or unsubstituted branched-chain alkyl, substituted or unsubstituted cycloalkyl, substituted or unsubstituted alkoxy, substituted or unsubstituted aryl, or substituted and unsubstituted heteroaryl.

24. A palladium(II) complex according to claim 16, wherein $R_{22}$, $R_{23}$ and $R_{24}$ are phenyl.

25. A palladium(II) complex according to claim 16, wherein the complex of formula (3) is:

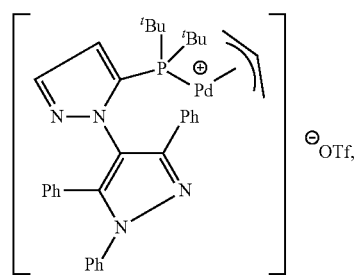

[(π-allyl)Pd(BippyPhos)]OTf

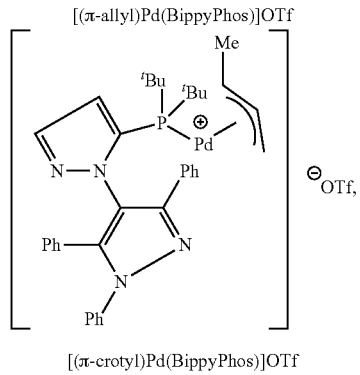

[(π-crotyl)Pd(BippyPhos)]OTf

-continued

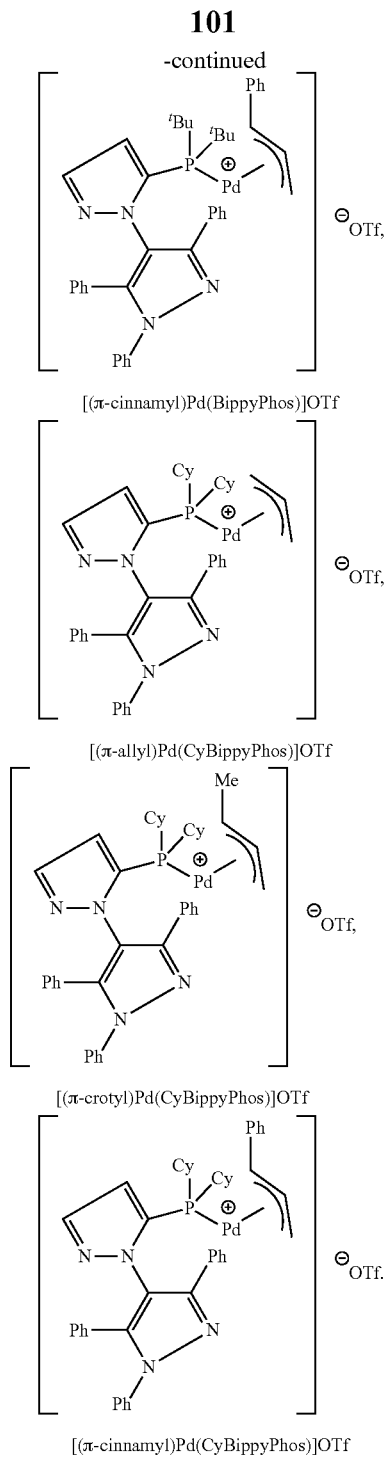

[(π-cinnamyl)Pd(BippyPhos)]OTf

[(π-allyl)Pd(CyBippyPhos)]OTf

[(π-crotyl)Pd(CyBippyPhos)]OTf

[(π-cinnamyl)Pd(CyBippyPhos)]OTf

26. A process for preparing a complex of formula (1), the process comprising the steps of:
(a) reacting a complex of formula (4) with a monodentate biaryl ligand of formula (5) to form a complex of formula (6)

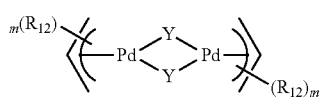
(4)

-continued

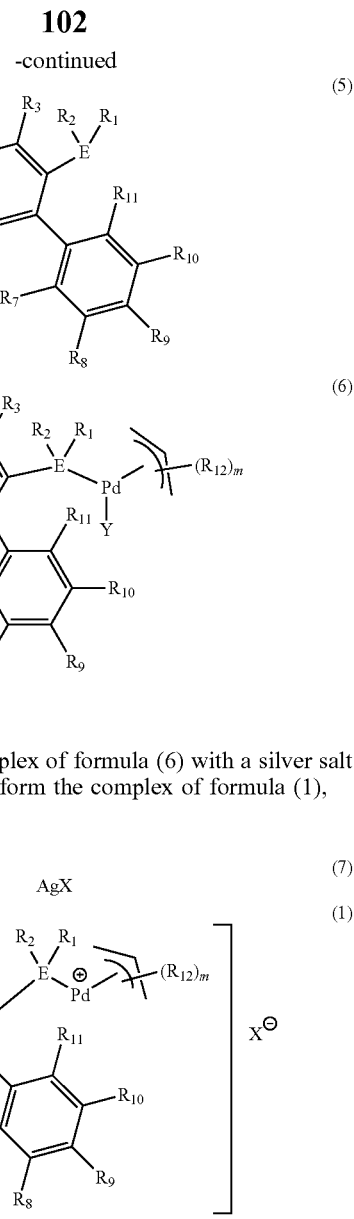

and;
(b) reacting the complex of formula (6) with a silver salt of formula (7) to form the complex of formula (1), wherein:
$R_1$ and $R_2$ are, independently, an organic group having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are, independently, —H or an organic group having 1-20 carbon atoms; or one or more pairs selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$, independently, form a ring structure with the atoms to which they are attached;
$R_{12}$ is an organic group having 1-20 carbon atoms;
m is 0, 1, 2, 3, 4 or 5;
E is P or As;
Y is a coordinating anionic ligand; and
$X^\oplus$ is a non-coordinated anionic ligand.

27. A process for preparing a complex of formula (1) or a complex of formula (3), the process comprising the steps of:
(a) reacting a complex of formula (4) with a silver salt of formula (7),

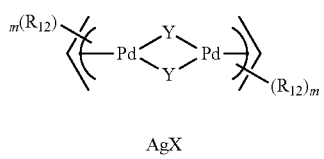

and;

(b) reacting the product of step (a) with a monodentate biaryl ligand of formula (5) or a monodentate bi-heteroaryl tertiary phosphine ligand of formula (8) to form the complex of formula (1) or the complex of formula (3),

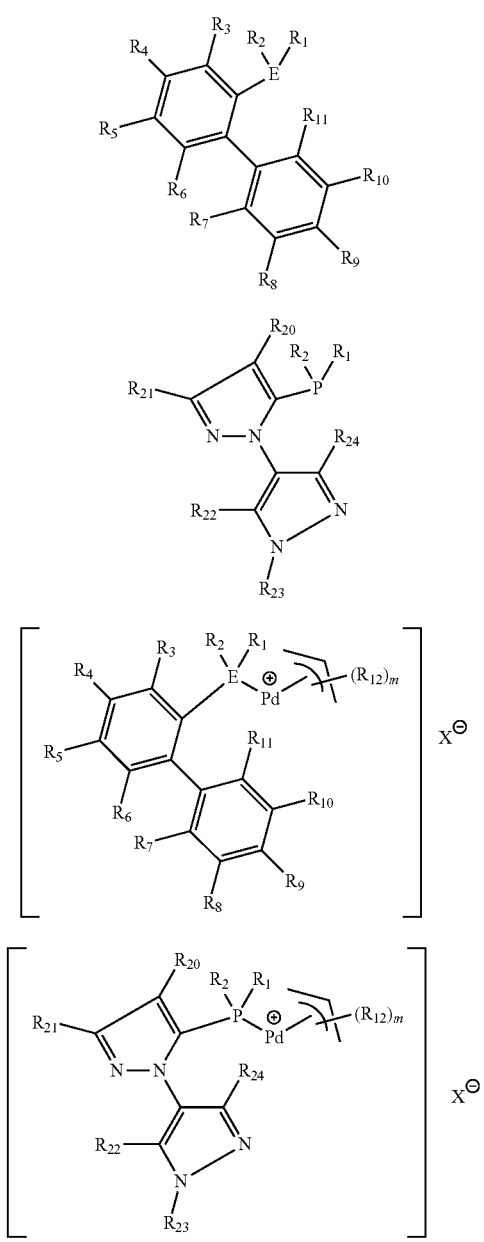

wherein:

$R_1$ and $R_2$ are, independently, an organic group having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are, independently, —H or an organic group having 1-20 carbon atoms; or one or more pairs selected from $R_1/R_2$, $R_2/R_3$, $R_3/R_4$, $R_4/R_5$, $R_5/R_6$, $R_7/R_8$, $R_8/R_9$, $R_9/R_{10}$ or $R_{10}/R_{11}$, independently, form a ring structure with the atoms to which they are attached;

$R_{12}$ is an organic group having 1-20 carbon atoms;

$R_{20}$, $R_{21}$, $R_{22}$, $R_{23}$ and $R_{24}$ are, independently, —H or an organic group having 1-20 carbon atoms; or one or more pairs of $R_1/R_{20}$, $R_2/R_{20}$, $R_{20}/R_{21}$ or $R_{22}/R_{23}$, independently, form a ring structure with the atoms to which they are attached;

m is 0, 1, 2, 3, 4 or 5;

E is P or As;

Y is a coordinating anionic ligand; and $X^{\oplus}$ is a non-coordinated anionic ligand.

28. A process for performing a carbon-carbon coupling reaction in the presence of a catalyst, the process comprising using a complex of formula (1) according to claim 1 or a complex of formula (3):

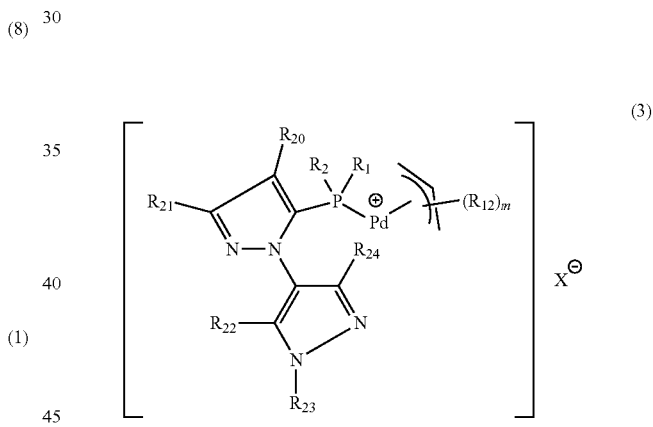

wherein:

$R_1$ and $R_2$ are, independently, an organic group having 1-20 carbon atoms, or $R_1$ and $R_2$ are linked to form a ring structure with E;

$R_{12}$ is an organic group having 1-20 carbon atoms;

$R_{20}$, $R_{21}$, $R_{22}$, $R_{23}$ and $R_{24}$ are, independently, —H or an organic group having 1-20 carbon atoms; or one or more pairs of $R_1/R_{20}$, $R_2/R_{20}$, $R_{20}/R_{21}$ or $R_{22}/R_{23}$ independently form a ring structure with the atoms to which they are attached;

m is 0, 1, 2, 3, 4 or 5; and $X^{\oplus}$ is a non-coordinated anionic ligand.

29. A process for performing a carbon-heteroatom coupling reaction in the presence of a catalyst, the process comprising using a complex of formula (1) according to claim 1 or a complex of formula (3):

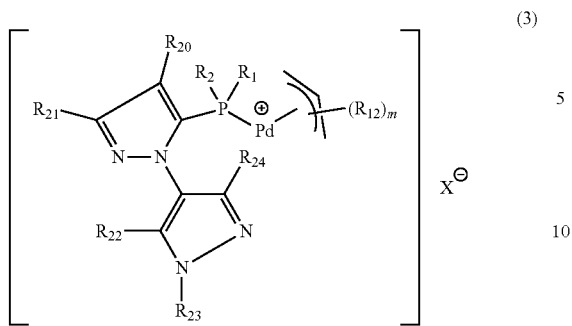

(3)

wherein:
R$_1$ and R$_2$ are, independently, an organic group having 1-20 carbon atoms, or R$_1$ and R$_2$ are linked to form a ring structure with E;
R$_{12}$ is an organic group having 1-20 carbon atoms;
R$_{20}$, R$_{21}$, R$_{22}$, R$_{23}$ and R$_{24}$ are, independently, —H or an organic group having 1-20 carbon atoms; or
one or more pairs of R$_1$/R$_{20}$, R$_2$/R$_{20}$, R$_{20}$/R$_{21}$ or R$_{22}$/R$_{23}$, independently, form a ring structure with the atoms to which they are attached;
m is 0, 1, 2, 3, 4 or 5; and
X$^\oplus$ is a non-coordinated anionic ligand.

30. A palladium (II) complex according to claim 6, wherein R$_3$, R$_4$, R$_5$ and R$_6$ are –Me.

* * * * *